US012673201B1

(12) United States Patent
Hendricks et al.

(10) Patent No.: US 12,673,201 B1
(45) Date of Patent: Jul. 7, 2026

(54) SYSTEM AND METHODS FOR A CRANIAL LEAD FIXATION DEVICE

(71) Applicant: Dignity Health, San Francisco, CA (US)

(72) Inventors: Benjamin K. Hendricks, San Francisco, CA (US); Dakota Graham, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 799 days.

(21) Appl. No.: 17/939,881

(22) Filed: Sep. 7, 2022

Related U.S. Application Data

(60) Provisional application No. 63/241,217, filed on Sep. 7, 2021.

(51) Int. Cl.
    *A61N 1/05*     (2006.01)
    *A61B 5/00*     (2006.01)
    *A61M 39/02*     (2006.01)
(52) U.S. Cl.
    CPC .......... *A61N 1/0539* (2013.01); *A61B 5/6864* (2013.01); *A61M 39/0247* (2013.01); *A61N 1/0529* (2013.01); *A61M 2210/0687* (2013.01); *A61M 2210/0693* (2013.01)

(58) Field of Classification Search
CPC ............ A61N 1/0539; A61B 2090/103; A61B 2017/3407; A61B 2017/3492; A61B 90/11; A61M 39/0247
See application file for complete search history.

(56) References Cited

U.S. PATENT DOCUMENTS

| | | | | |
|---|---|---|---|---|
| 6,134,477 A | * | 10/2000 | Knuteson | A61N 1/0539 607/115 |
| 7,949,410 B2 | * | 5/2011 | Rodriguez | A61N 1/0531 607/116 |
| 2005/0182464 A1 | * | 8/2005 | Schulte | A61N 1/0539 604/174 |
| 2010/0023020 A1 | * | 1/2010 | Barker | A61B 90/50 606/129 |
| 2020/0139110 A1 | * | 5/2020 | Smith | A61N 1/0534 |

* cited by examiner

*Primary Examiner* — Brigid K Byrd
(74) *Attorney, Agent, or Firm* — Posinelli PC

(57) ABSTRACT

A cranial lead fixation device includes a body configured for fixation to a cranium over or within a burr hole, and a fixation mechanism associated with the body. The body and fixation mechanism capture a medical device (e.g., a lead, catheter, or similar device) within a fixation channel of the cranial lead fixation device for protection of the burr hole and securement of the medical device. The cranial lead fixation device is operable for a first open configuration and a second closed configuration.

17 Claims, 55 Drawing Sheets

500

600

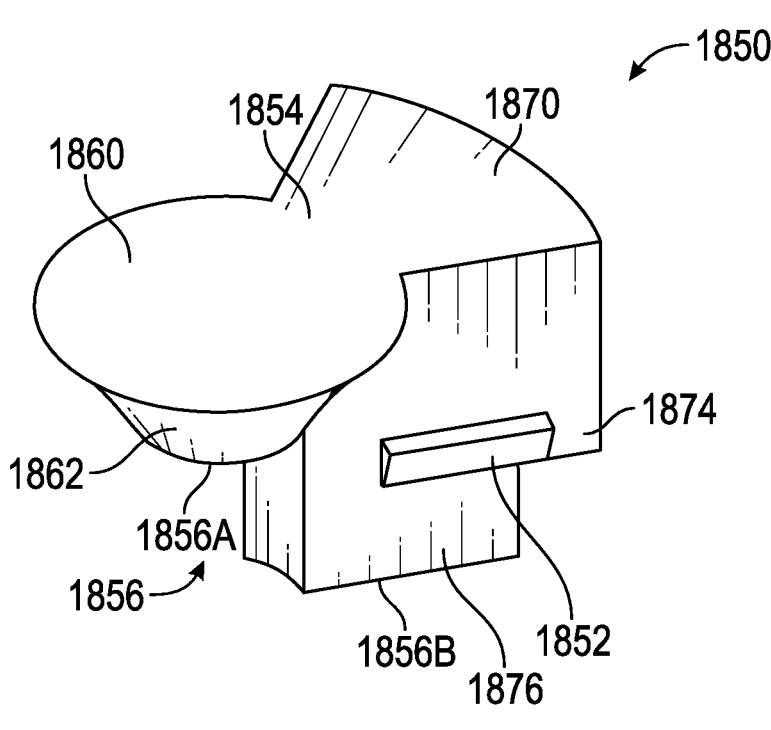
FIG. 25A
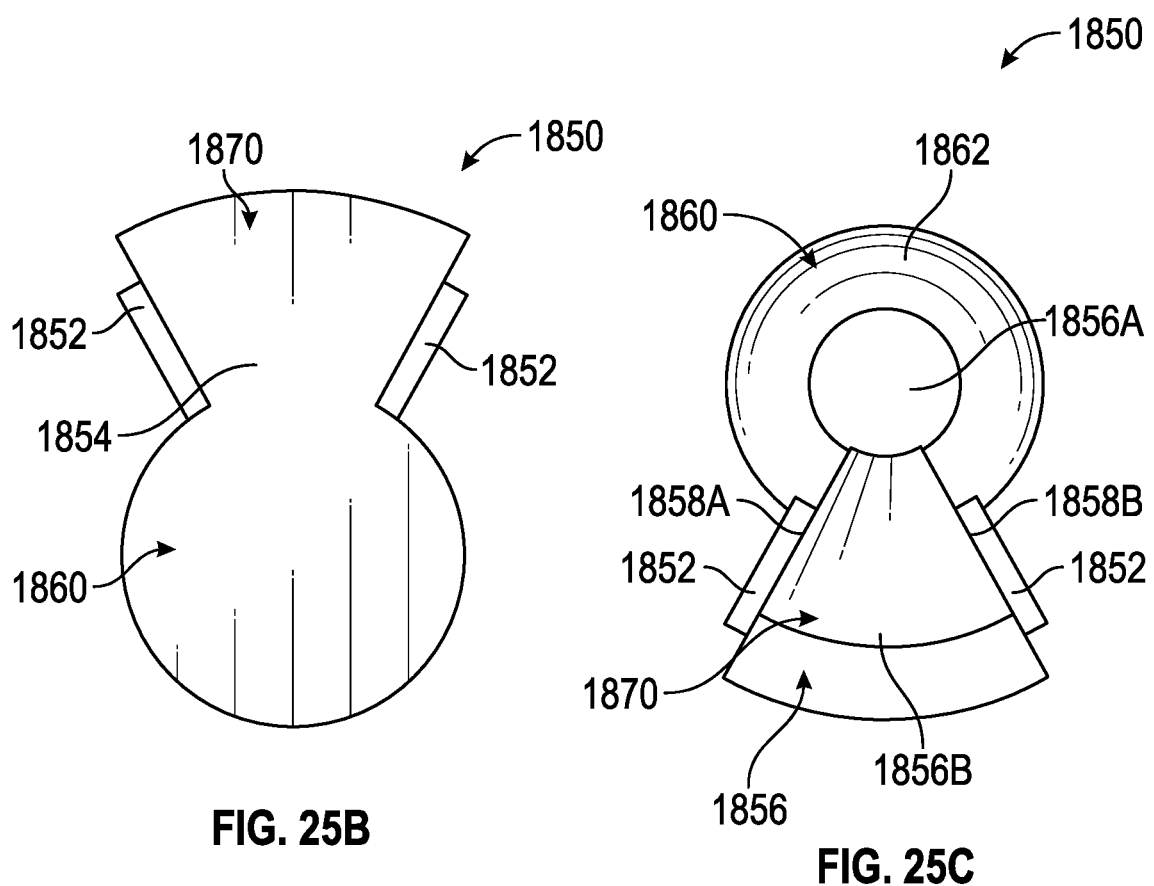
FIG. 25B
FIG. 25C

Figure 28A:
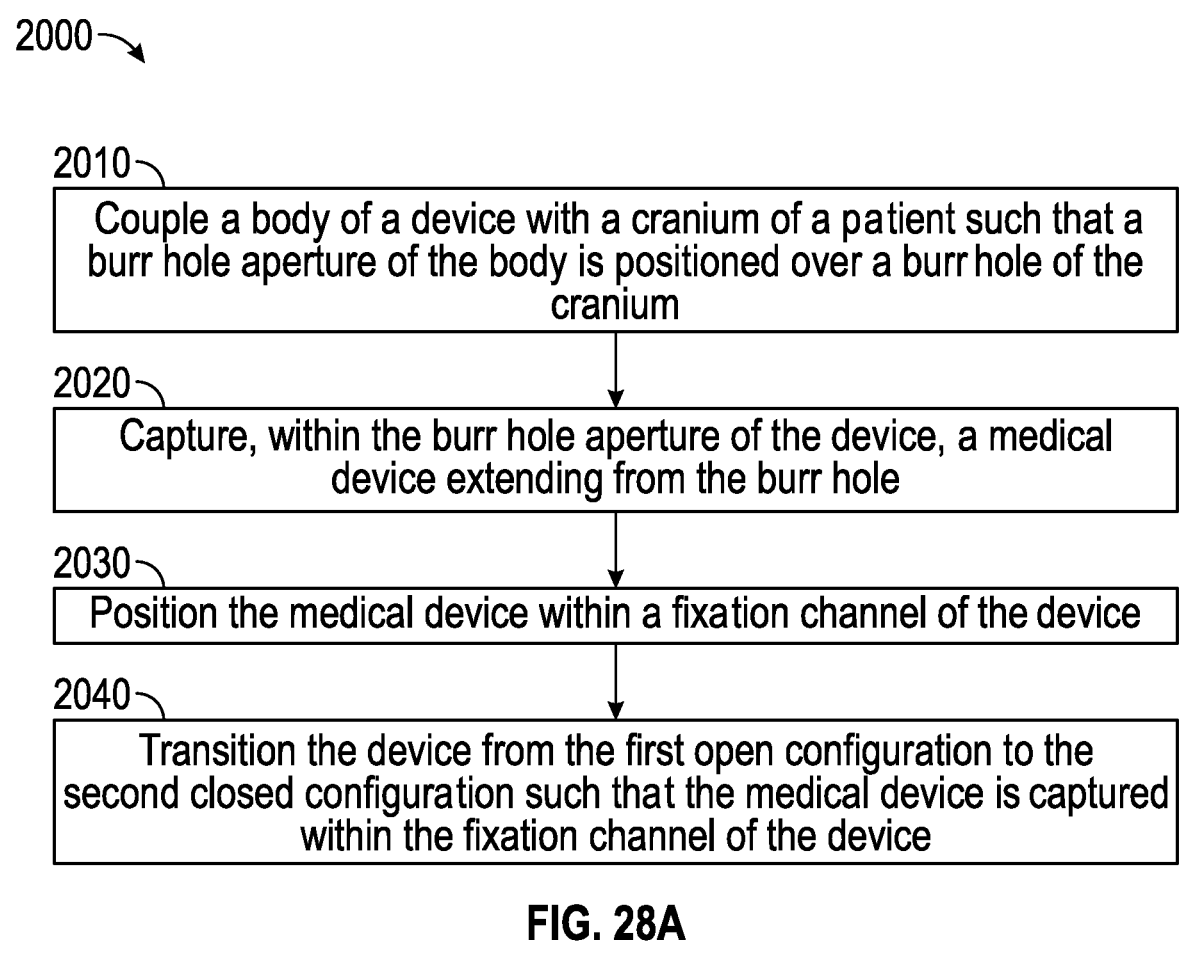

2000 ⟍

2010 ⟍

| Couple a body of a device with a cranium of a patient such that a burr hole aperture of the body is positioned over a burr hole of the cranium |
|---|

2020 ⟍

| Capture, within the burr hole aperture of the device, a medical device extending from the burr hole |
|---|

2030 ⟍

| Position the medical device within a fixation channel of the device |
|---|

2040 ⟍

| Transition the device from the first open configuration to the second closed configuration such that the medical device is captured within the fixation channel of the device |
|---|

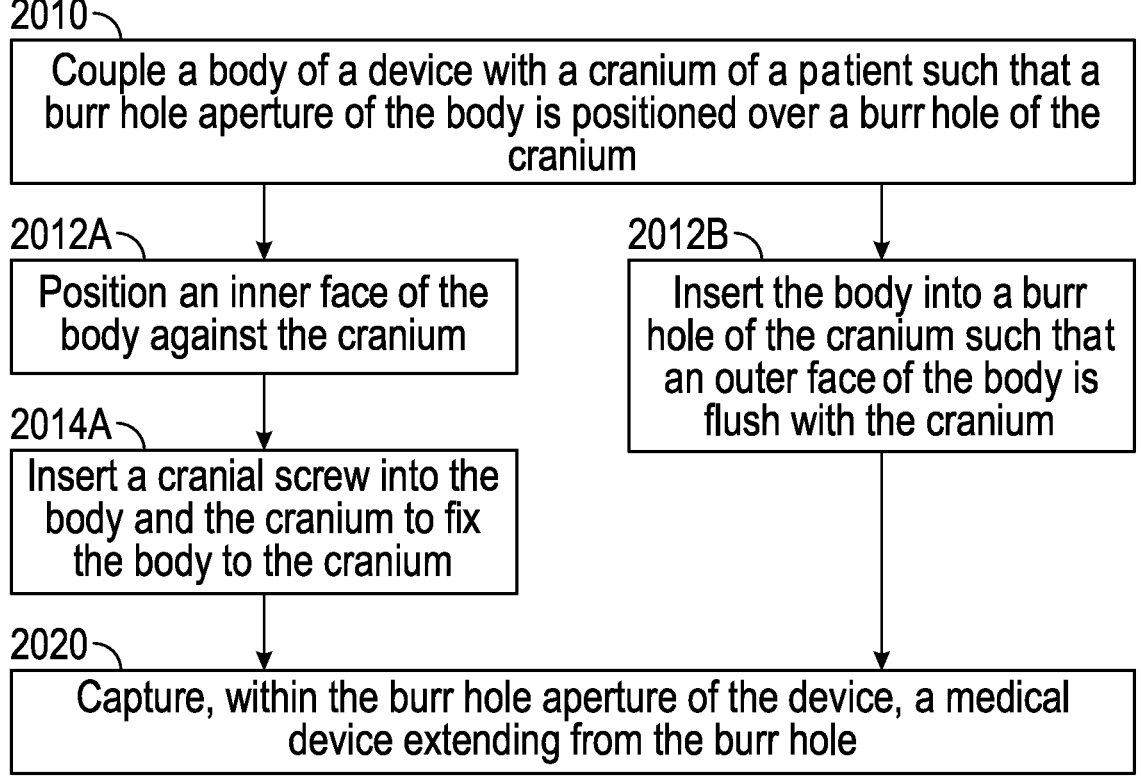

2010 ⬎

Couple a body of a device with a cranium of a patient such that a burr hole aperture of the body is positioned over a burr hole of the cranium

2012A ⬎

Position an inner face of the body against the cranium

2012B ⬎

Insert the body into a burr hole of the cranium such that an outer face of the body is flush with the cranium

2014A ⬎

Insert a cranial screw into the body and the cranium to fix the body to the cranium

2020 ⬎

Capture, within the burr hole aperture of the device, a medical device extending from the burr hole

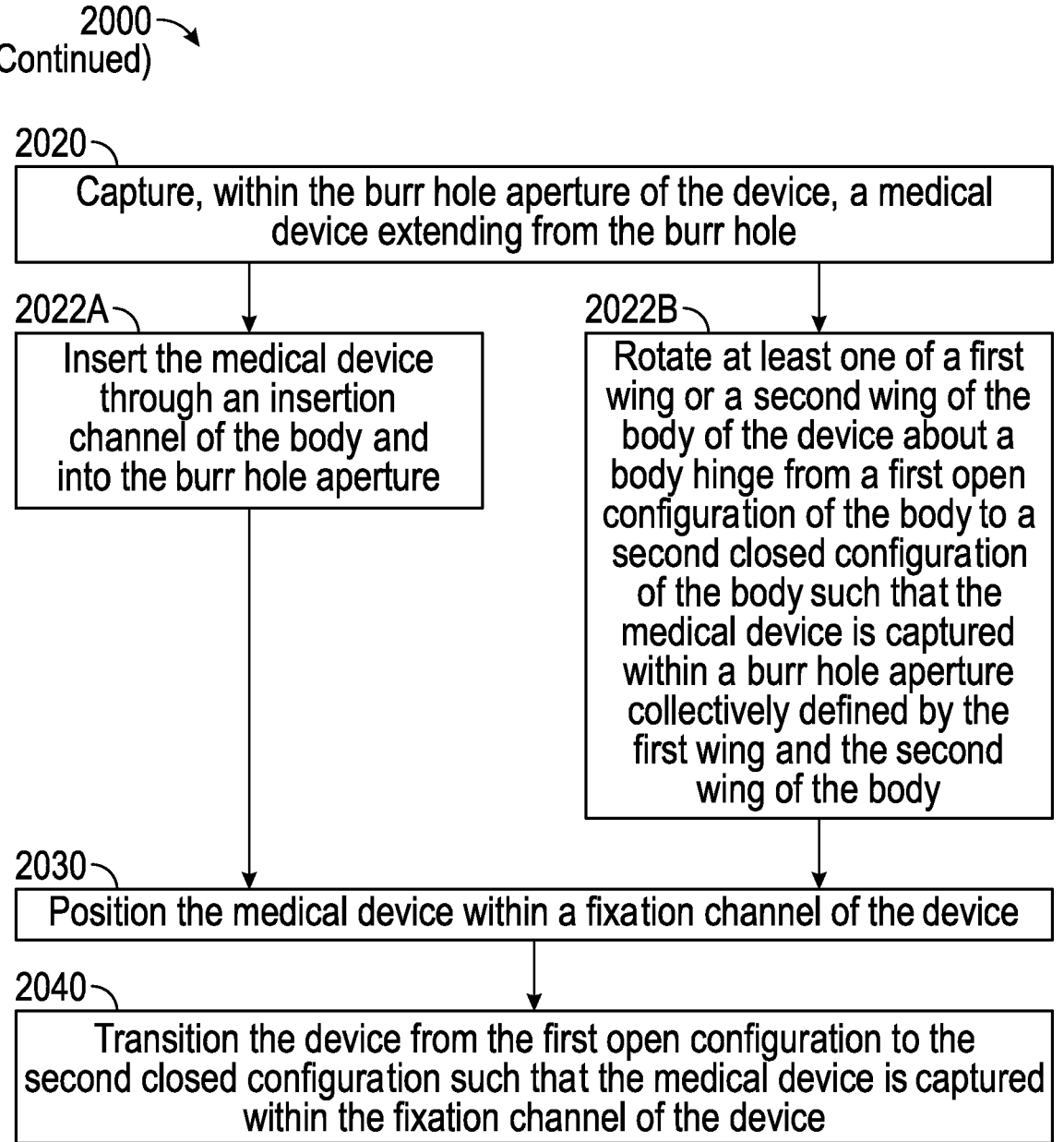

2020 ⟍
Capture, within the burr hole aperture of the device, a medical device extending from the burr hole 2022A ⟍
Insert the medical device through an insertion channel of the body and into the burr hole aperture 2022B ⟍
Rotate at least one of a first wing or a second wing of the body of the device about a body hinge from a first open configuration of the body to a second closed configuration of the body such that the medical device is captured within a burr hole aperture collectively defined by the first wing and the second wing of the body 2030 ⟍
Position the medical device within a fixation channel of the device 2040 ⟍
Transition the device from the first open configuration to the second closed configuration such that the medical device is captured within the fixation channel of the device

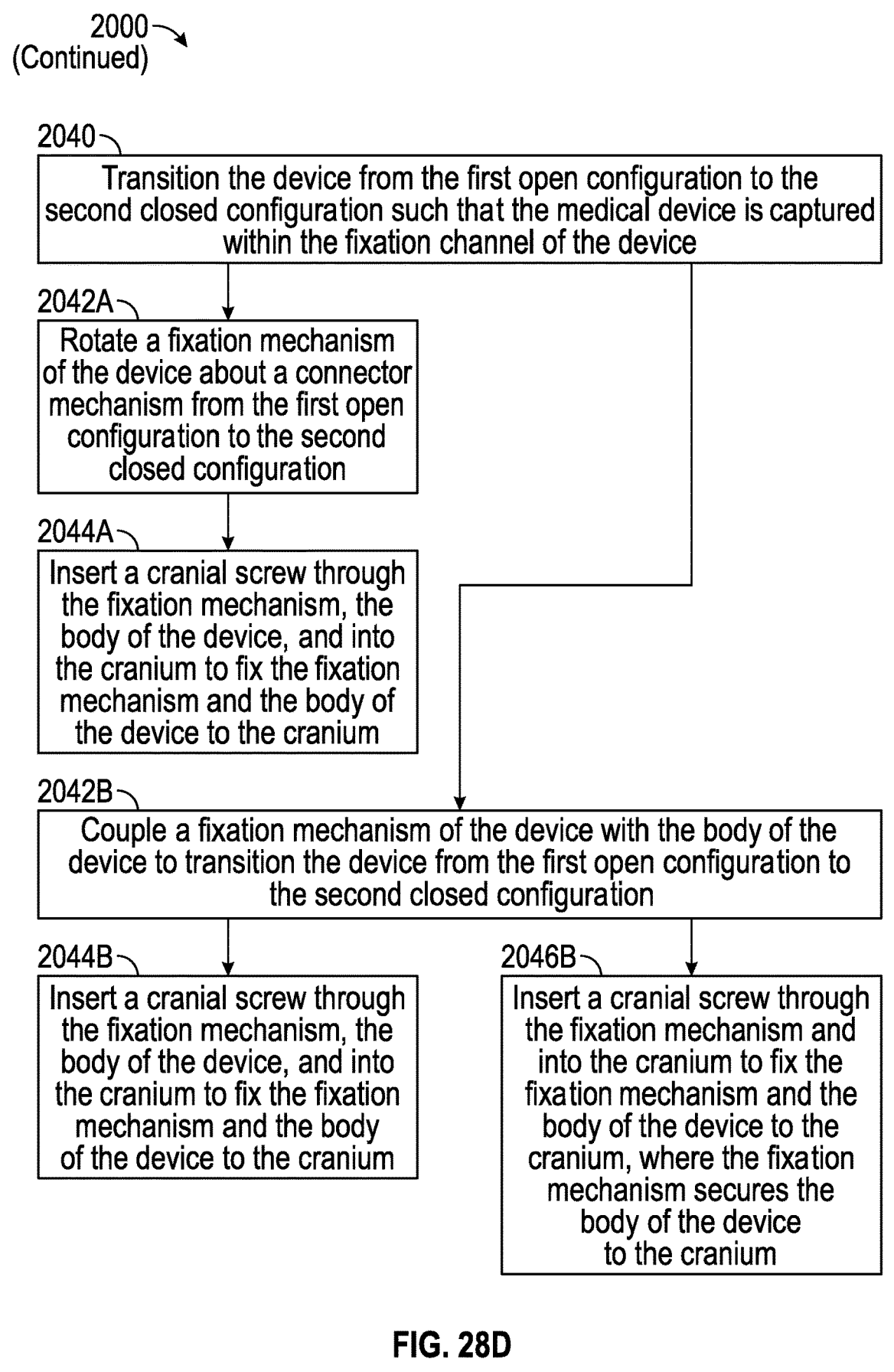

FIG. 28C 2000
(Continued)

2040
Transition the device from the first open configuration to the second closed configuration such that the medical device is captured within the fixation channel of the device 2042A
Rotate a fixation mechanism of the device about a connector mechanism from the first open configuration to the second closed configuration 2044A
Insert a cranial screw through the fixation mechanism, the body of the device, and into the cranium to fix the fixation mechanism and the body of the device to the cranium 2042B
Couple a fixation mechanism of the device with the body of the device to transition the device from the first open configuration to the second closed configuration 2044B
Insert a cranial screw through the fixation mechanism, the body of the device, and into the cranium to fix the fixation mechanism and the body of the device to the cranium 2046B
Insert a cranial screw through the fixation mechanism and into the cranium to fix the fixation mechanism and the body of the device to the cranium, where the fixation mechanism secures the body of the device to the cranium

FIG. 28D

2000
(Continued)

2040
Transition the device from the first open configuration to the second closed configuration such that the medical device is captured within the fixation channel of the device 2042C
Translate a fixation mechanism of the device from a first lateral position associated with the first open configuration to a second lateral position associated with the second closed configuration 2044C
Insert a cranial screw through the fixation mechanism, the body of the device, and into the cranium to fix the fixation mechanism and the body of the device to the cranium

FIG. 28E

SYSTEM AND METHODS FOR A CRANIAL LEAD FIXATION DEVICE

CROSS-REFERENCE TO RELATED APPLICATIONS

This is a U.S. Non-Provisional patent application that claims benefit to U.S. Provisional Patent Application Ser. No. 63/241,217 filed Sep. 7, 2021, which is herein incorporated by reference in its entirety.

FIELD

The present disclosure generally relates to the implantation of electrodes; and in particular, to systems and methods for a cranial lead fixation device.

BACKGROUND

Deep brain stimulation was first approved by the US Food and Drug Administration (FDA) in 2002 for the treatment of Parkinson's disease (PD). Indications for electrode implantation have expanded to include multiple additional pathologies including essential tremor, dystonia, obsessive-compulsive disorder, epilepsy, and is currently under investigation for multiple additional pathologies. The implantation of electrodes within the brain requires rigid fixation at the level of the cranium to reduce the risk of electrode migration and pullout. Historically this has been accomplished by two primary methods, either with use of a standardized burr-hole device provided by the hardware manufacturer or the use of oxidized cellulose polymer with acrylic cement. The currently available products from the manufacturer provide a convenient solution to the problem but possess a tall vertical and wide profile which negatively impacts wound healing and placement within a small scalp incision.

Currently available and described technologies for cranial electrode fixation along the cranium lack the low vertical profile and narrow horizontal profile necessary to place electrodes in a minimally invasive manner, with a low cosmetic impact to the patient.

It is with these observations in mind, among others, that various aspects of the present disclosure were conceived and developed.

BRIEF DESCRIPTION OF THE DRAWINGS

FIG. 25A is a top perspective view showing a fixation mechanism of the cranial lead fixation device of FIG. 23B;

FIG. 25B is a top plan view showing the fixation mechanism of FIG. 25A;

FIG. 25C is a bottom plan view showing the fixation mechanism of FIG. 25A;

FIGS. 28A-28E are a series of process flow diagrams showing a method of capturing a medical device using the cranial lead fixation devices of FIGS. 1A-27D.

Corresponding reference characters indicate corresponding elements among the view of the drawings. The headings used in the figures do not limit the scope of the claims.

DETAILED DESCRIPTION

Figure 1A:
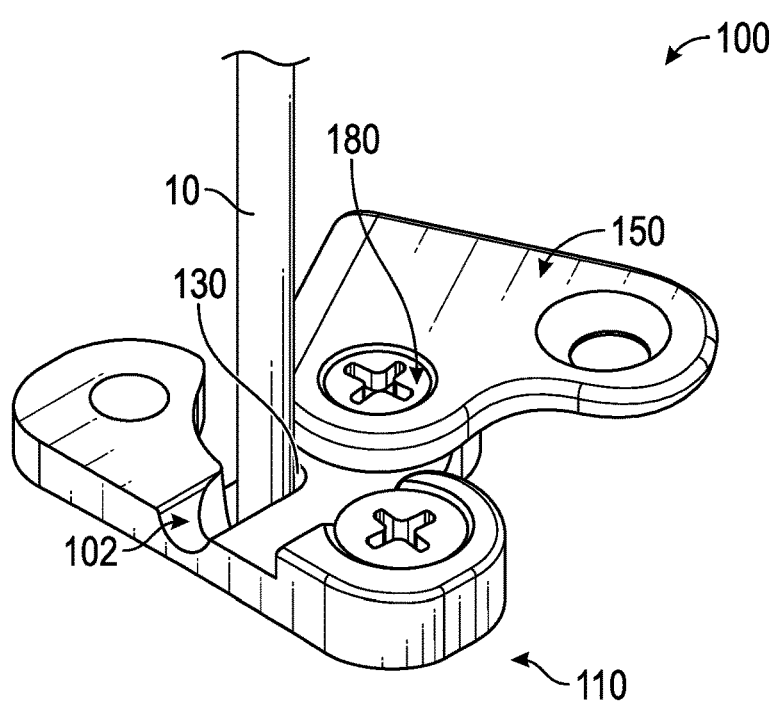
FIG. 1A is a front perspective view showing a cranial lead fixation device in a first open configuration and coupled along a cranium for capture of a medical device.

Various embodiments for systems and methods for a cranial lead fixation device that secures a medical device to a cranium of a patient are disclosed herein. For example, in some embodiments the medical device can include an electrode or a conformable grid having a plurality of electrodes used for deep brain simulation. Other embodiments may use medical devices such as catheters used for shunt valves and drainage of cerebrospinal fluid. In some embodiments, the cranial lead fixation device is configured to receive one or more cranial screws for securing the cranial lead fixation device to the cranium of the patient. The cranial lead fixation device includes a fixation channel configured and arranged to capture the medical device. In one aspect, the cranial lead fixation device is configured for transitioning between a first open configuration and a second closed configuration. The cranial lead fixation device includes a body that affixes directly to the cranium over or within a burr hole of the cranium, and further includes a fixation mechanism that transitions the cranial lead fixation device between the first open configuration and the second closed configuration to capture the medical device. The cranial lead fixation device secures and protects the medical device and the burr hole.

FIGS. 1A-4B show a first embodiment of the cranial lead fixation device, designated as cranial lead fixation device 100, for capturing and securing a medical device 10 within a burr hole 30 formed within a cranium 20; the medical device can include a lead of a deep brain stimulation device, a catheter, or another medical device of a similar configuration that extends from inside the cranium 20 to an exterior environment along an exterior of the cranium 20. FIGS. 1A-1F in particular show the cranial lead fixation device 100 positioned along the cranium 20, with FIGS. 1E and 1F showing cross-sectional views of the cranial lead fixation device 100 positioned along the cranium 20 and over the burr hole 30 for capture of the medical device 10. As shown, the cranial lead fixation device 100 is operable to assume a first open configuration (FIGS. 1A and 1B) and a second closed configuration (FIGS. 1C and 1D). Further, the cranial lead fixation device 100 includes a fixation channel 102 for receipt of the medical device 10 such that when the cranial lead fixation device 100 is in the first open configuration, the fixation channel 102 is "open" and operable to accept the medical device 10. When the cranial lead fixation device 100 is in the second "closed" configuration, the fixation channel 102 captures the medical device 10 such that the medical device 10 is prevented from being removed or otherwise pulled away from the cranium 20.

Figure 1B:
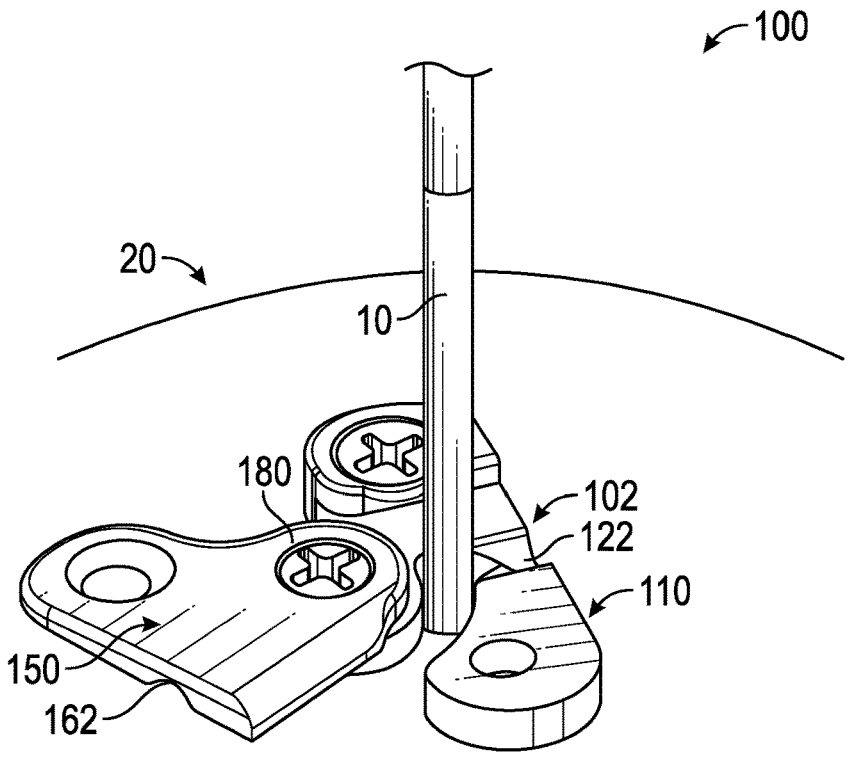
FIG. 1B is a rear perspective view showing the cranial lead fixation device of FIG. 1A in the first open configuration and coupled along the cranium for capture of the medical device.
Figure 1C:
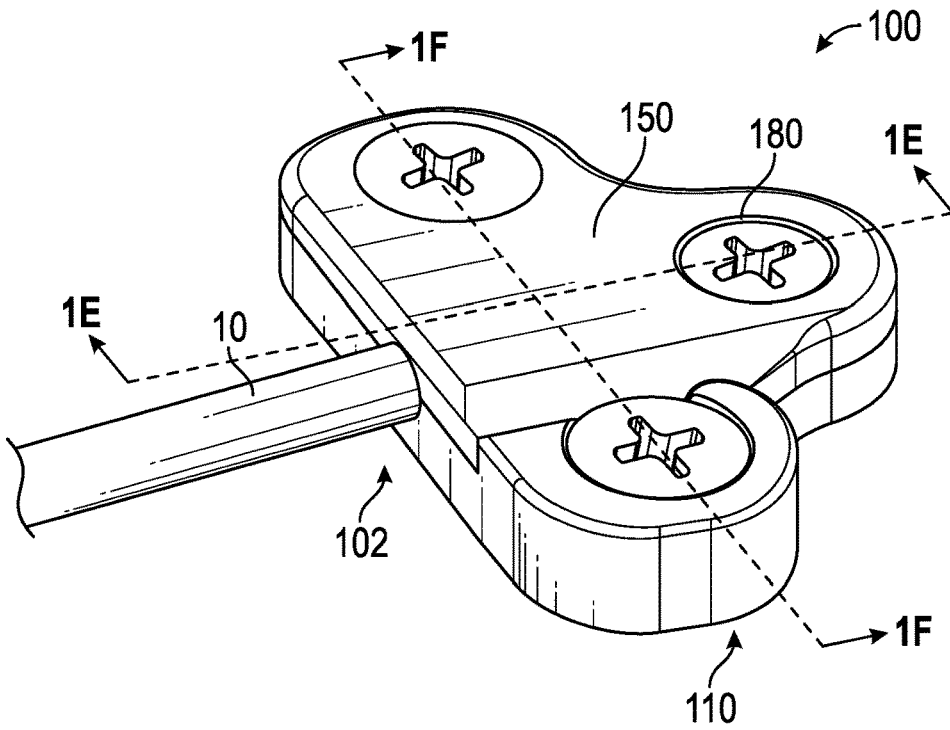
FIG. 1C is a front perspective view showing the cranial lead fixation device of FIG. 1A in a second closed configuration and coupled along the cranium for capture of the medical device.
Figure 1D:
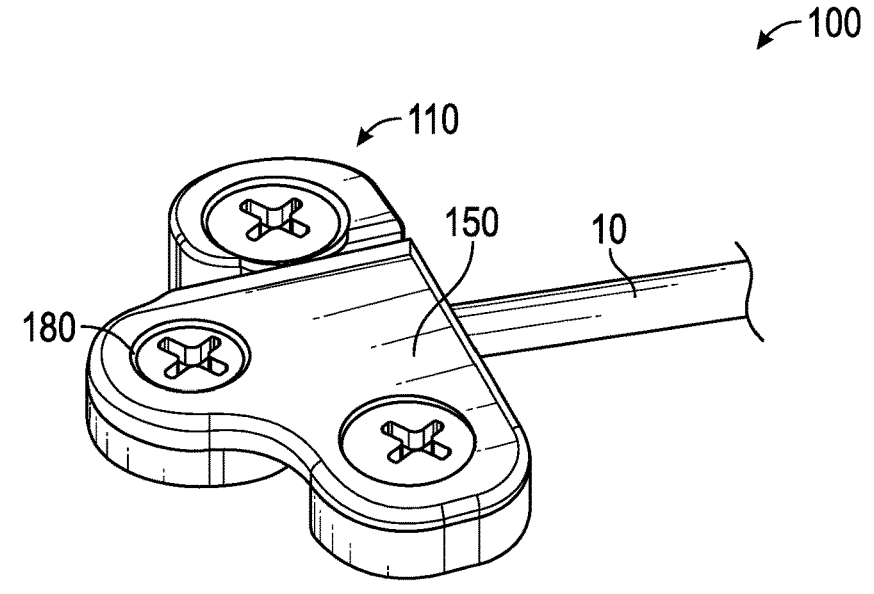
FIG. 1D is a rear perspective view showing the cranial lead fixation device of FIG. 1C in the second closed configuration and coupled along a cranium for capture of the medical device.
Figure 2A:
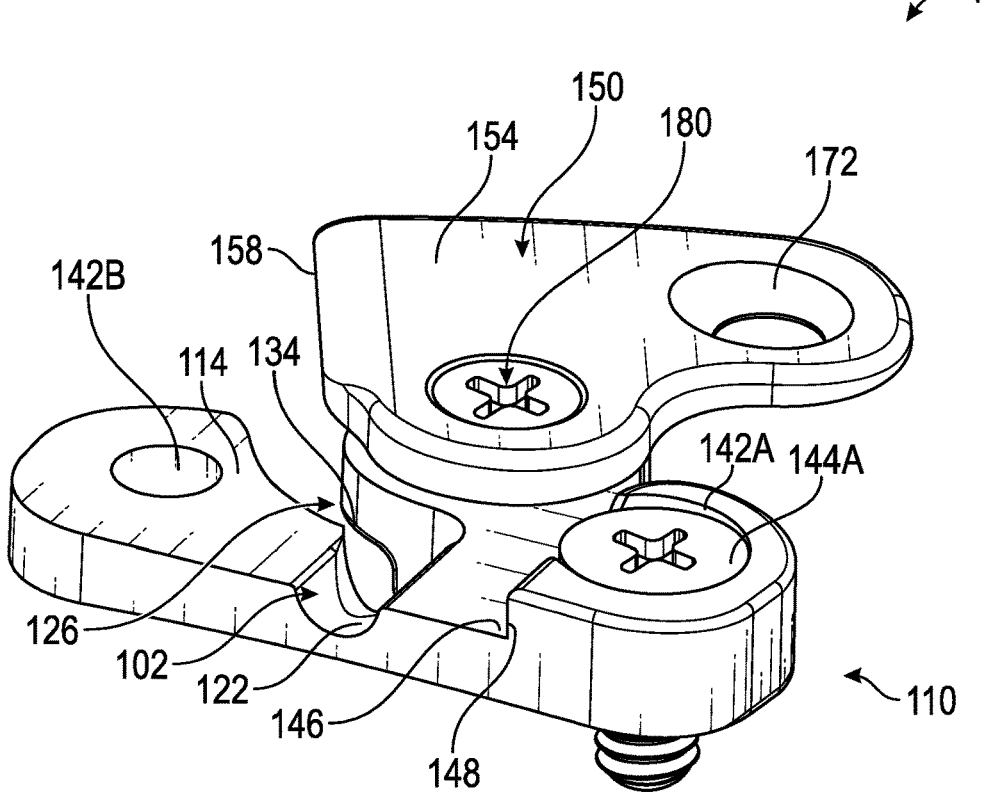
FIG. 2A is a front perspective view showing the cranial lead fixation device of FIG. 1A in the first open configuration.
Figure 2B:
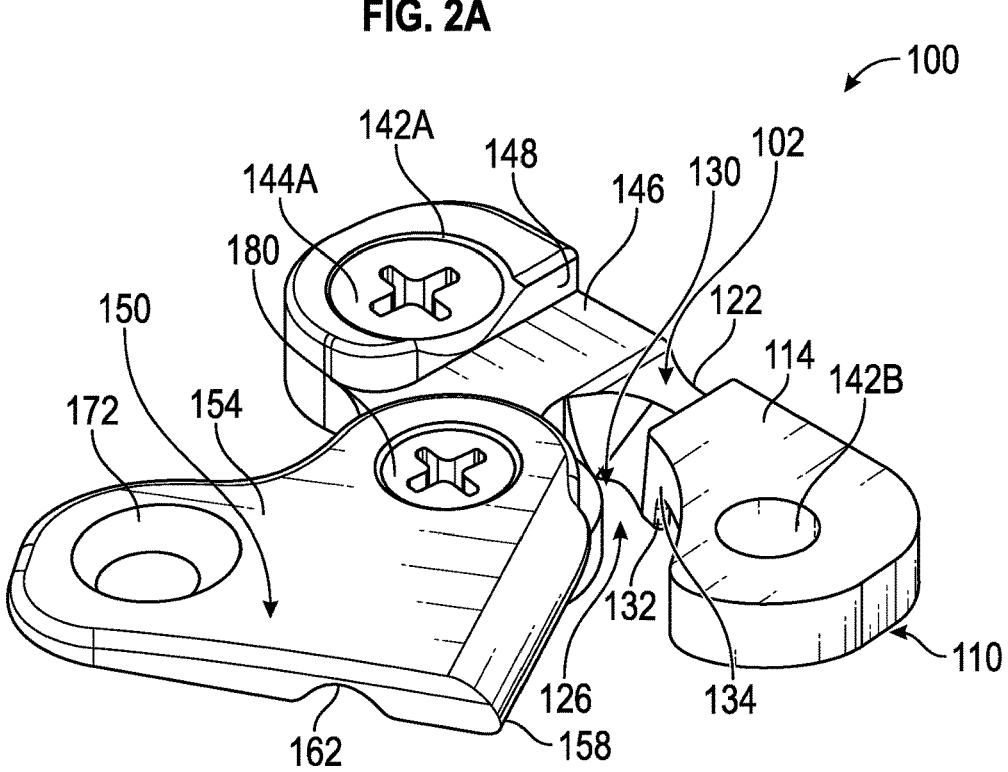
FIG. 2B is a rear perspective view showing the cranial lead fixation device of FIG. 2A in the first open configuration.
Figure 2C:
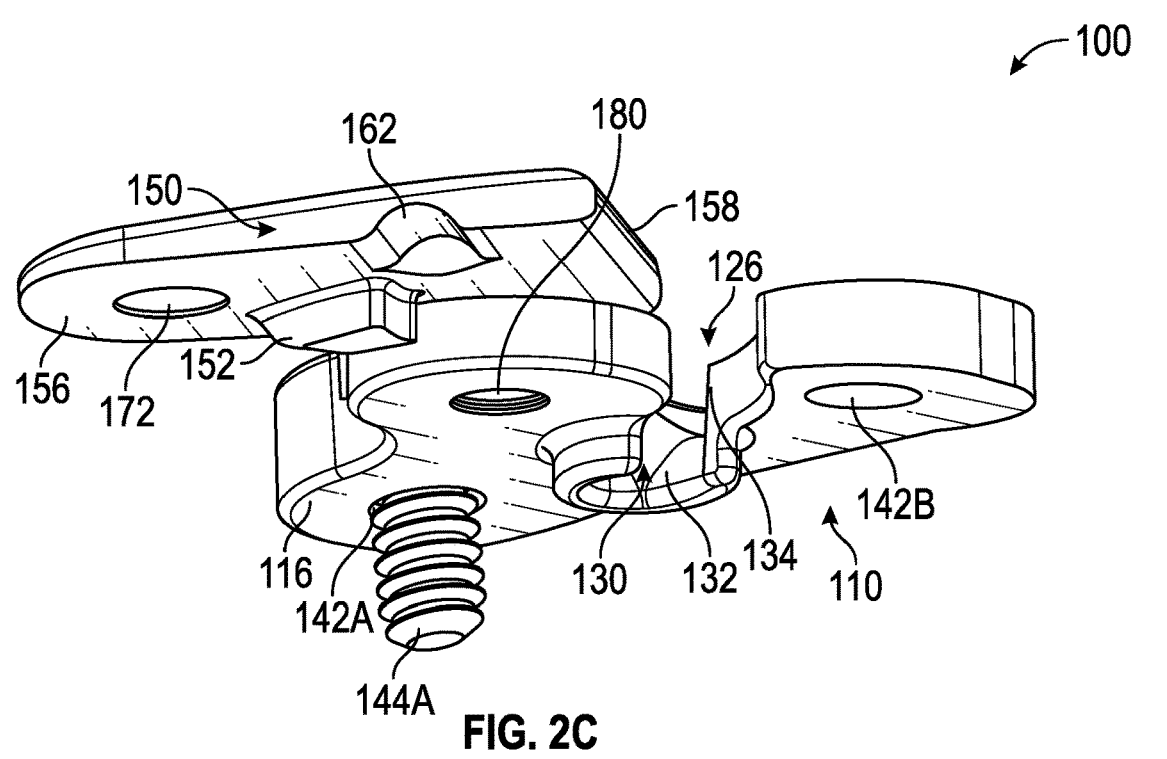
FIG. 2C is a rear underside perspective view showing the cranial lead fixation device of FIG. 2A in the first open configuration.
Figure 2D:
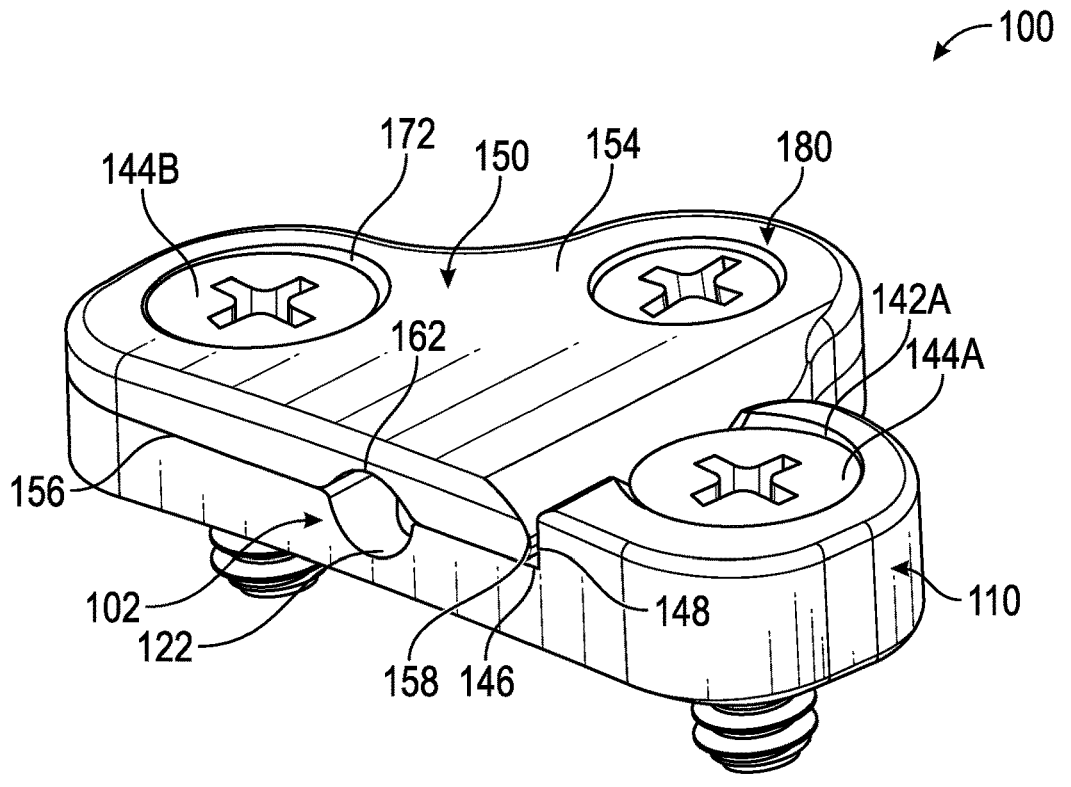
FIG. 2D is a front perspective view showing the cranial lead fixation device of FIG. 2A in the second closed configuration.
Figure 2E:
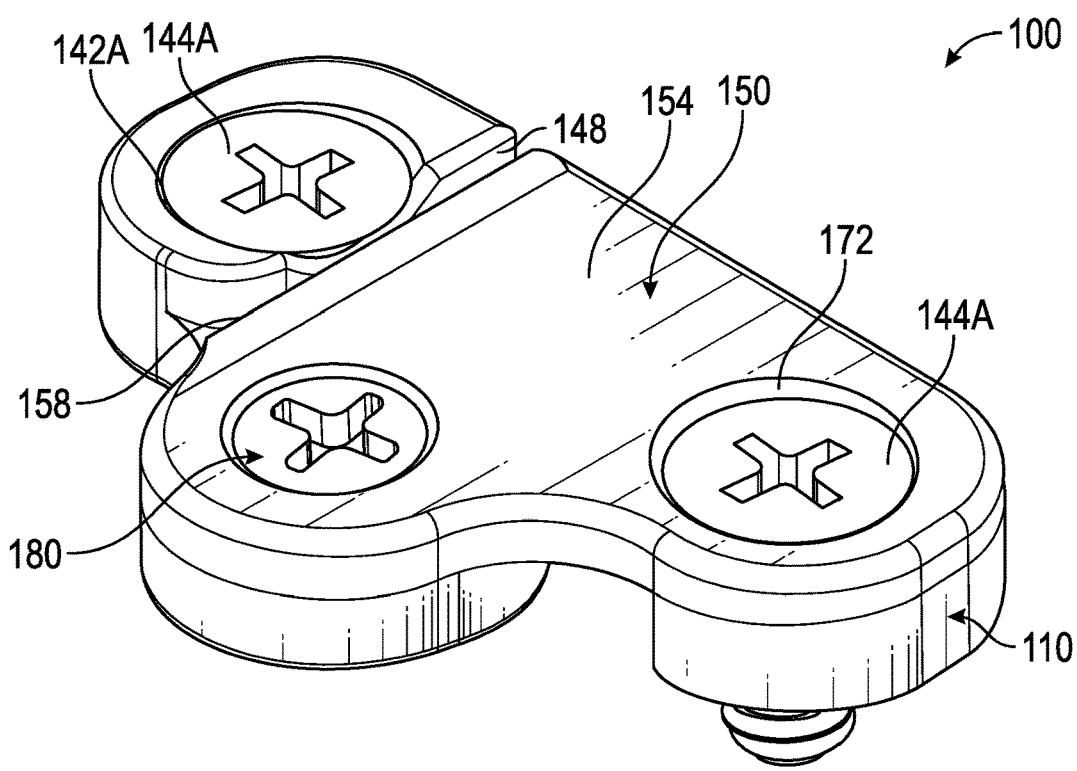
FIG. 2E is a rear perspective view showing the cranial lead fixation device of FIG. 2D in the second closed configuration.
Figure 2F:
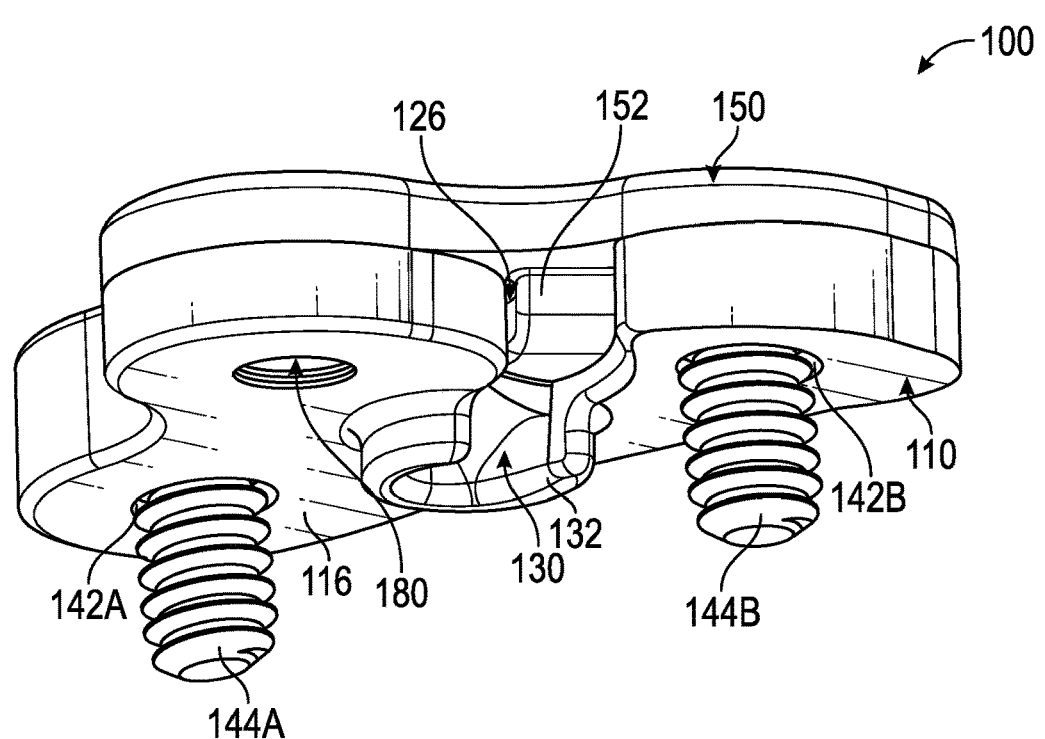
FIG. 2F is a rear underside perspective view showing the cranial lead fixation device of FIG. 2D in the second closed configuration.
Figure 2G:
FIG. 2G is an exploded view showing the cranial lead fixation device of FIG. 2D.

As shown, the cranial lead fixation device 100 includes a body 110 that affixes directly to the cranium 20, and a fixation mechanism 150 coupled along the body 110 that transitions the cranial lead fixation device 100 between the first open configuration of FIGS. 1A and 1B and the second closed configuration of FIGS. 1C and 1D and captures the medical device 10 within the fixation channel 102. FIGS. 2A-2C show the cranial lead fixation device 100 in the first open configuration without the cranium 20, FIGS. 2D-2E show the cranial lead fixation device 100 in the second closed configuration without the cranium 20, and FIG. 2G shows an exploded view of the cranial lead fixation device 100.

In some embodiments, the fixation channel 102 is collectively defined by the body 110 and the fixation mechanism 150; for instance, the body 110 can define a lower half 122 of the fixation channel 102 and the fixation mechanism 150 can define an upper half 162 of the fixation channel 102. The fixation mechanism 150 can be coupled along the body 110 by a connector mechanism 180, which in some embodiments is a hinge configuration that enables rotation of the fixation mechanism 150 relative to the body 110, however other configurations are contemplated and described in further embodiments herein.

Figure 1E:
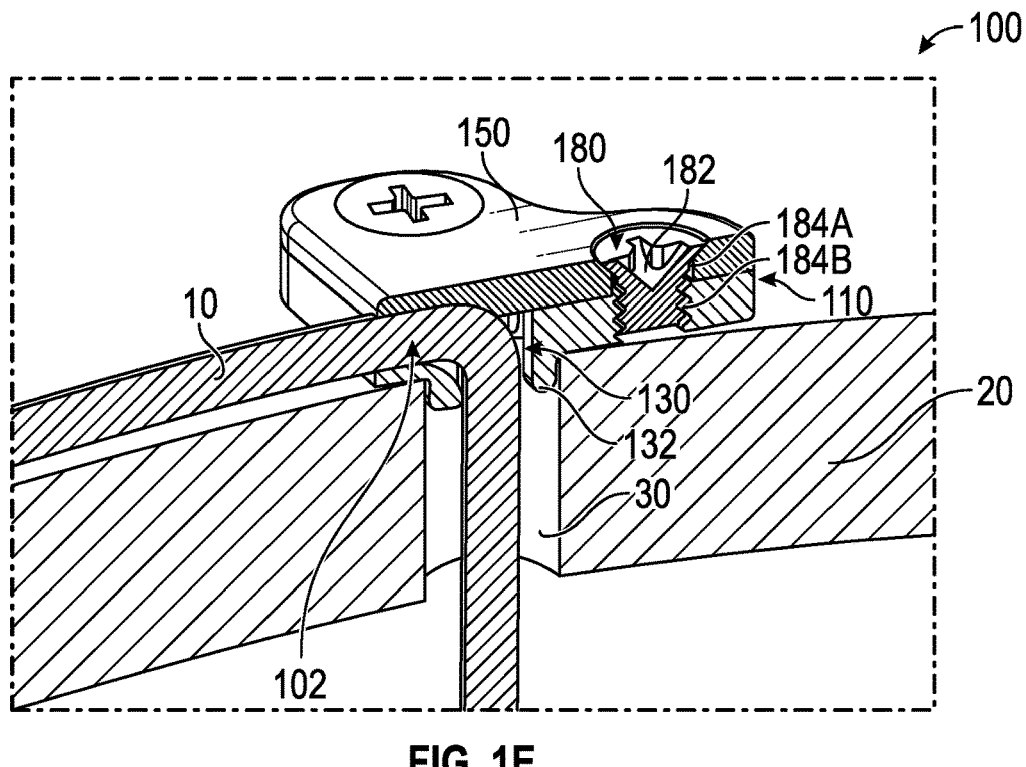
FIG. 1E is a cross-sectional perspective view showing the cranial lead fixation device of FIG. 1B taken along line 1E-1E of FIG. 1C.
Figure 1F:
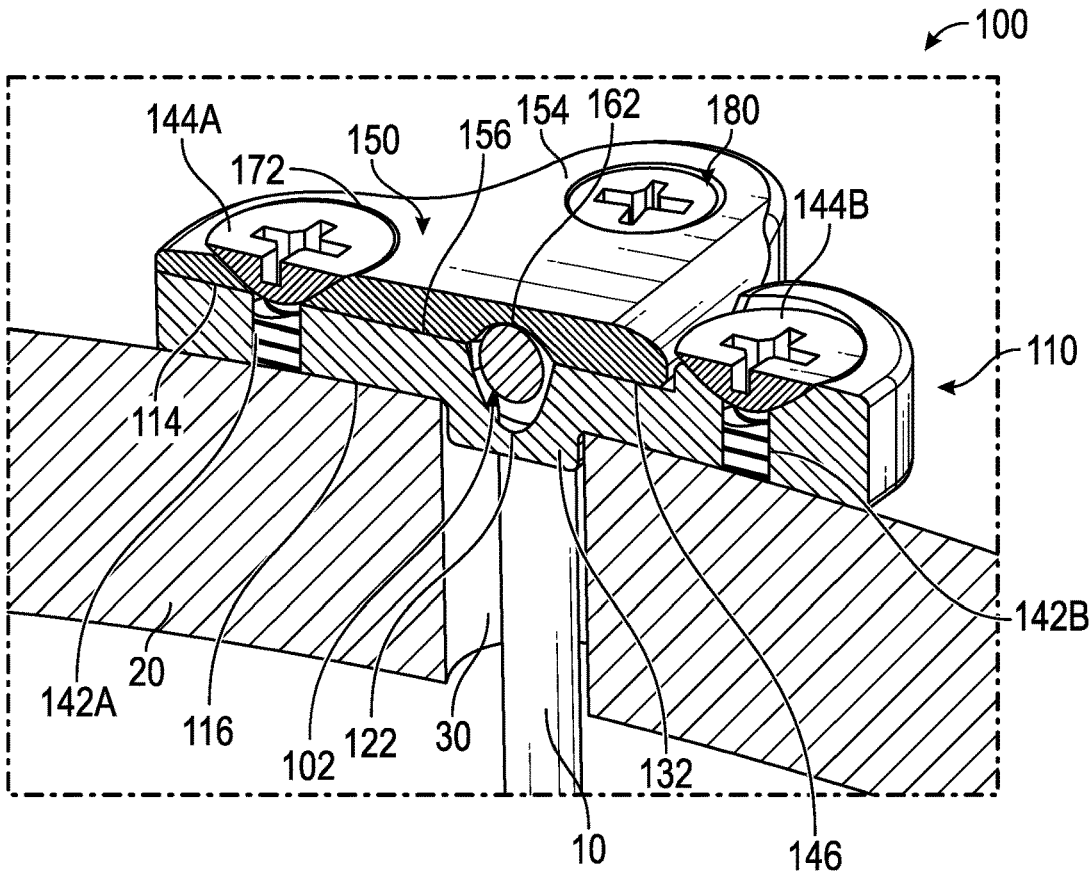
FIG. 1F is a cross-sectional perspective view showing the cranial lead fixation device of FIG. 1B taken along line 1F-1F of FIG. 1C.
Figure 3A:
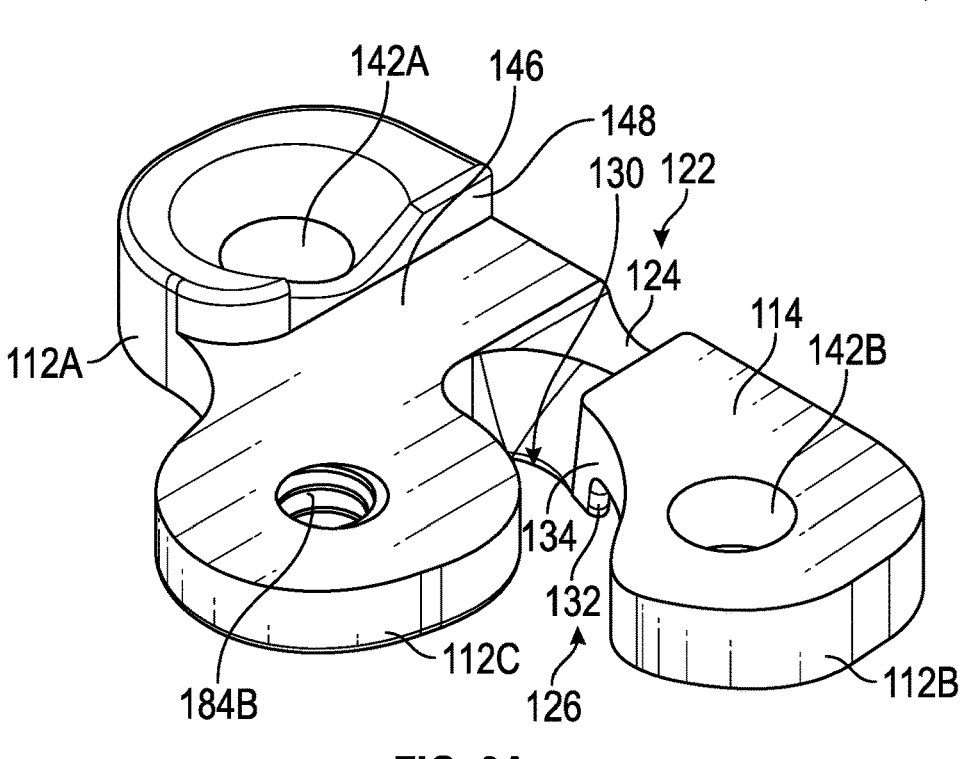
FIG. 3A is a front perspective view showing a body of the cranial lead fixation device of FIG. 2A.
Figure 3B:
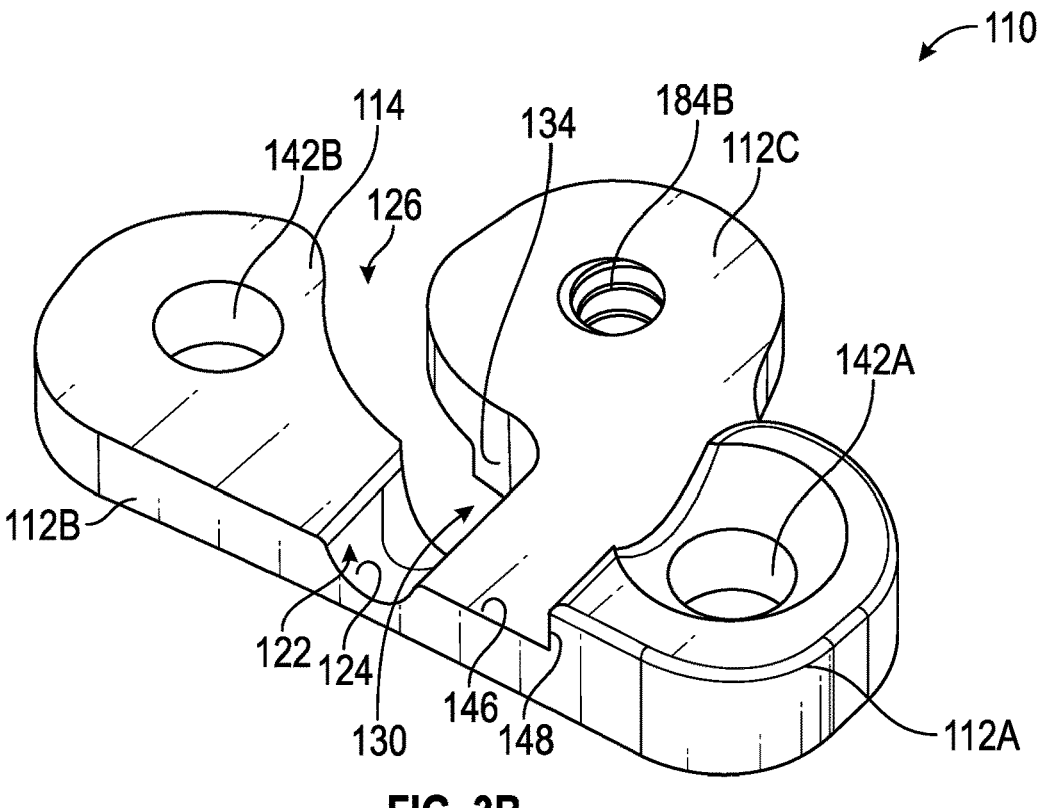
FIG. 3B is a rear perspective view showing the body of FIG. 3A.
Figure 3C:
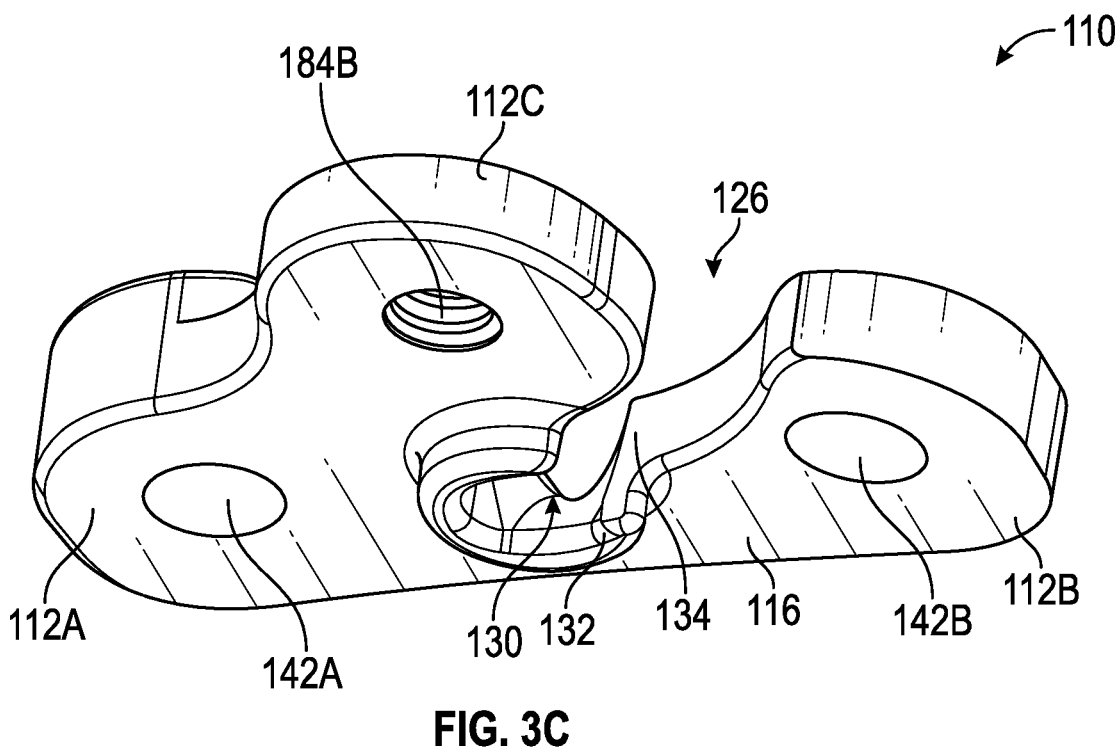
FIG. 3C is a rear underside perspective view showing the body of FIG. 3A.

The body 110 of the cranial lead fixation device 100 is illustrated in FIGS. 3A-3C. As shown, the body 110 can define a first wing 112A, a second wing 112B and a third wing 112C, and further defines an outer face 114 and an inner face 116. When the cranial lead fixation device 100 is positioned along the cranium 20 as shown in FIGS. 1E and 1F, the outer face 114 faces away from the cranium 20 and the inner face 116 is captured against the cranium 20; as such, in some embodiments, the inner face 116 is a concave surface that corresponds with a curvature of the cranium 20. Further, the body 110 defines a burr hole aperture 130 that aligns with the burr hole 30 and communicates with the fixation channel 102 such that, when captured at the cranial lead fixation device 100, the medical device 10 extends through the burr hole 30, the burr hole aperture 130 of the body 110, and finally through the fixation channel 102 as shown. In some embodiments, the body 110 circumferentially defines a burr hole lip 132 around the burr hole aperture 130 that extends below the inner face 116 for improved engagement with the burr hole 30.

In some embodiments, the body 110 includes an insertion channel 126 in communication with an open portion 134 of the burr hole aperture 130 that enables a practitioner to position the medical device 10 within the burr hole aperture 130 following fixation of the body 110 along the cranium 20; that is, the insertion channel 126 and open portion 134 eliminate the need to "thread" the medical device 10 through the burr hole aperture 130 prior to fixation of the body 110 along the cranium 20.

As further shown, the body 110 includes a plurality of cranial screw apertures (shown in the figures as cranial screw apertures 142A and 142B) configured to receive a plurality of cranial screws 144 for fixation of the body 110 to the cranium 20, including a first cranial screw aperture 142A configured to receive a first cranial screw 144A and a second cranial screw aperture 142B configured to receive a second cranial screw 144B. The body 110 can couple along the cranium 20 by insertion of the first cranial screw 144A into the first cranial screw aperture 142A and the cranium 20; note that the second cranial screw 144B can be installed after closure of the cranial lead fixation device 100 to secure the fixation mechanism 150 to the body 110 in the second closed configuration as will be discussed in greater detail below. In some embodiments, the first cranial screw aperture 142A is positioned along the first wing 112A of the body 110 and the second cranial screw aperture 142B is positioned along the second wing 112B of the body 110. As shown, the first cranial screw aperture 142A can be raised, providing a seat for the first cranial screw 144A, while the second cranial screw aperture 142B can be flat along the outer face 114 of the body 110 to enable rotation of fixation mechanism 150 from the between the first open configuration of FIGS. 1A, 1B and 2A-2C and the second closed configuration of FIGS. 1C, 1D and 2D-2F.

Figure 4A:
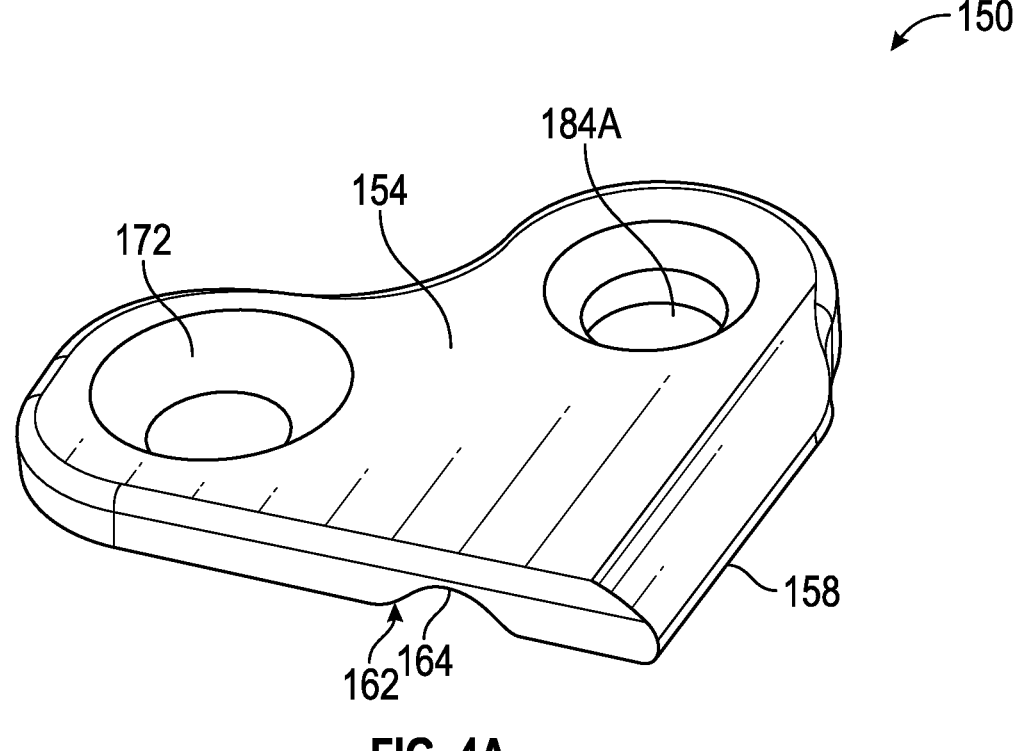
FIG. 4A is a front perspective view showing a fixation mechanism of the cranial lead fixation device of FIG. 2A.
Figure 4B:
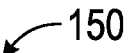
FIG. 4B is a below perspective view showing the fixation mechanism of FIG. 4A.
Figure 4B:
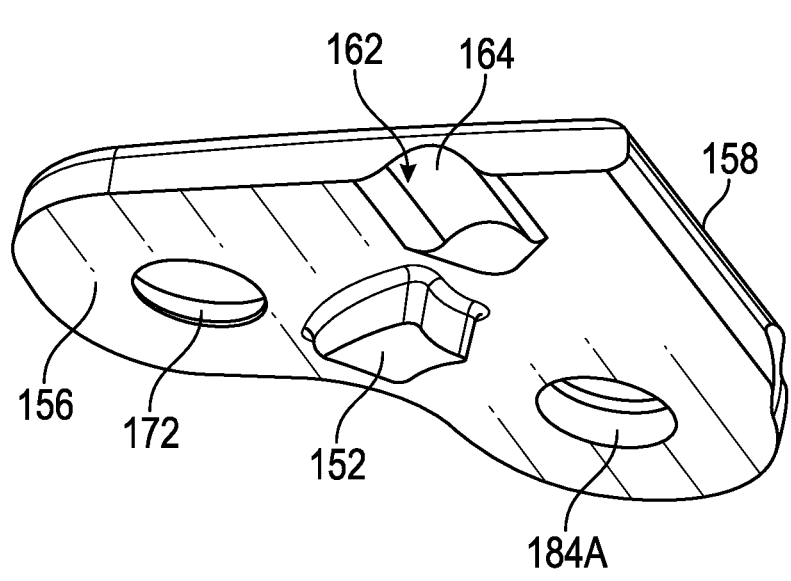
Figure 5A:
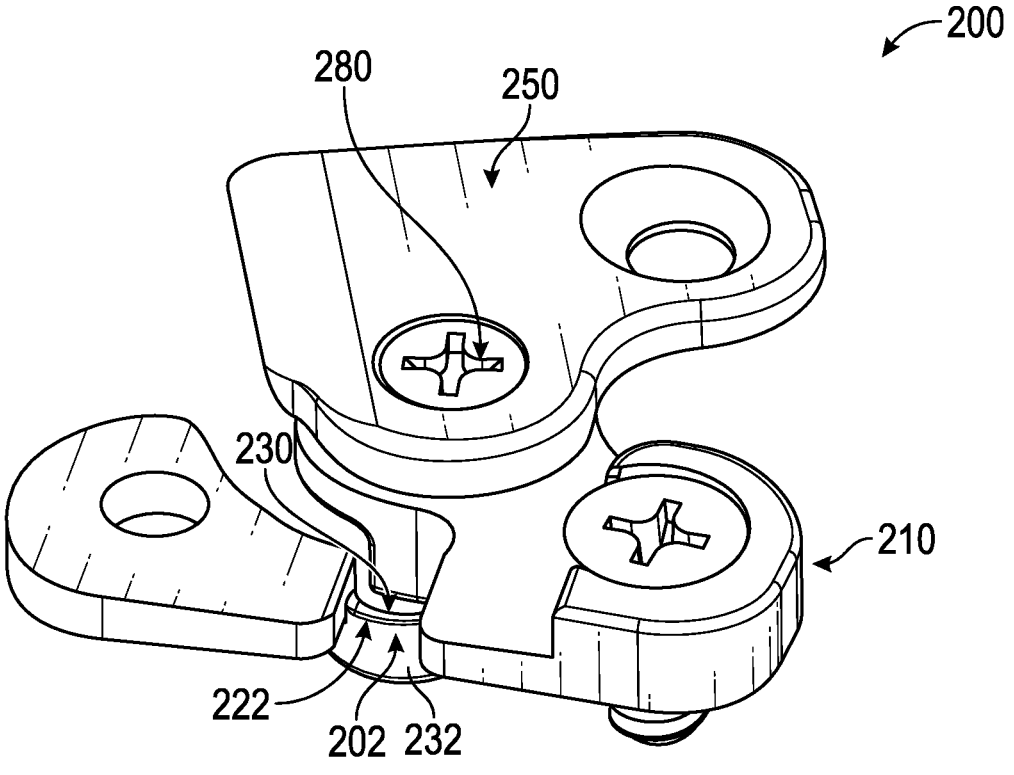
FIG. 5A is a front perspective view showing a second embodiment of a cranial lead fixation device in a first open configuration.
Figure 5B:
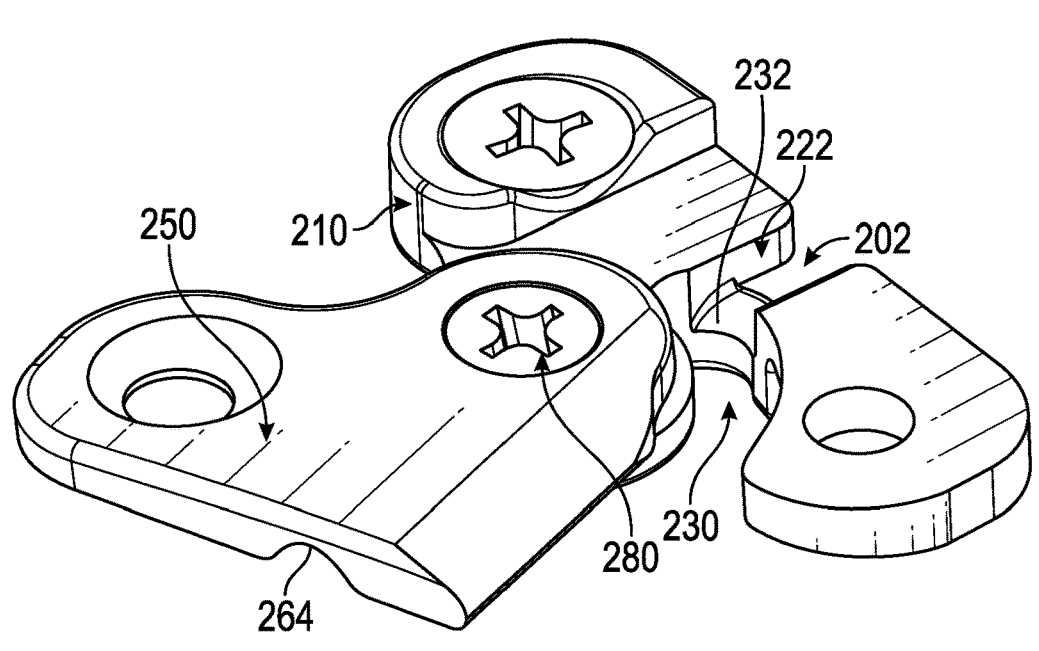
FIG. 5B is a rear perspective view showing the cranial lead fixation device of FIG. 5A in the first open configuration.
Figure 5C:
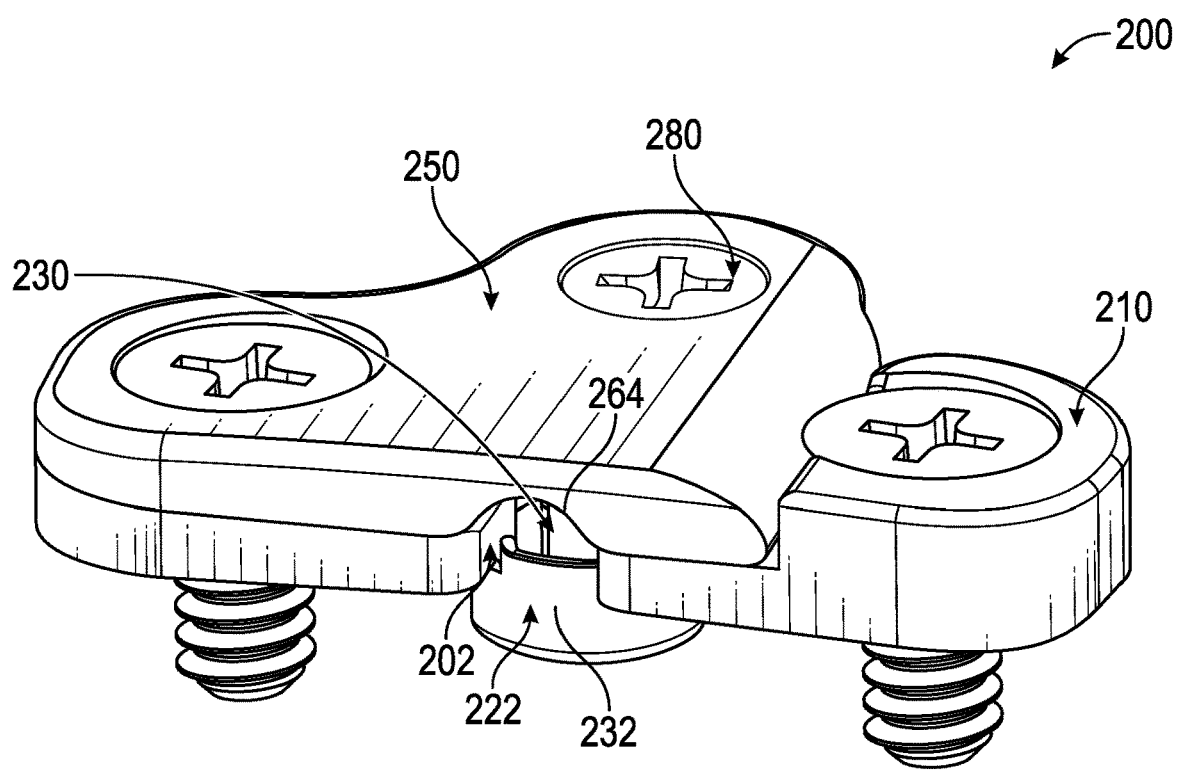
FIG. 5C is a front perspective view showing the cranial lead fixation device of FIG. 5A in a second closed configuration.
Figure 5D:
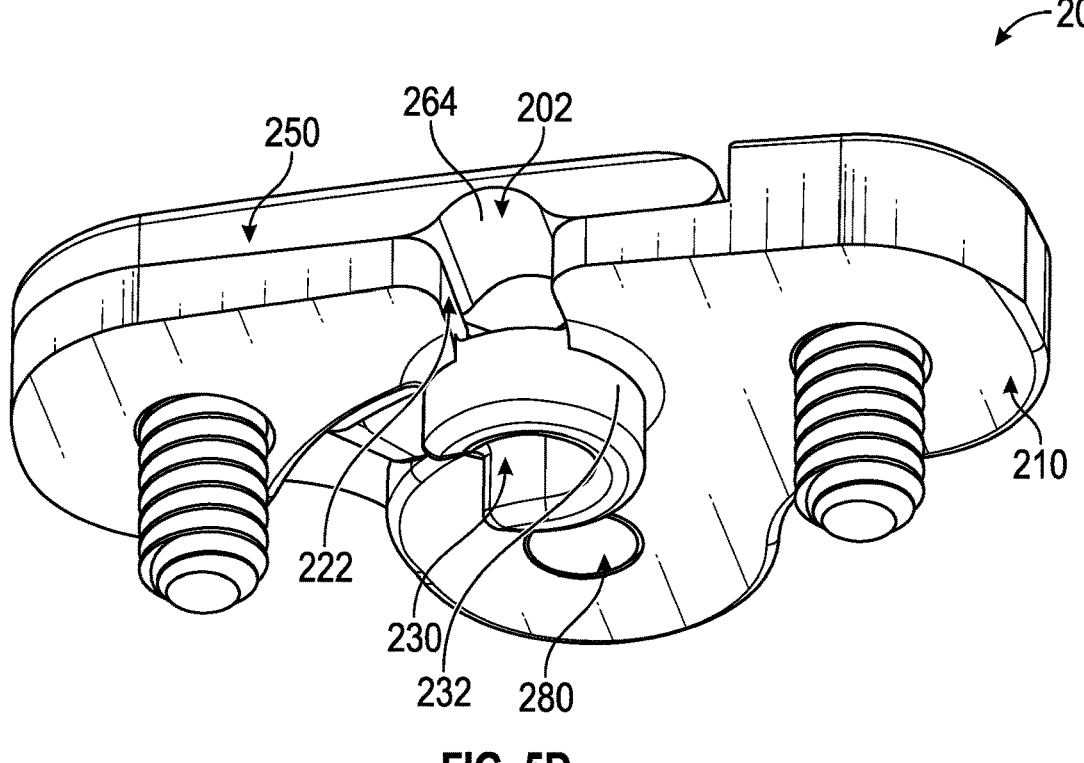
FIG. 5D is a rear perspective view showing the cranial lead fixation device of FIG. 5A in the second closed configuration.
Figure 6A:
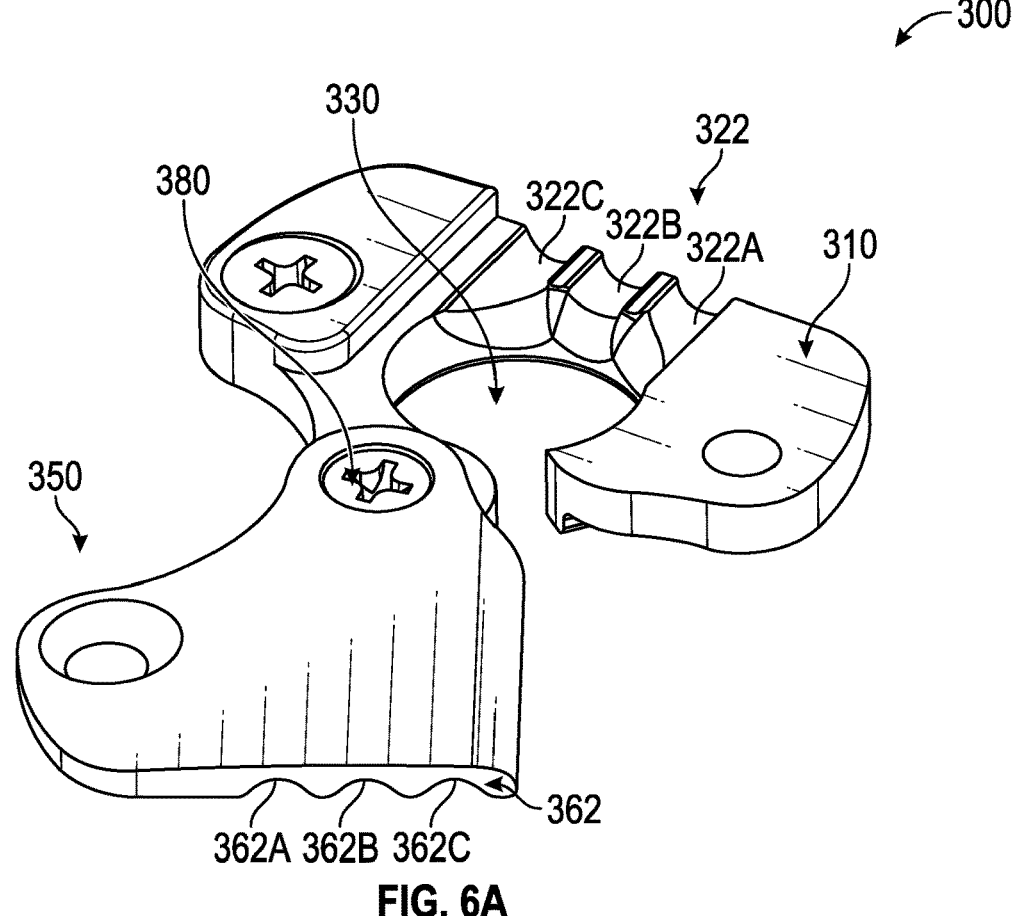
FIG. 6A is a front perspective view showing a third embodiment of a cranial lead fixation device in a first open configuration.
Figure 6B:
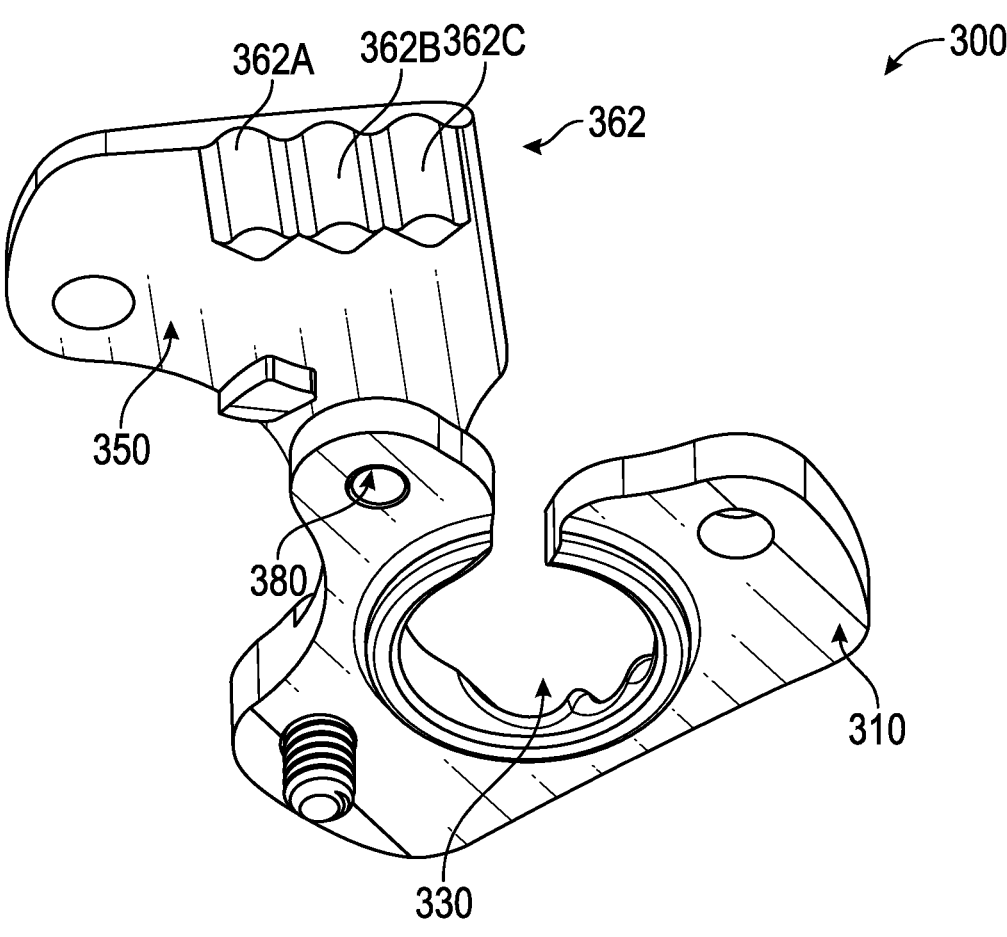
FIG. 6B is a rear perspective view showing the cranial lead fixation device of FIG. 6A in the first open configuration.
Figure 6C:
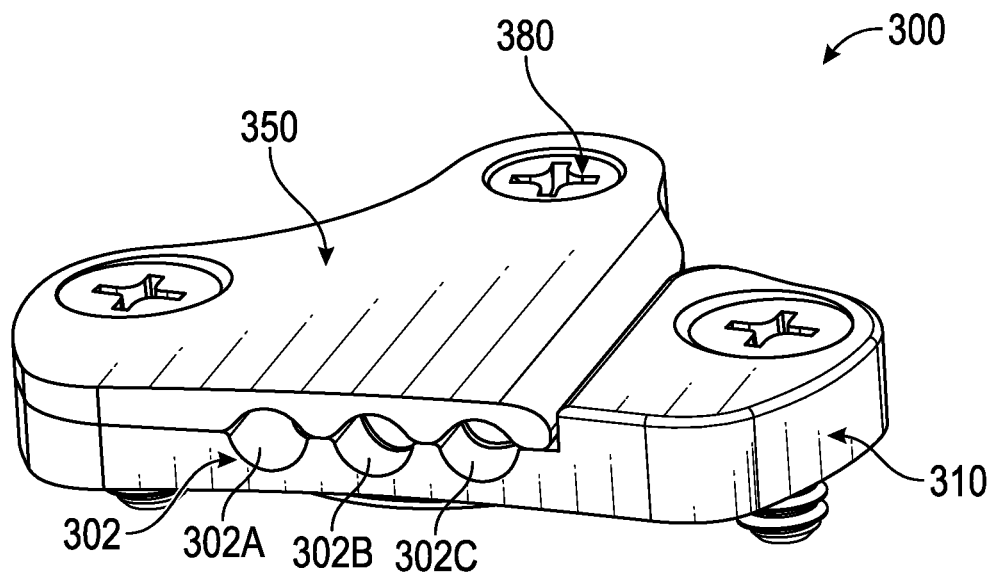
FIG. 6C is a front perspective view showing the cranial lead fixation device of FIG. 6A in a second closed configuration.
Figure 6D:
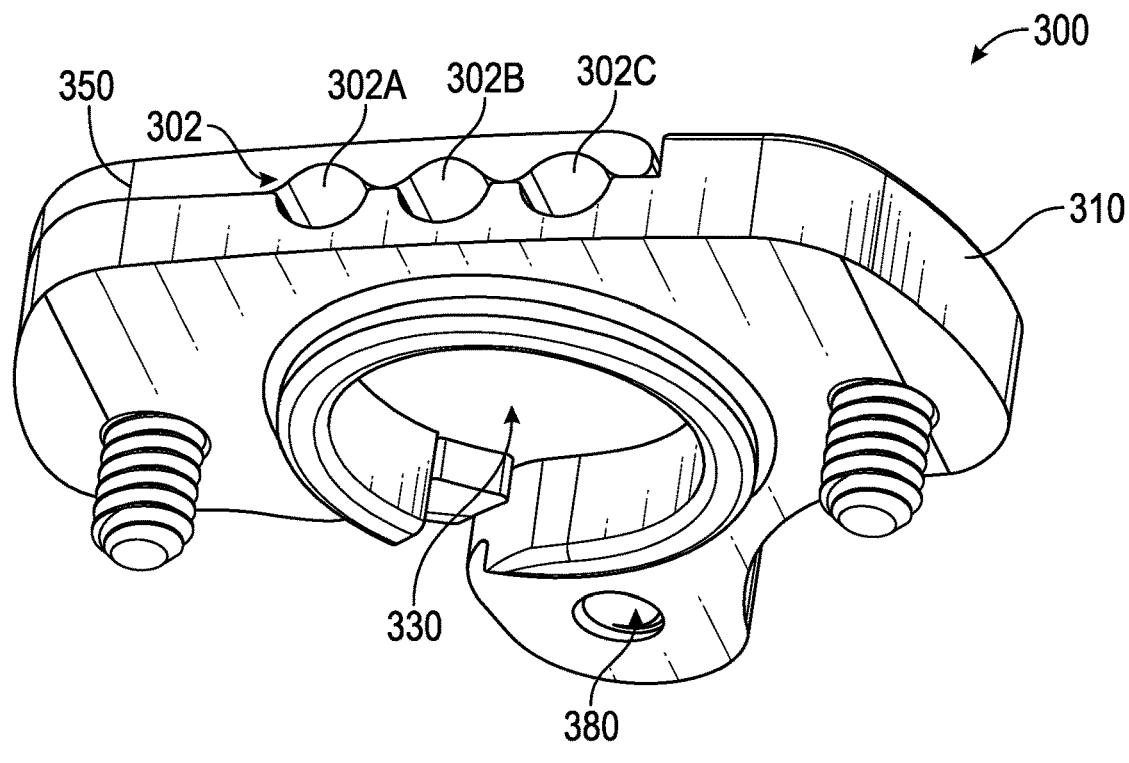
FIG. 6D is a rear perspective view showing the cranial lead fixation device of FIG. 6A in the second closed configuration.

The fixation mechanism 150 is shown alone in FIGS. 4A and 4B and defines a plate-like configuration. The fixation mechanism 150 couples with the body 110 and is operable for rotation, translation, or otherwise re-positioning between the first open configuration of FIGS. 1A, 1B and 2A-2C and the second closed configuration of FIGS. 1C, 1D and 2D-2F. In the embodiment shown, the fixation mechanism 150 is of a generally planar configuration. The outer face 114 of the body 110 includes a shelf 146 having a receiving abutment surface 148 configured to receive the fixation mechanism 150 as shown. The fixation mechanism 150 includes an outer face 154 and an inner face 156 such that when the fixation mechanism 150 is coupled along the body 110 and the body 110 is coupled along the cranium 20, the outer face 154 of the fixation mechanism 150 faces away from the body 110 and the cranium 20 and the inner face 156 faces the shelf 146 of the body 110 as shown. The fixation mechanism 150 includes a terminal abutment surface 158 that contacts the receiving abutment surface 148 of the shelf 146 of the body 110 when in the second closed configuration of FIGS. 1C, 1D and 2D-2F.

In a further aspect, the fixation mechanism 150 couples along the body 110 at the connector mechanism 180, which in the embodiment of FIG. 2G can include a pivot hinge 182 configured for insertion into a first hinge aperture 184A of the fixation mechanism 150 and a second hinge aperture 184B of the body 110; as shown, the second hinge aperture 184B of the body 110 can be positioned along the third wing 112C of the body 110 and can include a threading to prevent unintentional removal of the pivot hinge 182 from the body 110. Further, note that the pivot hinge 182 does not extend below the inner face 116 of the body 110 to avoid intruding on the cranium 20. The pivot hinge 182 provides a pivot point for rotation, translation, or otherwise re-positioning of the fixation mechanism 150 between the first open configuration of FIGS. 1A, 1B and 2A-2C and the second closed configuration of FIGS. 1C, 1D and 2D-2F.

The inner face 156 of the fixation mechanism 150 provides a protrusion 152 that engages within and closes off the insertion channel 126 of the body 110 when the cranial lead fixation device 100 is in the second closed configuration to prevent migration of the medical device 10 out of the burr hole aperture 130 of the body 110. In addition, the fixation mechanism 150 includes a second cranial screw seat 172 that aligns with the second cranial screw aperture 142B of the body 110 when the cranial lead fixation device 100 is in the second closed configuration of FIGS. 1C, 1D and 2D-2F.

As shown and as discussed above, fixation mechanism 150 forms the upper half 162 of the fixation channel 102 and the body 110 forms the lower half 122 of the fixation channel 102. In particular, the body 110 includes a fixation channel floor 124 along the outer face 114 that forms the lower half 122 of the fixation channel 102; similarly, the fixation mechanism 150 includes a fixation channel ceiling 164 along the inner face 156 that forms the upper half 162 of the fixation channel 102. When the cranial lead fixation device 100 is in the second closed configuration of FIGS. 1C, 1D and 2D-2F, the lower half 122 of the fixation channel 102 and the upper half 162 of the fixation channel 102 are aligned with one another to complete the fixation channel 102. Further, when in the second closed configuration, the fixation mechanism 150 can occlude the burr hole aperture 130 of the body 110.

As discussed above, the cranial lead fixation device 100 can be affixed directly to the cranium 20. In some embodiments, the cranial lead fixation device 100 can be configured in the first open configuration of FIGS. 1A, 1B and 2A-2C, and the body 110 can be coupled along the cranium 20 by insertion of the first cranial screw 144A into the first cranial screw aperture 142A and the cranium 20. At this time, the medical device 10 may already protrude from the burr hole 30 of the cranium 20; as such, the cranial lead fixation device 100 can be positioned over the burr hole 30 and the medical device 10 can be passed through the insertion channel 126 and into the burr hole aperture 130. Following coupling of the body 110 to the cranium 20 and following capture of the medical device 10 within the burr hole aperture 130 and the lower half 122 of the fixation channel 102, a practitioner can position the fixation mechanism 150 from the first open configuration of FIGS. 1A, 1B and 2A-2C to the second closed configuration of FIGS. 1C, 1D and 2D-2F to complete the fixation channel 102 such that the medical device 10 is captured within the fixation channel 102. Following closure of the cranial lead fixation device 100, a practitioner can insert the second cranial screw 144B through the second cranial screw seat 172 of the fixation mechanism 150, the second cranial screw aperture 142B of the body 110, and into the cranium 20. When fully assembled, the first cranial screw 144A nests within the first cranial screw aperture 142A and the second cranial screw 144B nests within the second cranial screw seat 172 as shown in FIGS. 2D and 2E.

With reference to FIGS. 5A-5D, a second embodiment of the cranial lead fixation device, designated as cranial lead fixation device 200, is similar to the cranial lead fixation device 100 of FIGS. 1A-4B and includes a fixation channel 202 collectively defined by a body 210 and a fixation mechanism 250 linked at a connector mechanism 280, where the body 210 includes a burr hole aperture 230 in communication with the fixation channel 202 for capture of a medical device (shown as medical device 10 in FIGS. 1A-1F with reference to cranial lead fixation device 100, but is similarly applicable for the cranial lead fixation device 200 of FIGS. 5A-5D). The cranial lead fixation device 200 is similarly configurable in a first open configuration shown in FIGS. 5A and 5B and a second closed configuration shown in FIGS. 5C and 5D. When in the second closed configuration, the fixation mechanism 250 can occlude the burr hole aperture 230 of the body 210.

In contrast with the cranial lead fixation device 100 of FIGS. 1A-4B, a lower half 222 of the fixation channel 202 is open (eliminating the fixation channel floor 124 of FIGS. 3A and 3B) along the body 210 to reduce an overall vertical profile or "thickness" of the cranial lead fixation device 200. To maintain the medical device within the burr hole aperture 230, the body 210 circumferentially defines a burr hole lip 232 around the burr hole aperture 230 and at a junction of the fixation channel 202 and the burr hole aperture 230 as shown. This modification enables the medical device 10 to be positioned between the cranium (shown in FIGS. 1B-1F as cranium 20) and a fixation channel ceiling 264 of the fixation mechanism 250 of the cranial lead fixation device 200.

A third embodiment of the cranial lead fixation device (designated as cranial lead fixation device 300) is shown in FIGS. 6A-6D. The cranial lead fixation device 300 is similar to the cranial lead fixation device 100 of FIGS. 1A-4B and includes a fixation channel 302 collectively defined by a body 310 and a fixation mechanism 350 linked at a connector mechanism 380, where the body 310 includes a burr hole aperture 330 in communication with the fixation channel 302 for capture of a medical device (shown as medical device 10 in FIGS. 1A-1F with reference to cranial lead fixation device 100, but is similarly applicable for the cranial lead fixation device 300 of FIGS. 6A-6D). The cranial lead fixation device 300 is similarly configurable in a first open configuration shown in FIGS. 6A and 6B and a second closed configuration shown in FIGS. 6C and 6D. Similarly, when in the second closed configuration, the fixation mechanism 350 can occlude the burr hole aperture 330 of the body 310.

In contrast with the cranial lead fixation device 100 of FIGS. 1A-4B, the fixation channel 302 includes a plurality of sub-channels (e.g., sub-channels 302A-302C) for passage of more than one medical device between the burr hole aperture 330 and the fixation channel 302. In particular, the body 310 includes a lower half 322 (e.g., lower halves 322A-322C) of the fixation channel 302 and the fixation mechanism 350 includes an upper half 362 (e.g., upper halves 362A-362C) of the fixation channel 302. Further, as shown, the burr hole aperture 330 is wider in diameter than that of the burr hole aperture 130 of FIGS. 3A and 3B and the burr hole aperture 230 of FIGS. 5A and 5B to accommodate multiple medical devices.

Figure 7A:
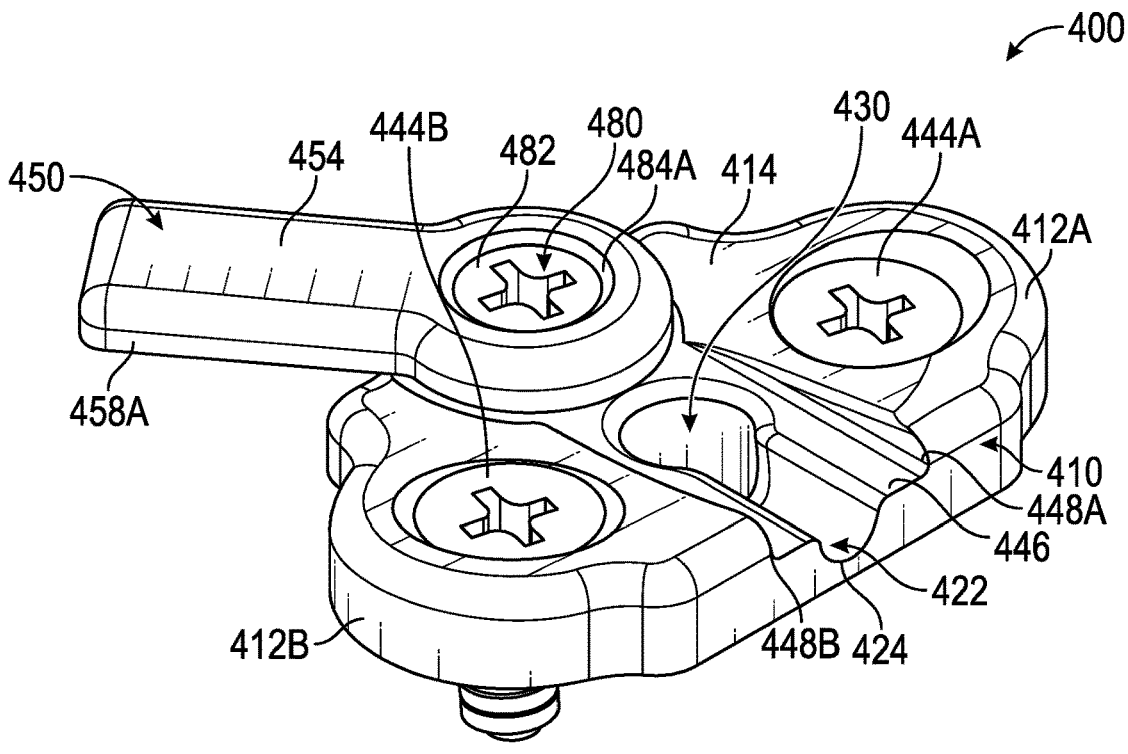
FIG. 7A is a front perspective view showing a fourth embodiment of a cranial lead fixation device in a first open configuration.
Figure 7B:
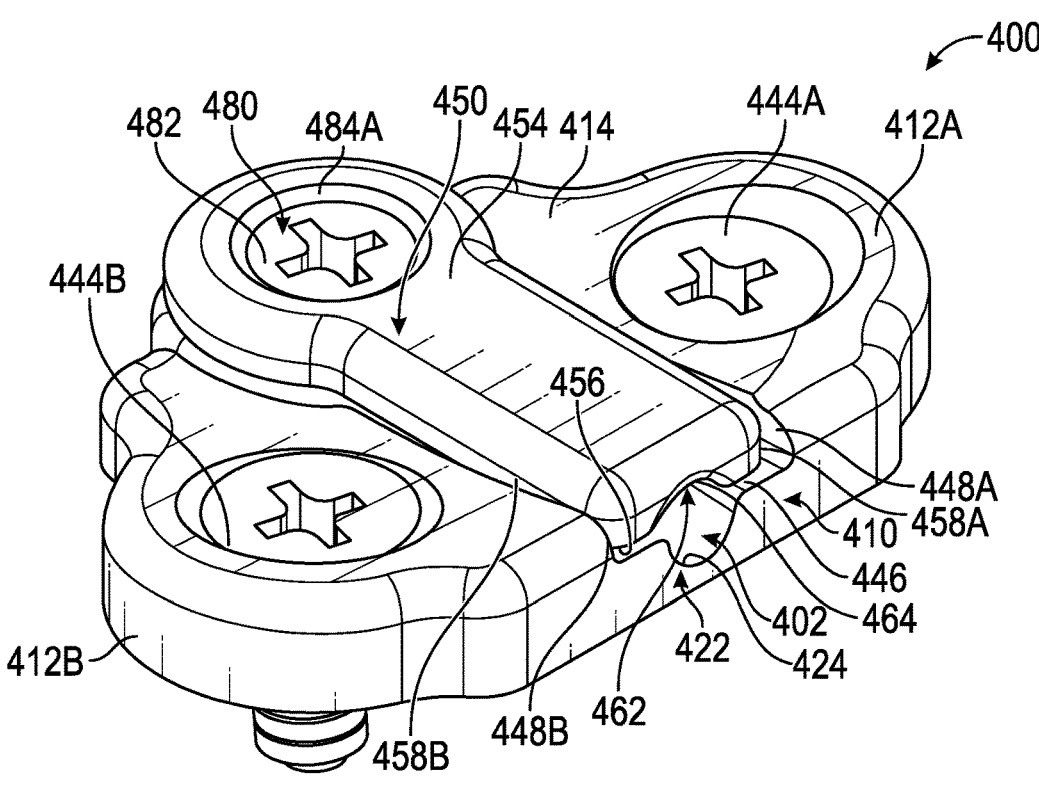
FIG. 7B is a front perspective view showing the cranial lead fixation device of FIG. 7A in a second closed configuration.
Figure 7C:
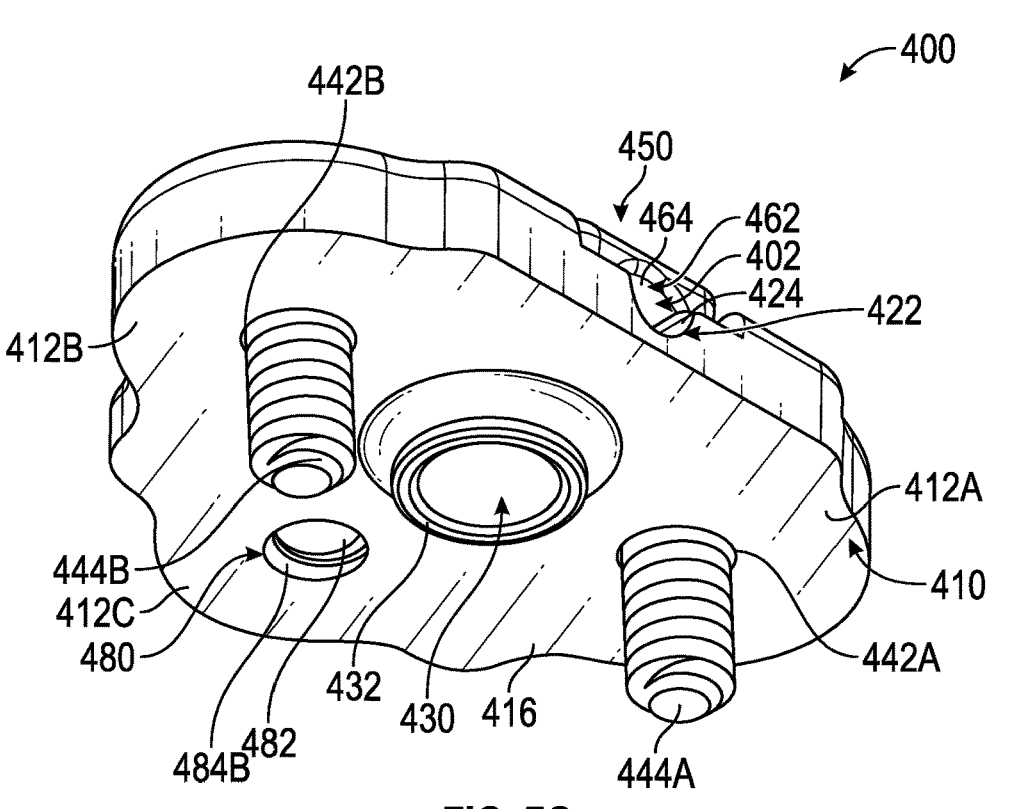
FIG. 7C is an underside perspective view showing the body of FIG. 7A.

FIGS. 7A-7C show a fourth embodiment of the cranial lead fixation device (designated as cranial lead fixation device 400). As shown, the cranial lead fixation device 400 is operable to assume a first open configuration (FIG. 7A) and a second closed configuration (FIG. 7B). Further, the cranial lead fixation device 400 includes a fixation channel 402 for receipt of a medical device (shown as medical device 10 in FIGS. 1A-1F with reference to cranial lead fixation device 100, but is similarly applicable for the cranial lead fixation device 400 of FIGS. 7A-7C). When the cranial lead fixation device 400 is in the first open configuration, the fixation channel 402 is "open" and operable to accept the medical device. When the cranial lead fixation device 400 is in the second "closed" configuration, the fixation channel 402 captures the medical device such that the medical device is prevented from being removed or otherwise pulled away from the cranium (shown in FIGS. 1B-1F as cranium 20).

As shown, the cranial lead fixation device 400 includes a body 410 that affixes directly to the cranium, and a fixation mechanism 450 coupled along the body 410 that transitions the cranial lead fixation device 400 between the first open configuration of FIG. 7A and the second closed configuration of FIG. 7B and captures the medical device within the fixation channel 402. In contrast to the cranial lead fixation device 100 of FIGS. 1A-2G, 4A and 4B, the fixation mechanism 450 can be of an arm-like configuration. In some embodiments, the fixation channel 402 is collectively defined by the body 410 and the fixation mechanism 450; for instance, the body 410 can define a lower half 422 of the fixation channel 402 and the fixation mechanism 450 can define an upper half 462 of the fixation channel 402. The fixation mechanism 450 can be coupled along the body 410 by a connector mechanism 480, which in some embodiments is a hinge configuration that enables rotation of the fixation mechanism 450 relative to the body 410, however other configurations are contemplated and described in further embodiments herein.

The body 410 of the cranial lead fixation device 400 can define a first wing 412A, a second wing 412B and a third wing 412C, and further defines an outer face 414 and an inner face 416. When the cranial lead fixation device 400 is positioned along the cranium, the outer face 414 faces away from the cranium and the inner face 416 is captured against the cranium; as such, in some embodiments, the inner face 416 is a concave surface that corresponds with a curvature of the cranium. Further, the body 410 defines a burr hole aperture 430 that aligns with the burr hole (shown in FIGS. 1E and 1F as burr hole 30) and communicates with the fixation channel 402 such that, when captured at the cranial lead fixation device 400, the medical device extends through the burr hole, the burr hole aperture 430 of the body 410, and finally through the fixation channel 402 as shown. In some embodiments, as shown in FIG. 7C, the body 410 body 410 circumferentially defines a burr hole lip 432 around the burr hole aperture 430 that extends below the inner face 416 for improved engagement with the burr hole.

As further shown, the body 410 includes a plurality of cranial screw apertures (shown in the figures as cranial screw apertures 442A and 442B) configured to receive a plurality of cranial screws (shown in the figures as cranial screws 444A and 444B) for fixation of the body 410 to the cranium, including a first cranial screw aperture 442A configured to receive a first cranial screw 444A and a second cranial screw aperture 442B configured to receive a second cranial screw 444B. The body 410 can couple along the cranium by insertion of the first cranial screw 444A into the first cranial screw aperture 442A and the cranium and by insertion of the second cranial screw 444B into the second cranial screw aperture 442B and the cranium. In some embodiments, the first cranial screw aperture 442A is positioned along the first wing 412A of the body 410 and the second cranial screw aperture 442B is positioned along the second wing 412B of the body 410. As shown, the first cranial screw aperture 442A and the second cranial screw aperture 442B can be raised, respectively providing a seat for the first cranial screw 444A and the second cranial screw 444B.

As discussed and as shown, the fixation mechanism 450 is coupled with the body 410 and is operable for rotation, translation, or otherwise re-positioning between the first open configuration of FIG. 7A and the second closed configuration of FIG. 7B. The outer face 414 of the body 410 includes a shelf 446 having a first receiving abutment surface 448A and a second receiving abutment surface 448B configured to receive the fixation mechanism 450 as shown, although note that in this embodiment, the shelf 446 does not intrude into the first wing 412A or the second wing 412B in contrast with the shelf 146 of the cranial lead fixation device 100 of FIGS. 1A-4B due to the arm-like configuration of the fixation mechanism 450.

The fixation mechanism 450 includes an outer face 454 and an inner face 456 such that when the fixation mechanism 450 is coupled along the body 410 and the body 410 is coupled along the cranium, the outer face 454 of the fixation mechanism 450 faces away from the body 410 and the cranium and the inner face 456 faces the shelf 446 of the body 410 as shown. The fixation mechanism 450 includes a first terminal abutment surface 458A that contacts the first receiving abutment surface 448A of the shelf 446 of the body 410 and a second terminal abutment surface 458B that contacts the second receiving abutment surface 448B of the shelf 446 of the body 410 when in the second closed configuration of FIG. 7B. In a further aspect, the fixation mechanism 450 is coupled along the body 410 at the connector mechanism 480, which in the embodiment shown can include a pivot hinge 482 configured for insertion into a first hinge aperture 484A of the fixation mechanism 450 and a second hinge aperture 484B of the body 410; as shown, the second hinge aperture 484B of the body 410 can be positioned along the third wing 412C of the body 410 and can include a threading to prevent unintentional removal of the pivot hinge 482 from the body 410. Further, note that the pivot hinge 482 does not extend below the inner face 416 of the body 410 to avoid intruding on the cranium. The pivot hinge 482 provides a pivot point for rotation, translation, or otherwise re-positioning of the fixation mechanism 450 between the first open configuration of FIG. 7A and the second closed configuration of FIG. 7B.

As shown and as discussed above, the fixation mechanism 450 forms the upper half 462 of the fixation channel 402 and the body 410 forms the lower half 422 of the fixation channel 402. In particular, the body 410 includes a fixation channel floor 424 along the outer face 414 that forms the lower half 422 of the fixation channel 402; similarly, the fixation mechanism 450 includes a fixation channel ceiling 464 along the inner face 456 that forms the upper half 462 of the fixation channel 402. When the cranial lead fixation device 400 is in the second closed configuration of FIG. 7B, the lower half 422 of the fixation channel 402 and the upper half 462 of the fixation channel 402 are aligned with one another to complete the fixation channel 402. Similarly, when in the second closed configuration, the fixation mechanism 450 can occlude the burr hole aperture 430 of the body 410.

As discussed above, the cranial lead fixation device 400 can be affixed directly to the cranium. In some embodiments, the cranial lead fixation device 400 can be configured in the first open configuration of FIG. 7A, and the body 410 can be coupled along the cranium by insertion of the first cranial screw 444A into the first cranial screw aperture 442A and the cranium and insertion of the second cranial screw 444B into the second cranial screw aperture 442B and the cranium, where the exposed portion of the medical device can be "threaded" through the burr hole aperture 430 during placement of the body 410 along the cranium. Following coupling of the body 410 to the cranium and following capture of the medical device within the burr hole aperture 430 and the lower half 422 of the fixation channel 402, a practitioner can position the fixation mechanism 450 from the first open configuration of FIG. 7A and into the second closed configuration of FIG. 7B to complete the fixation channel 402 such that the medical device is enclosed within the fixation channel 402.

Figure 8:
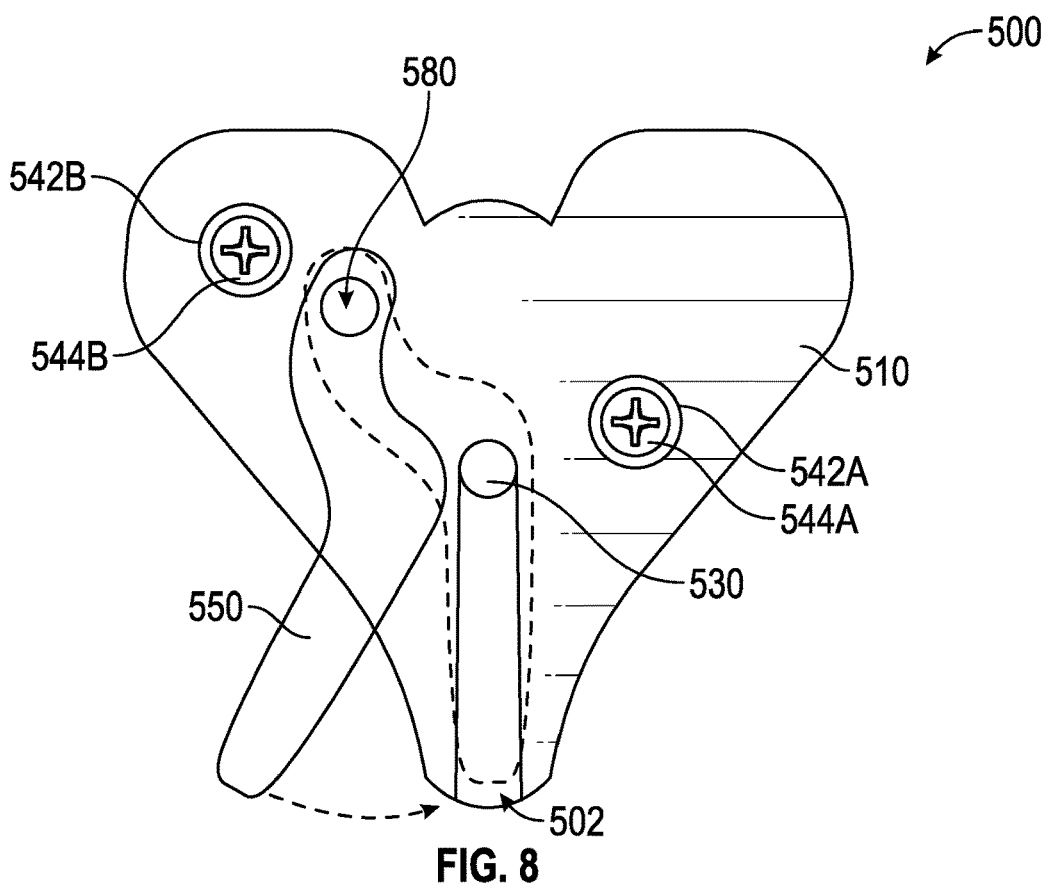
FIG. 8 is a top plan view showing a fifth embodiment of a cranial lead fixation device having a fixation mechanism moveable relative to the body from a first open configuration (shown in phantom) to a second closed configuration.

FIG. 8 shows a fifth embodiment of the cranial lead fixation device, designated as cranial lead fixation device 500, that is similar to the cranial lead fixation device 400 and includes a fixation channel 502 collectively defined by a body 510 and a fixation mechanism 550 linked at a connector mechanism 580, where the body 510 includes a burr hole aperture 530 in communication with the fixation channel 502 for capture of a medical device (shown as medical device 10 in FIGS. 1A-1F with reference to cranial lead fixation device 100, but is similarly applicable for the cranial lead fixation device 500 of FIG. 8). The cranial lead fixation device 500 is similarly configurable in a first open configuration and a second closed configuration (shown in phantom). When in the second closed configuration, the fixation mechanism 550 can occlude the burr hole aperture 530 of the body 510.

In contrast to the cranial lead fixation device 400, the fixation mechanism 550 can include a curve as shown, with the connector mechanism 580 being positioned off-center. Similarly, the fixation mechanism 550 can be rotated about the connector mechanism 580 as shown to complete the fixation channel 502 and capture the medical device therein. The body 510 can include a first cranial screw aperture 542A and a second cranial screw aperture 542B for respective receipt of a first cranial screw 544A and a second cranial screw 544B; as shown, the first cranial screw aperture 542A and a second cranial screw aperture 542B can be asymmetrically distributed along the body 510.

Figure 9:
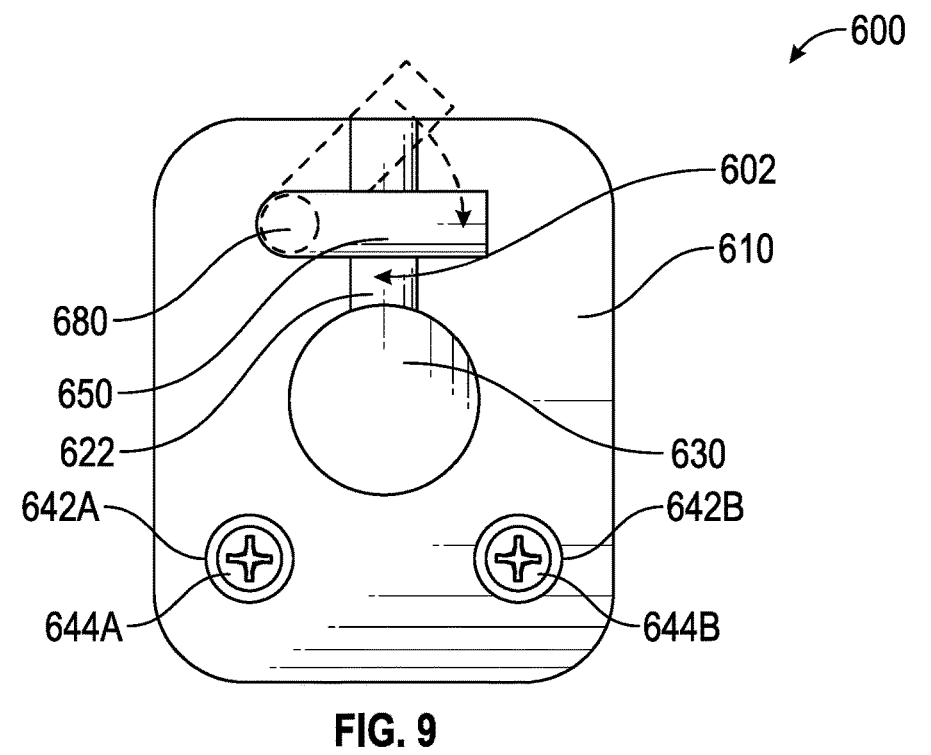
FIG. 9 is a top plan view showing a sixth embodiment of a cranial lead fixation device having a fixation mechanism moveable relative to the body from a first open configuration (shown in phantom) to a second closed configuration and oriented perpendicular to a fixation channel of the cranial lead fixation device.

FIG. 9 shows a sixth embodiment of the cranial lead fixation device, designated as cranial lead fixation device 600, that is similar to the cranial lead fixation device 400. The cranial lead fixation device 600 includes a fixation channel 602 collectively defined by a body 610 and a fixation mechanism 650 linked at a connector mechanism 680, where the body 610 includes a burr hole aperture 630 in communication with the fixation channel 602 for capture of a medical device (shown as medical device 10 in FIGS. 1A-1F with reference to cranial lead fixation device 100, but is similarly applicable for the cranial lead fixation device 600 of FIG. 9). The cranial lead fixation device 600 is similarly configurable in a first open configuration (shown in phantom) and a second closed configuration. As shown, the body 610 includes a lower half 622 of the fixation channel 602 or can optionally include the entirety of the fixation channel 602. The body 610 can include a first cranial screw aperture 642A and a second cranial screw aperture 642B for respective receipt of a first cranial screw 644A and a second cranial screw 644B; as shown, the first cranial screw aperture 642A and a second cranial screw aperture 642B can be symmetrically or asymmetrically distributed along the body 610.

In contrast to the cranial lead fixation device 400 of FIGS. 7A-7C and the cranial lead fixation device 500 of FIG. 8, the fixation mechanism 650 can be oriented perpendicular to the fixation channel 602 to encapsulate the medical device against the fixation channel 602 of the body 610, with the connector mechanism 680 being positioned adjacent to the fixation channel 602 as shown. Similarly, the fixation mechanism 650 can be rotated about the connector mechanism 680 to transition the cranial lead fixation device 600 between the first open configuration and the second closed configuration and capture the medical device within the fixation channel 602.

A seventh embodiment of the cranial lead fixation device (designated as cranial lead fixation device 700) is shown in FIGS. 10A-12B for capturing and securing a medical device (shown as medical device 10 in FIGS. 1A-1F with reference to cranial lead fixation device 100, but is similarly applicable for the cranial lead fixation device 700 of FIGS. 10A-12B) within a burr hole formed within a cranium (shown in FIGS. 1B-1F as cranium 20 and burr hole 30).

Figure 10A:
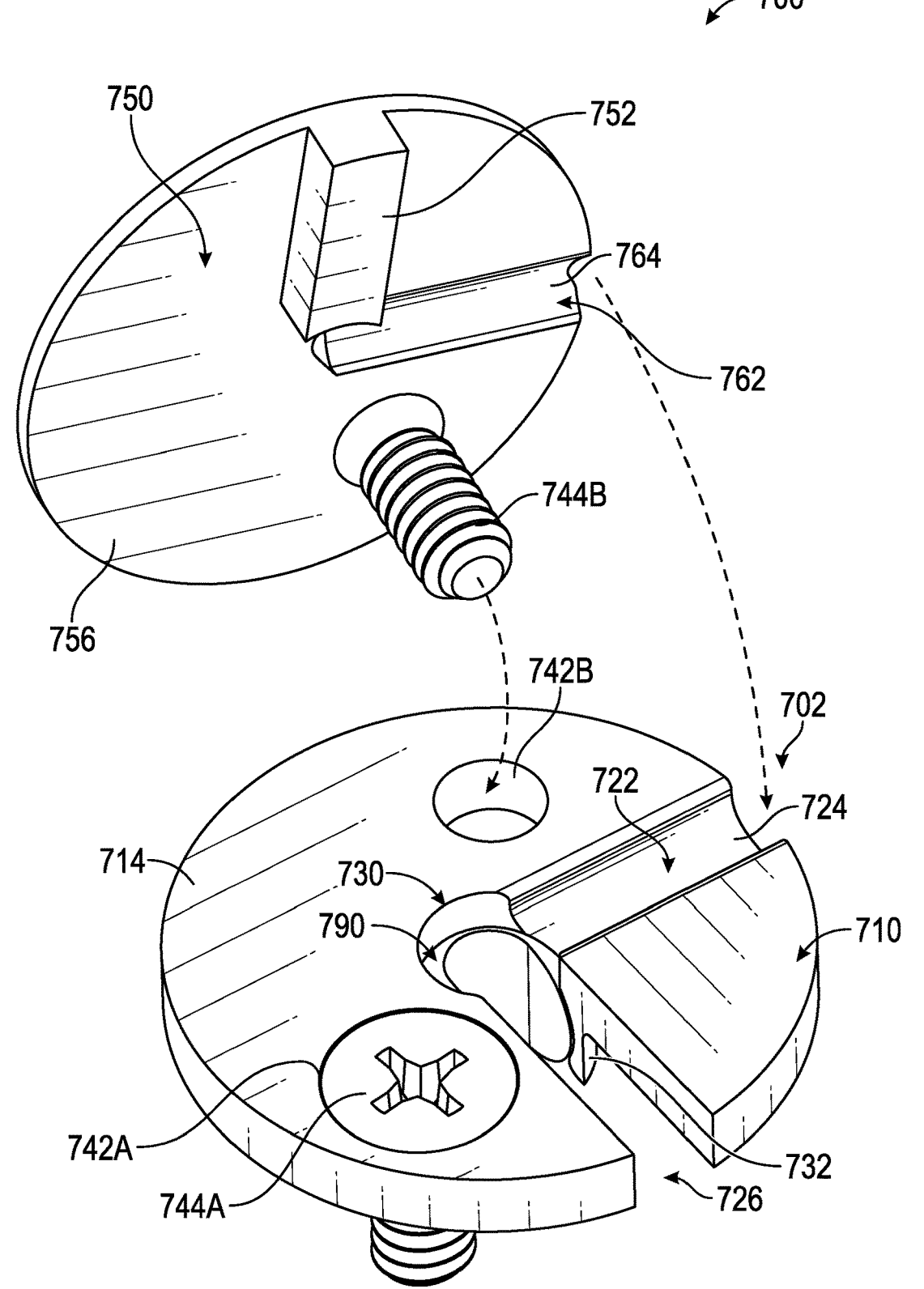
FIG. 10A is a front perspective view showing a seventh embodiment of a cranial lead fixation device in a first open configuration.
Figure 10B:
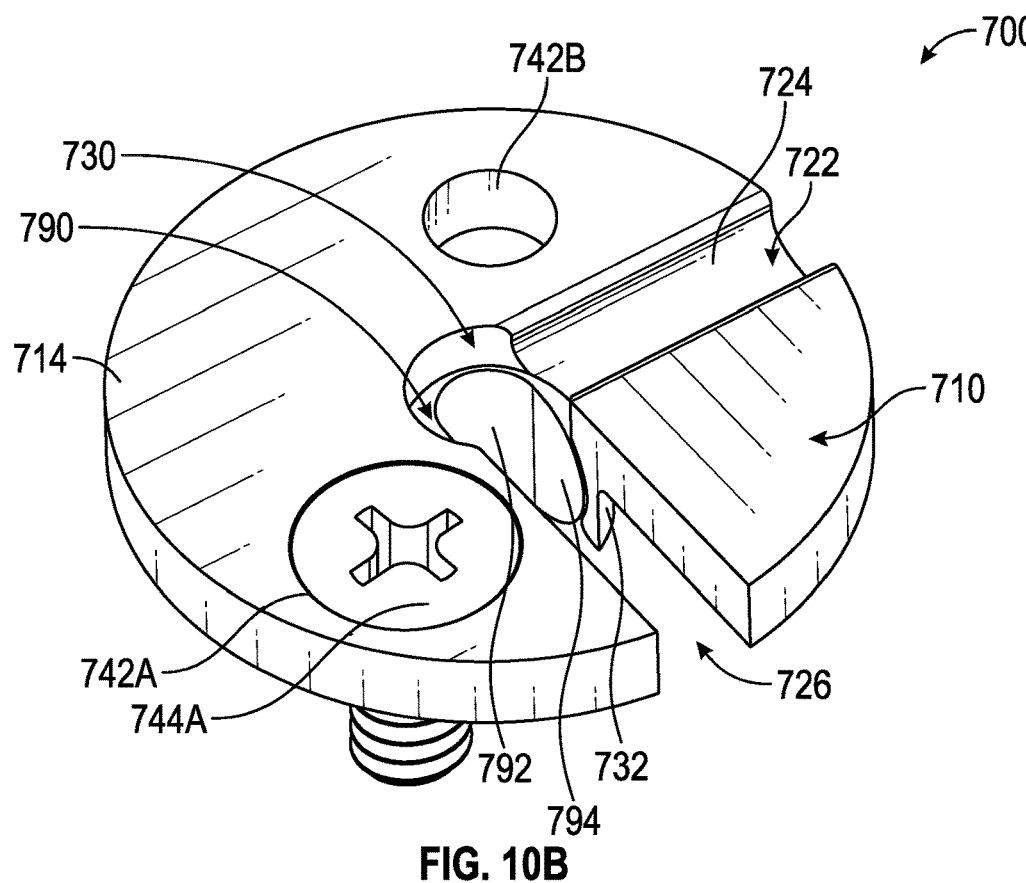
FIG. 10B is a front perspective view showing a base of the cranial lead fixation device of FIG. 10A and having a ball oriented in a first vertical configuration.
Figure 10C:
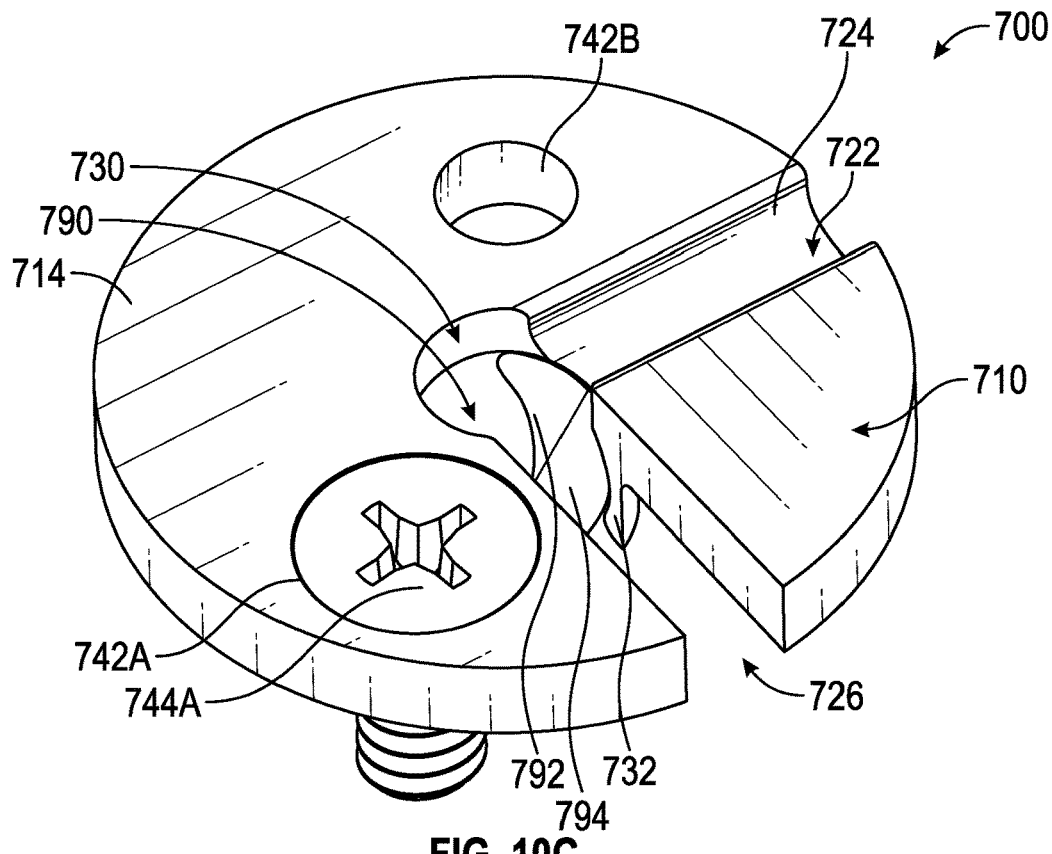
FIG. 10C is a front perspective view showing the base of FIG. 10B and having a ball oriented in a second angled vertical configuration.
Figure 10D:
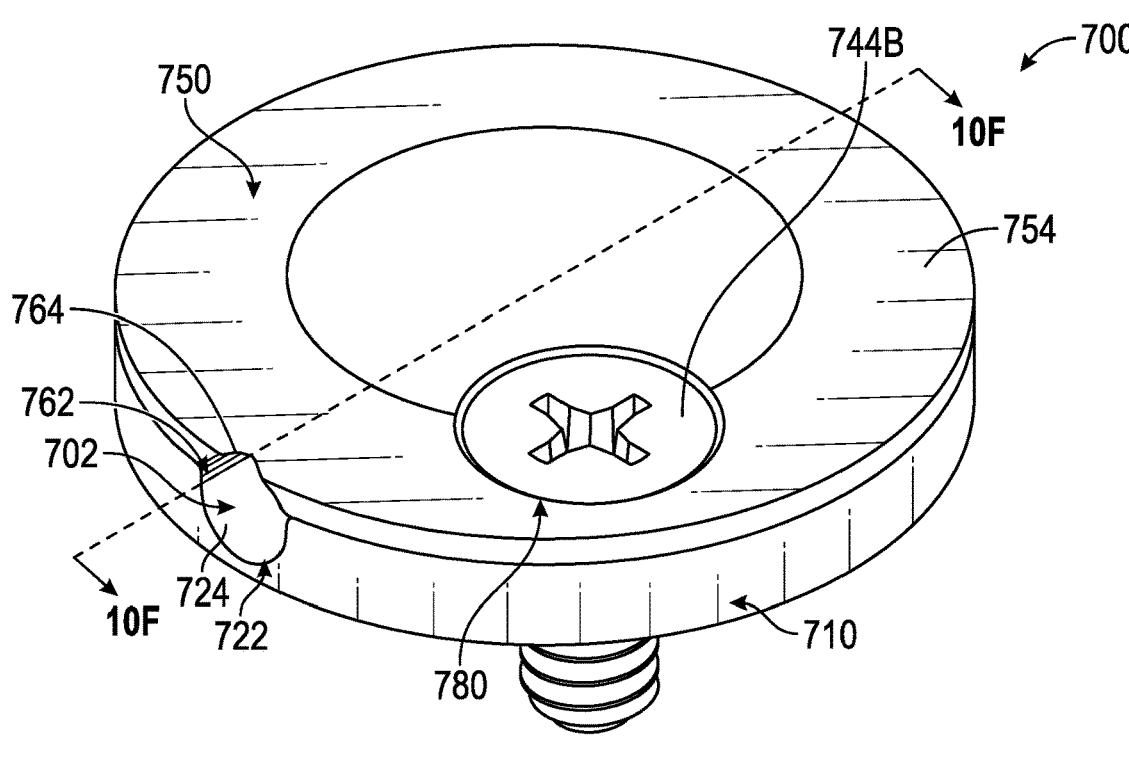
FIG. 10D is a front perspective view showing the cranial lead fixation device of FIG. 10A in a second closed configuration.
Figure 10E:
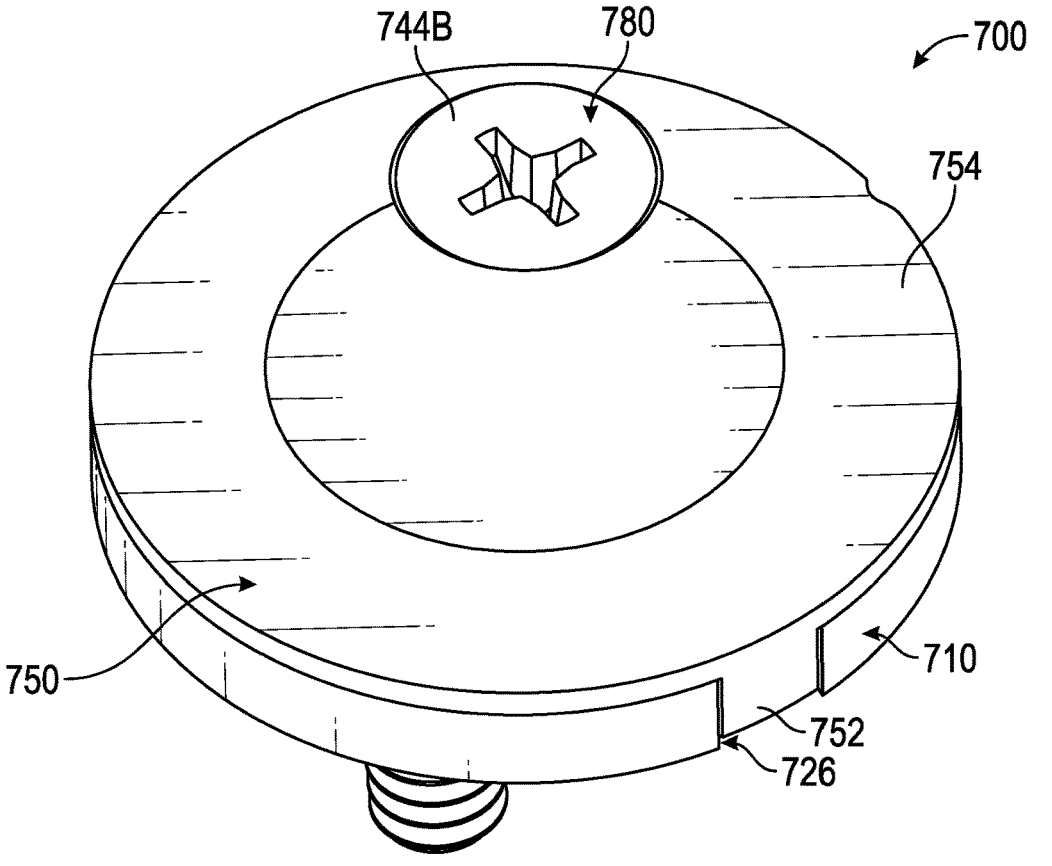
FIG. 10E is a rear perspective view showing the cranial lead fixation device of FIG. 10A in the second closed configuration.
Figure 10F:
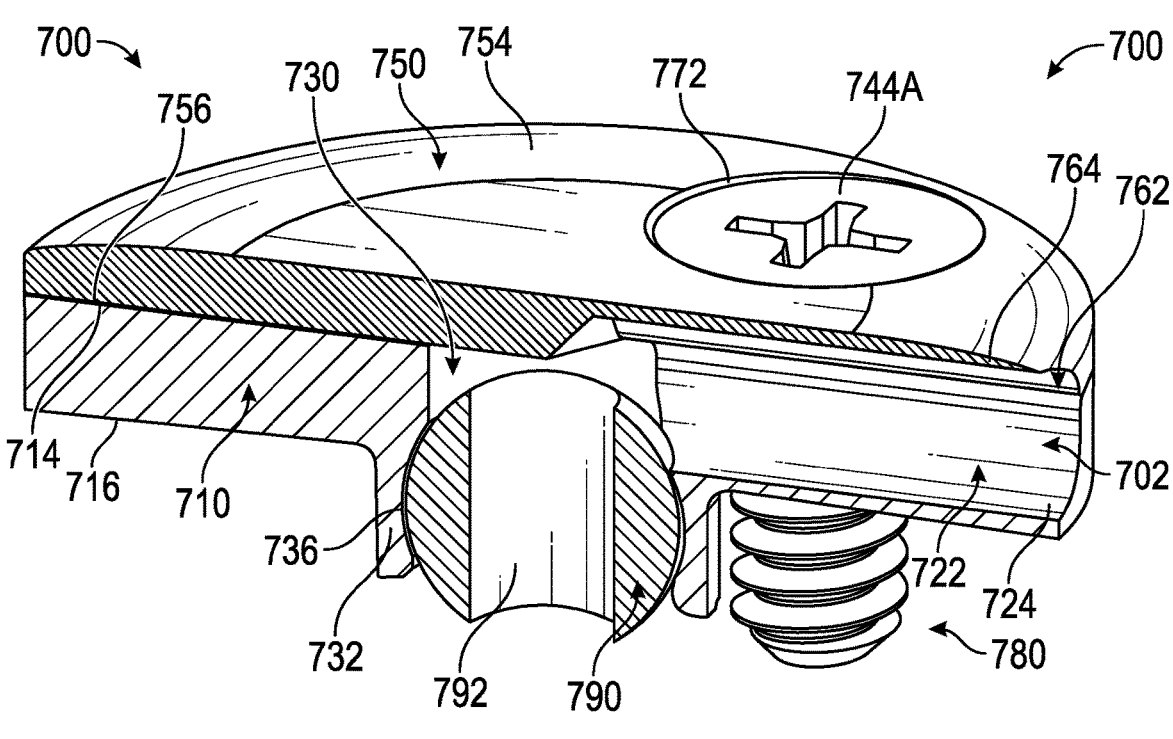
FIG. 10F is a cross-sectional view showing the cranial lead fixation device of FIG. 10D taken along line 10F-10F of FIG. 10D in the second closed configuration and having the ball oriented in the first vertical configuration.

As shown, the cranial lead fixation device 700 is operable to assume a first open configuration (FIG. 10A) and a second closed configuration (FIG. 10D). Further, the cranial lead fixation device 700 includes a fixation channel 702 for receipt of the medical device such that when the cranial lead fixation device 700 is in the first open configuration, the fixation channel 702 is "open" and operable to accept the medical device. When the cranial lead fixation device 700 is in the second "closed" configuration, the fixation channel 702 captures the medical device such that the medical device is prevented from being removed or otherwise pulled away from the cranium. In contrast with previously-discussed embodiments, the cranial lead fixation device 700 includes a rotating ball mechanism shown in FIGS. 10B, 10C, 10F and 10G that reduces a bend angle of the medical device while securing the medical device within the fixation channel 702.

As shown, the cranial lead fixation device 700 includes a body 710 that affixes directly to the cranium, and a fixation mechanism 750 coupled along the body 710 that transitions the cranial lead fixation device 700 between the first open configuration of FIG. 10A and the second closed configuration of FIG. 10D and captures the medical device within the fixation channel 702. In some embodiments, the fixation channel 702 is collectively defined by the body 710 and the fixation mechanism 750; for instance, the body 710 can define a lower half 722 of the fixation channel 702 and the fixation mechanism 750 can define an upper half 762 of the fixation channel 702. The fixation mechanism 750 can be coupled along the body 710 by a connector mechanism 780, which in some embodiments is a screw mechanism that couples the fixation mechanism 750 directly to the body 710 without need for rotation of the fixation mechanism 750 in contrast with previously-discussed embodiments.

Figure 11A:
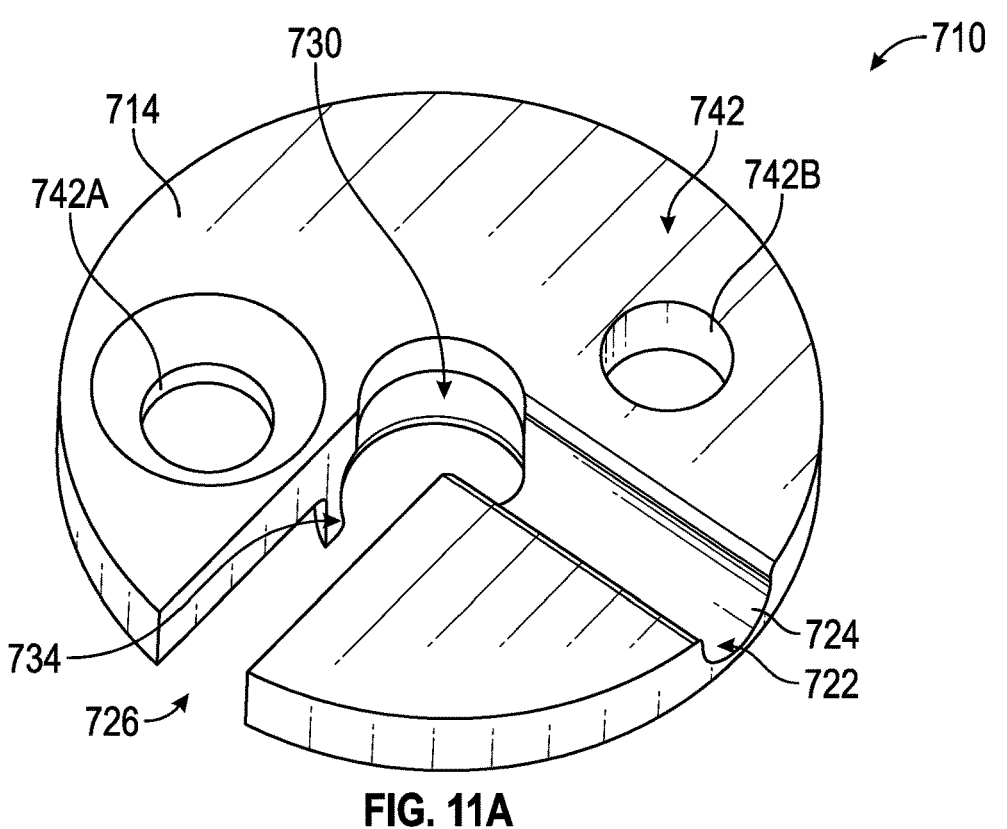
FIG. 11A is a perspective view showing a base of the cranial lead fixation device of FIG. 10A
Figure 11B:
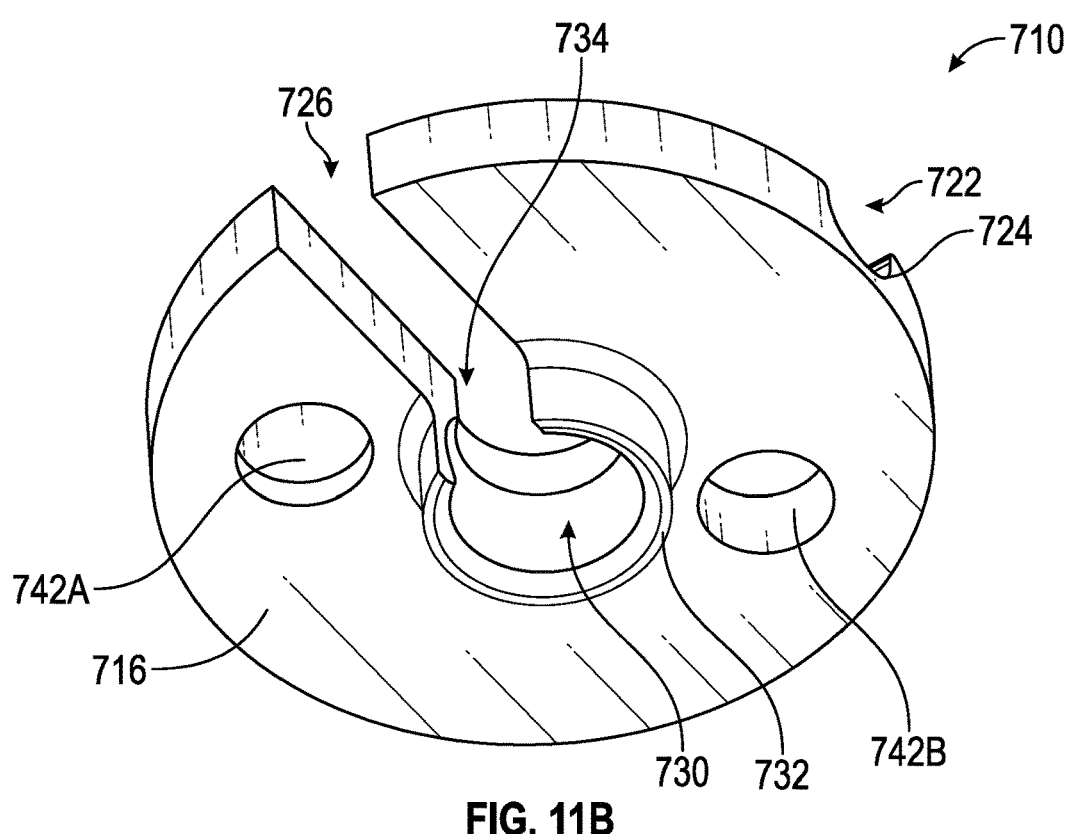
FIG. 11B is an underside perspective view showing the base of FIG. 11A.

The body 710 of the cranial lead fixation device 700 is shown alone in FIGS. 11A and 11B; as shown, the body 710 can define a generally circular configuration, and further defines an outer face 714 and an inner face 716. When the cranial lead fixation device 700 is positioned along the cranium, the outer face 714 faces away from the cranium and the inner face 716 is captured against the cranium; as such, in some embodiments, the inner face 716 is a concave surface that corresponds with a curvature of the cranium. Further, the body 710 defines a burr hole aperture 730 that aligns with the burr hole and communicates with the fixation channel 702 such that, when captured at the cranial lead fixation device 700, the medical device extends through the burr hole, the burr hole aperture 730 of the body 710, and finally through the fixation channel 702 as shown. In some embodiments, the body 710 circumferentially defines a burr hole lip 732 around the burr hole aperture 730 that extends below the inner face 716 for improved engagement with the burr hole.

Figure 10G:
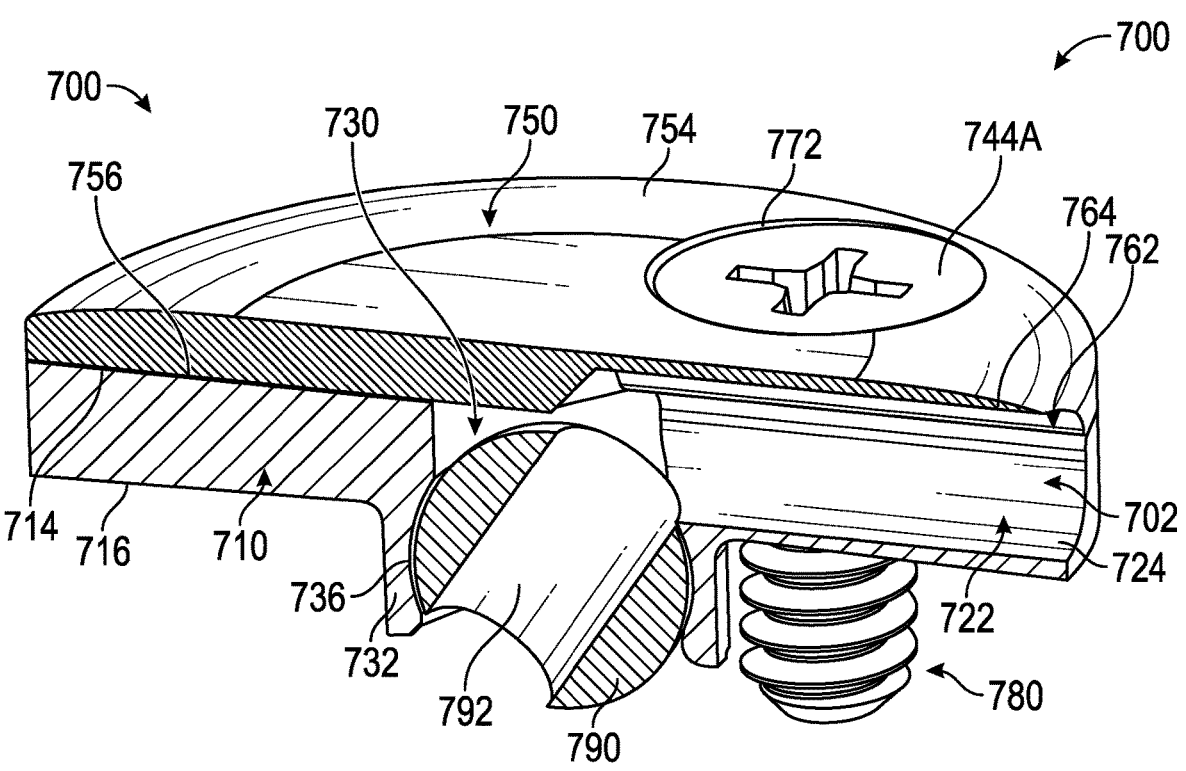
FIG. 10G is a cross-sectional view showing the cranial lead fixation device of FIG. 10F and having the ball oriented in the second angled configuration.

Further, with additional reference to FIGS. 10B, 10C, 10F and 10G, the body 710 defines a ball capture 736 within the burr hole aperture 730 that captures a ball 790 therein. As shown, the ball 790 includes a canal 792 that opens into an open portion 794 as shown. The canal 792 is configured to receive the medical device therein and serves to direct the medical device towards the fixation channel 702 while reducing strain on the medical device that could result from a 90-degree bend. As shown, the ball 790 is operable for positioning between a first vertical configuration (FIGS. 10B and 10F) and a second angled configuration (FIGS. 10C and 10G).

In some embodiments, the body 710 includes an insertion channel 726 in communication with an open portion 734 of the burr hole aperture 730 that enables a practitioner to position the medical device within the burr hole aperture 730 following fixation of the body 710 along the cranium; that is, the insertion channel 726 and open portion 734 eliminate the need to "thread" the medical device through the burr hole aperture 730 prior to fixation of the body 710 along the cranium. The insertion channel 726 aligns with the open portion 794 of the canal 792 of the ball 790 such that the medical device can be inserted through the insertion channel 726 until the medical device is captured within the canal 792 of the ball 790. Following capture of the medical device at the ball 790, the ball 790 can then be rotated to the second angled configuration such that the remaining length of the medical device is angled towards the fixation channel 702.

As further shown, the body 710 includes a plurality of cranial screw apertures 742 (shown in the figures as cranial screw apertures 742A and 742B) configured to receive a plurality of cranial screws (shown in the figures as cranial screws 744A and 744B) for fixation of the body 710 to the cranium, including a first cranial screw aperture 742A configured to receive a first cranial screw 744A and a second cranial screw aperture 742B configured to receive a second cranial screw 744B. The body 710 can couple along the cranium by insertion of the first cranial screw 744A into the first cranial screw aperture 742A and the cranium 20; note that the second cranial screw 744B can be installed after closure of the cranial lead fixation device 700 to connect the fixation mechanism 750 to the body 710 as will be discussed in greater detail below. As shown, the first cranial screw aperture 742A can be recessed into the body 710, providing a seat for the first cranial screw 744A and enabling the fixation mechanism 750 to lie flat against the body 710 when coupled along the body 710. The second cranial screw aperture 742B can be flat along the outer face 714 of the body 710.

Figure 12A:
FIG. 12A is a perspective view showing a fixation mechanism of the cranial lead fixation device of FIG. 10A
Figure 12A:
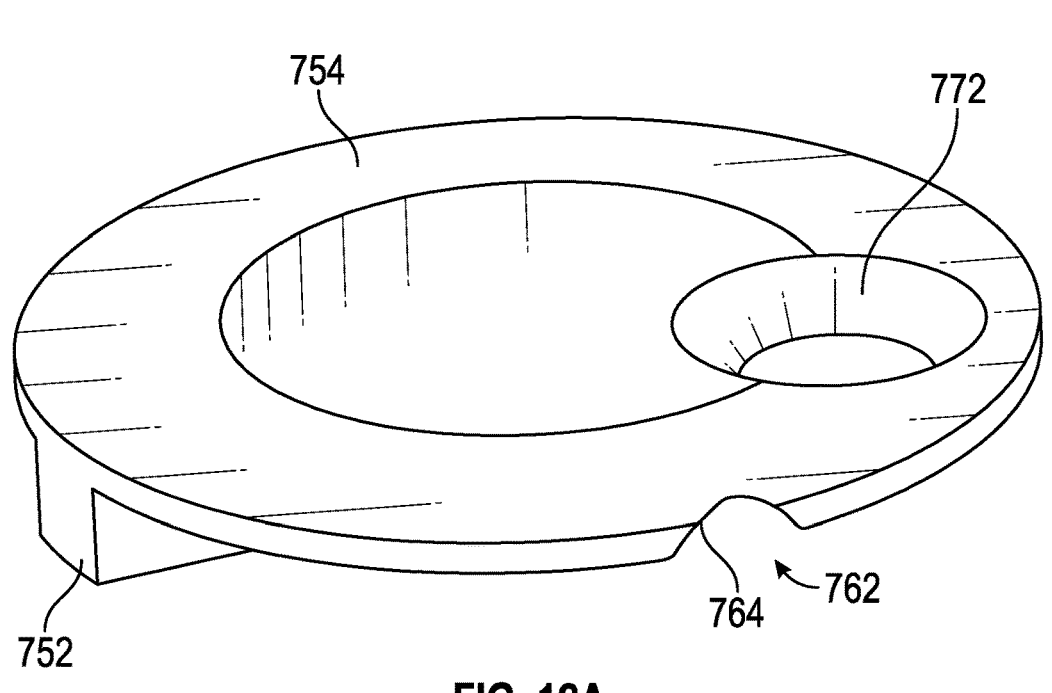
Figure 12B:
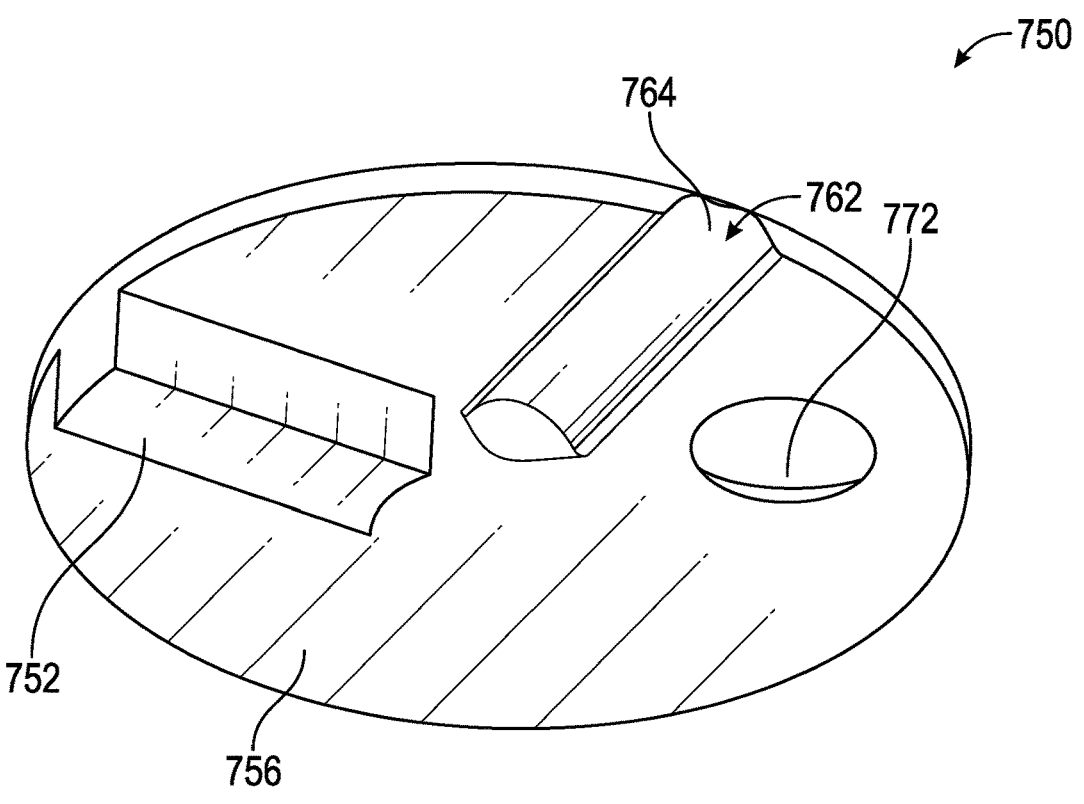
FIG. 12B is an underside perspective view showing the fixation mechanism of FIG. 12A.

The fixation mechanism 750, shown alone in FIGS. 12A and 12B, is removably coupled with the body 710; when the fixation mechanism 750 is decoupled from the body 710, the cranial lead fixation device 700 is in the first open configuration of FIGS. 10A-10C. Conversely, when the fixation mechanism 750 is coupled to the body 710, the cranial lead fixation device 700 is in the second closed configuration of FIGS. 10D-10G. In the embodiment shown, the fixation mechanism 750 is of a generally planar or plate-like configuration. The fixation mechanism 750 includes an outer face 754 and an inner face 756 such that when the fixation mechanism 750 is coupled along the body 710 and the body 710 is coupled along the cranium, the outer face 754 of the fixation mechanism 750 faces away from the body 710 and the cranium and the inner face 756 faces the outer face 714 of the body 710 as shown. In a further aspect, the fixation mechanism 750 is coupled along the body 710 at the connector mechanism 780, which in the embodiment shown can include the second cranial screw 744B configured for insertion into a second cranial screw seat 772 of the fixation mechanism 750 that aligns with the second cranial screw aperture 742B of the body 710. To couple the fixation mechanism 750 to the body 710, a practitioner can align the second cranial screw seat 772 with the second cranial screw aperture 742B and insert the second cranial screw 744B through the second cranial screw seat 772, the second cranial screw aperture 742B, and into the cranium.

The inner face 756 of the fixation mechanism 750 provides a protrusion 752 that engages within and closes off the insertion channel 726 of the body 710 when the cranial lead fixation device 700 is in the second closed configuration to prevent migration of the medical device out of the burr hole aperture 730 of the body 710.

As shown and as discussed above, the fixation mechanism 750 forms the upper half 762 of the fixation channel 702, and the body 710 forms the lower half 722 of the fixation channel 702. In particular, the body 710 includes a fixation channel floor 724 along the outer face 714 that forms the lower half 722 of the fixation channel 702; similarly, the fixation mechanism 750 includes a fixation channel ceiling 764 along the inner face 756 that forms the upper half 762 of the fixation channel 702. When the cranial lead fixation device 700 is in the second closed configuration of FIGS. 10D-10G, the lower half 722 of the fixation channel 702 and the upper half 762 of the fixation channel 702 are aligned with one another to complete the fixation channel 702. Similarly, when in the second closed configuration, the fixation mechanism 750 can occlude the burr hole aperture 730 of the body 710.

As discussed above, the cranial lead fixation device 700 can be affixed directly to the cranium. In some embodiments, the cranial lead fixation device 700 can be configured in the first open configuration of FIGS. 10A and 10B, and the body 710 can couple along the cranium by insertion of the first cranial screw 744A into the first cranial screw aperture 742A and into the cranium. At this time, the medical device may already protrude from the burr hole of the cranium; as such, the cranial lead fixation device 700 can be positioned over the burr hole and the medical device can be passed through the insertion channel 726 and into the burr hole aperture 730. Following coupling of the body 710 to the cranium and following capture of the medical device within the canal 792 of the ball 790 (positioned within the burr hole aperture 730) and the lower half 122 of the fixation channel 102, a practitioner can position the fixation mechanism 750 over the body 710 to transition the cranial lead fixation device 700 from the first open configuration of FIGS. 10A-10C into the second closed configuration of FIGS. 10D-10G, completing the fixation channel 702 such that the medical device is enclosed within the fixation channel 702. Following closure of the cranial lead fixation device 700, a practitioner can insert the second cranial screw 744B through the second cranial screw seat 772 of the fixation mechanism 750, the second cranial screw aperture 742B of the body 710, and into the cranium. When fully assembled, the first cranial screw 744A nests within the first cranial screw aperture 742A and the second cranial screw 744B nests within the second cranial screw seat 772.

Figure 13:
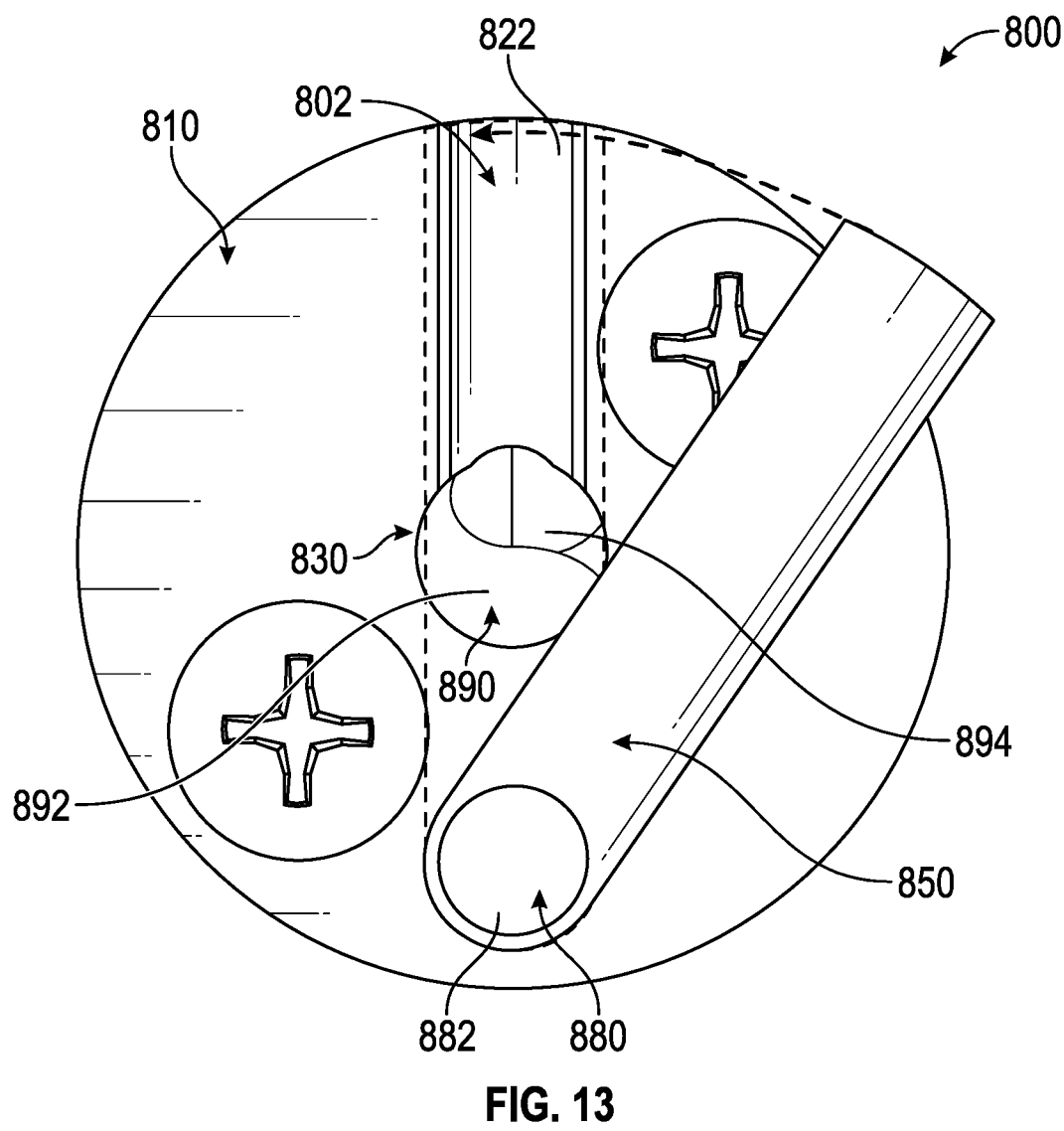
FIG. 13 is a top plan view showing an eighth embodiment of a cranial lead fixation device similar to that of FIG. 10A where a fixation mechanism resembles an arm and operable for rotation between a first open configuration and a second closed configuration (shown in phantom)

FIG. 13 shows an eighth embodiment of the cranial lead fixation device, designated as cranial lead fixation device 800, that is similar to the cranial lead fixation device 700 and includes a fixation channel 802 collectively defined by a body 810 and a fixation mechanism 850 linked at a connector mechanism 880, where the body 810 includes a burr hole aperture 830 in communication with the fixation channel 802 for capture of a medical device (shown as medical device 10 in FIGS. 1A-1F with reference to cranial lead fixation device 100, but is similarly applicable for the cranial lead fixation device 800 of FIG. 13). Further, the cranial lead fixation device 800 similarly includes a ball 890 positioned within the burr hole aperture 830, where the ball 890 includes a canal 892 and an open portion 894 that collectively accept the medical device. The cranial lead fixation device 800 is similarly configurable in a first open configuration and a second closed configuration (shown in phantom). Similarly, when in the second closed configuration, the fixation mechanism 850 can occlude the burr hole aperture 830 of the body 810.

In contrast with the cranial lead fixation device 700, the fixation mechanism 850 of the cranial lead fixation device 800 can be of a generally arm-like configuration similar to the fixation mechanisms 450, 550 and 650 discussed above. As such, the connector mechanism 880 can be similar to the connector mechanisms 480, 580 and 680. The fixation channel 802 is collectively defined by the body 810 and the fixation mechanism 850; for instance, the body 810 can define a lower half 822 of the fixation channel 802 and the fixation mechanism 850 can define an upper half (not visible but analogous to lower half 422 of FIGS. 7A-7C) of the fixation channel 802. The fixation mechanism 850 can be coupled along the body 810 by the connector mechanism 880, which in some embodiments can include a pivot hinge 882 that connects the fixation mechanism 850 to the body 810 and enables rotation of the fixation mechanism 850 about the pivot hinge 882 between the first open configuration and the second closed configuration.

Figure 14A:
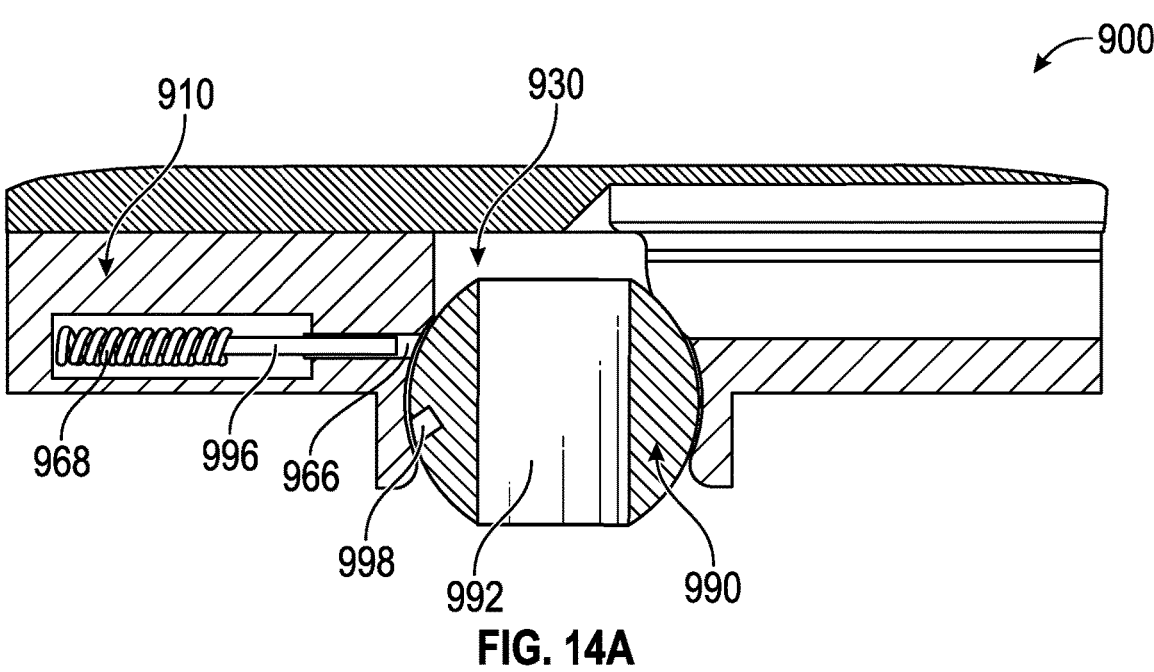
FIG. 14A is a cross-sectional side view showing a ninth embodiment of a cranial lead fixation device similar to that of FIG. 10A and including a base having a pin and tensioning element in association with a ball, the ball being oriented in a first vertical configuration.
Figure 14B:
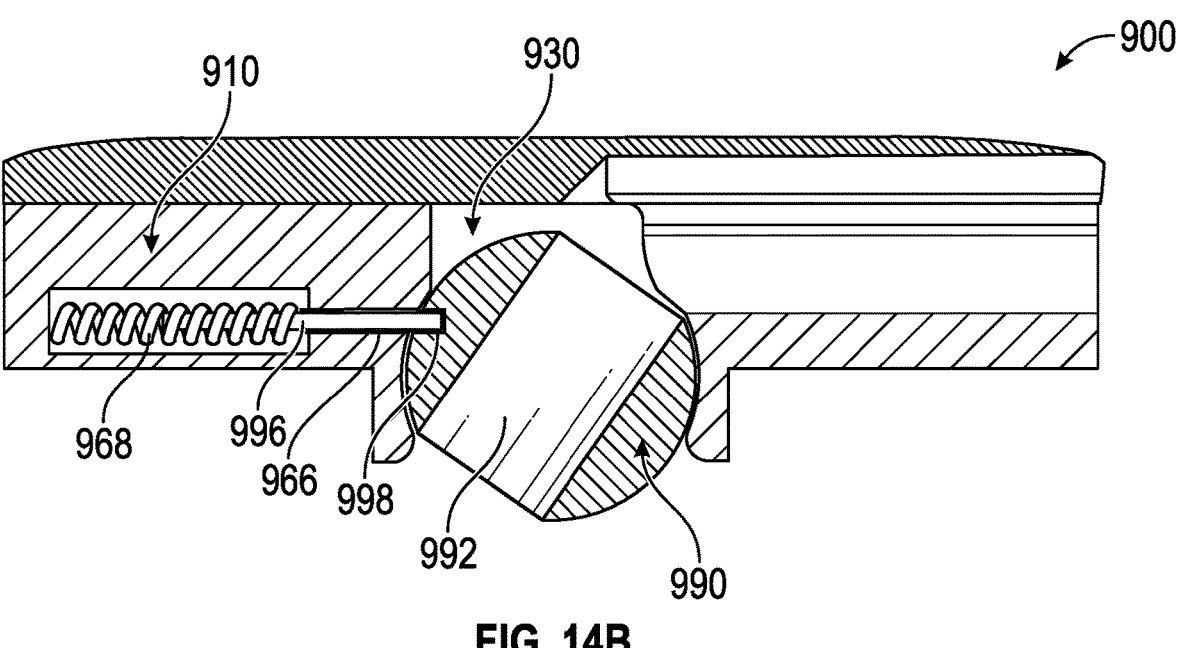
FIG. 14B is a cross-sectional side view showing the cranial lead fixation device of FIG. 14A with the ball being oriented in a second angled configuration and the pin being inserted into a pin channel of the ball.

FIGS. 14A and 14B show a ninth embodiment of the cranial lead fixation device, designated as cranial lead fixation device 900, that is similar to the cranial lead fixation devices 700 and 800 and includes a body 910 having a ball 990 positioned within a burr hole aperture 930 of the body, where the ball 990 includes a canal 992 and an open portion (not shown, but analogous to open portion 794 of FIGS. 10B and 10B) that accepts the medical device. The ball 990 is similarly configured for positioning between a first vertical configuration (FIG. 14A) and a second angled configuration (FIG. 14B). In this embodiment, the body 910 can couple with a fixation mechanism, which can be configured similar to the fixation mechanism 750 of FIGS. 10D-10G, 12A and 12B or the fixation mechanism 850 of FIG. 13. As shown, the body 910 can include a pin channel 966 defined horizontally within the body 910 and in communication with the burr hole aperture 930. The pin channel 966 can include a tensioning element 968 and a pin 996 in association with the tensioning element 968, where the tensioning element 968 is biased towards pushing the pin 996 out of the pin channel 966 and into the burr hole aperture 930 to contact the ball 990. When the ball 990 is positioned in the first vertical configuration of FIG. 14A, the tensioning element 968 applies a lateral force to the pin 996 such that the pin 996 contacts the ball 990. The ball 990 can include a pin receptacle 998 that aligns with the pin receptacle when in the second angled configuration of FIG. 14B such that when the ball 990 is oriented in the second angled configuration, the tensioning element 968 pushes the pin 996 into the pin receptacle 998 of the ball 990, thereby locking the ball 990 in place.

FIGS. 15A-15F illustrate a tenth embodiment of the cranial lead fixation device, designated as cranial lead fixation device 1000, for capturing and securing a medical device (shown as medical device 10 in FIGS. 1A-1F with reference to cranial lead fixation device 100, but is similarly applicable for the cranial lead fixation device 1000 of FIGS. 15A-15F) within a burr hole formed within a cranium (shown in FIGS. 1B-1F as cranium 20 and burr hole 30).

Figure 15A:
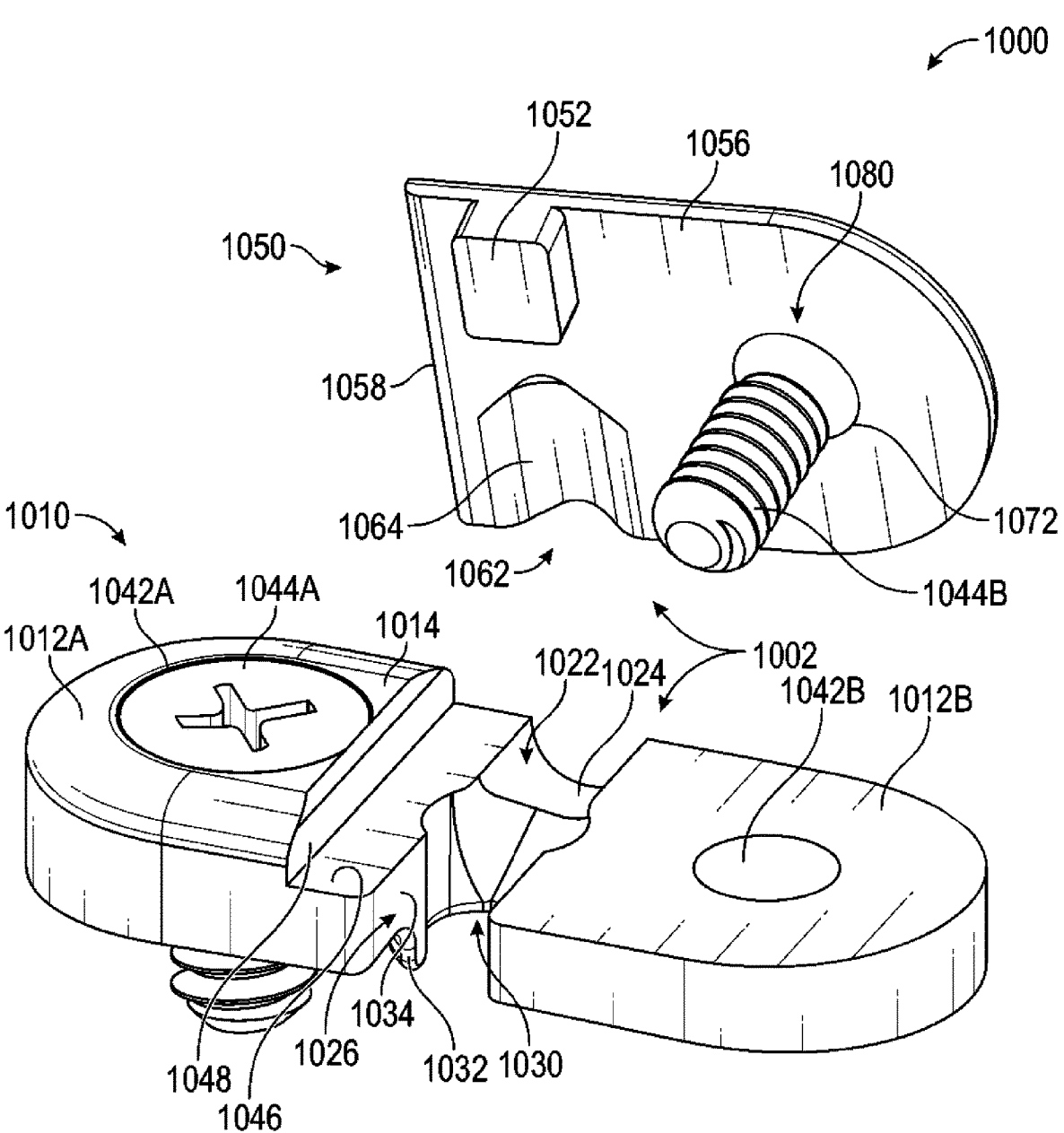
FIG. 15A is a rear perspective view showing a tenth embodiment of a cranial lead fixation device in a first open configuration.
Figure 15B:
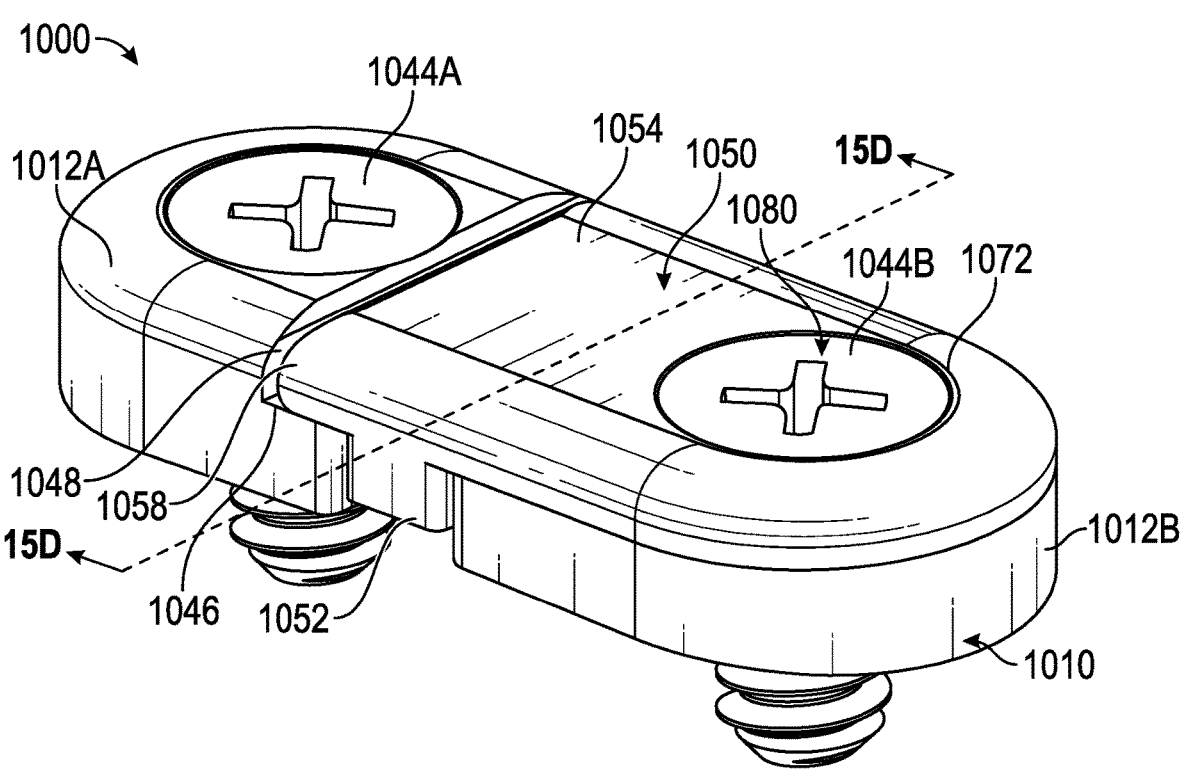
FIG. 15B is a rear perspective view showing the cranial lead fixation device of FIG. 15A in a second closed configuration.
Figure 15C:
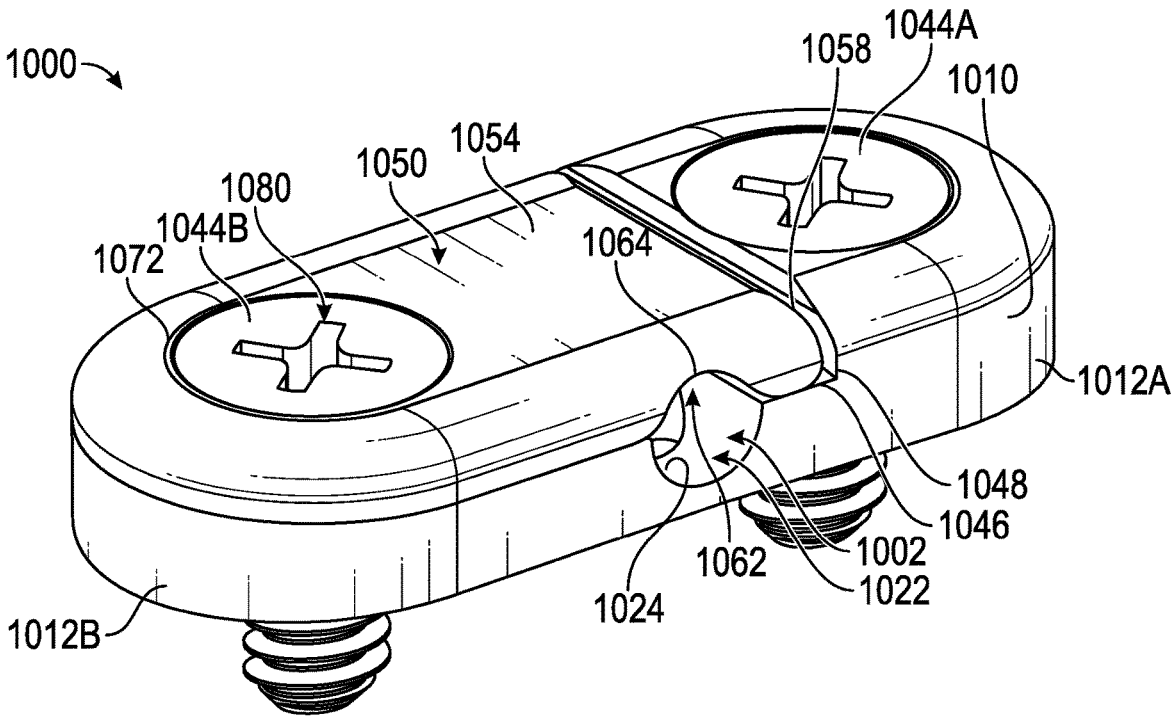
FIG. 15C is a front perspective view showing the cranial lead fixation device of FIG. 15B.
Figure 15D:
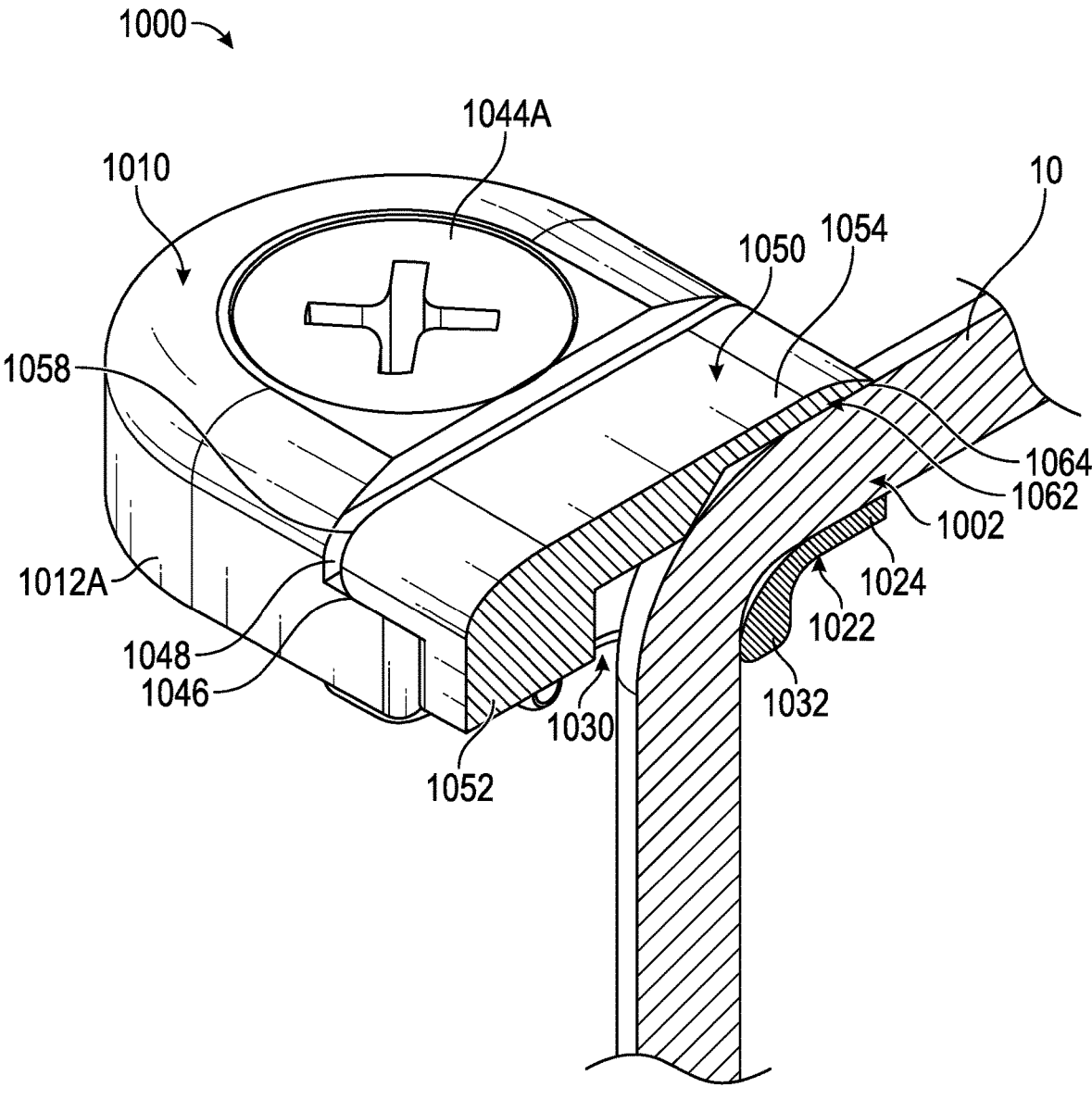
FIG. 15D is a cross-sectional view showing the cranial lead fixation device of FIG. 15B taken along line 15D-15D of FIG. 15B.
Figure 15E:
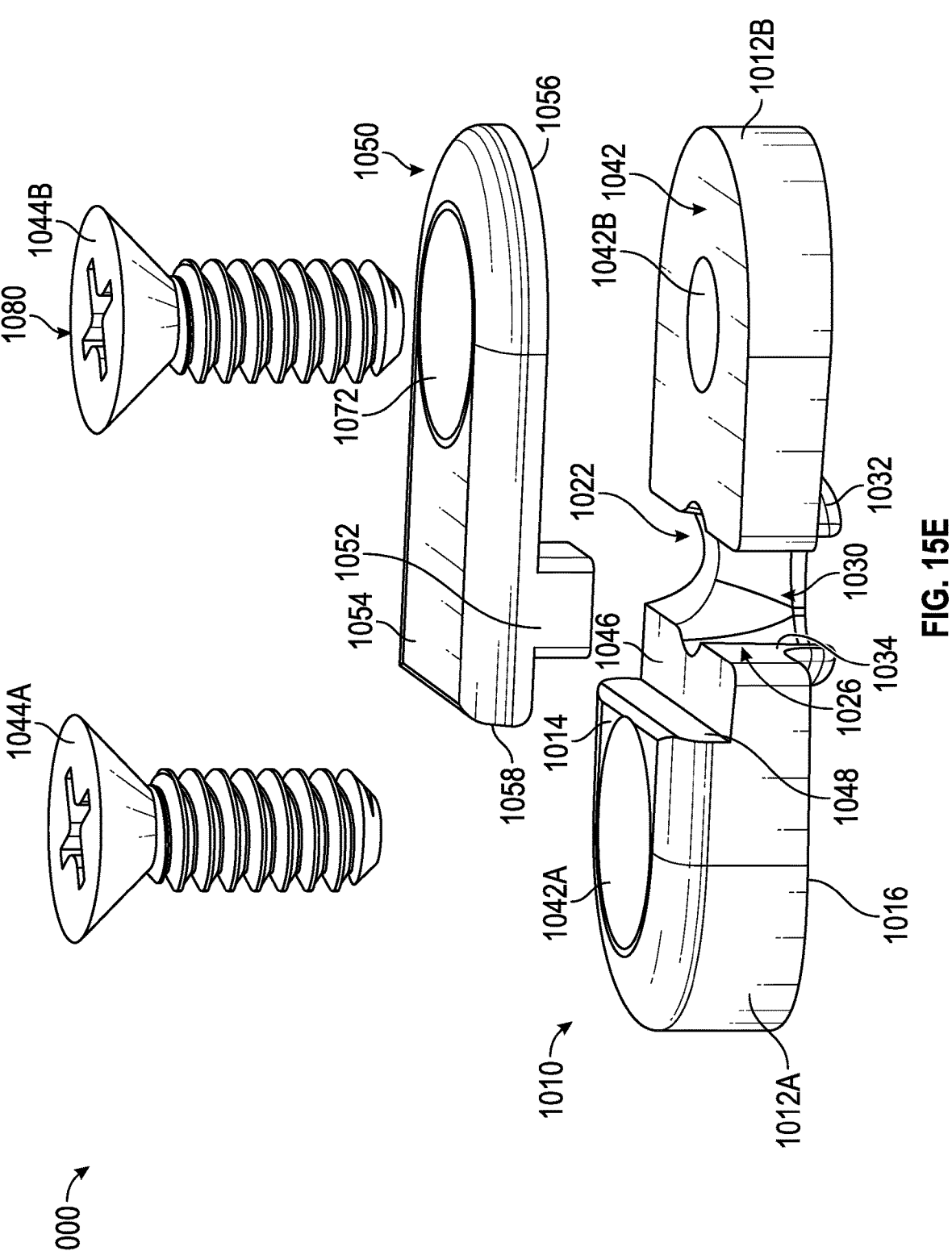
FIG. 15E is an exploded view showing the cranial lead fixation device of FIG. 15A.

As shown, the cranial lead fixation device 1000 is operable to assume a first open configuration (FIG. 15A) and a second closed configuration (FIGS. 15B-15D). Further, the cranial lead fixation device 1000 includes a fixation channel 1002 for receipt of the medical device such that when the cranial lead fixation device 1000 is in the first open configuration, the fixation channel 1002 is "open" and operable to accept the medical device. When the cranial lead fixation device 1000 is in the second "closed" configuration, the fixation channel 1002 captures the medical device such that the medical device is prevented from being removed or otherwise pulled away from the cranium. FIG. 15E provides an exploded view of the cranial lead fixation device 1000.

The cranial lead fixation device 1000 includes a body 1010 that affixes directly to the cranium, and a fixation mechanism 1050 removably coupled along the body 110 that transitions the cranial lead fixation device 1000 between the first open configuration of FIG. 15A and the second closed configuration of FIGS. 15B-15D and captures the medical device within the fixation channel 1002. In some embodiments, the fixation channel 1002 is collectively defined by the body 1010 and the fixation mechanism 1050; for instance, the body 1010 can define a lower half 1022 of the fixation channel 1002 and the fixation mechanism 1050 can define an upper half 1062 of the fixation channel 1002. The fixation mechanism 1050 can be coupled along the body 1010 by a connector mechanism 1080, which in some embodiments includes a cranial screw (in particular, a second cranial screw 1044B as will be described in greater detail below) that couples the fixation mechanism 1050 to the body 1010, however other configurations are contemplated and described in further embodiments herein.

Figure 15F:
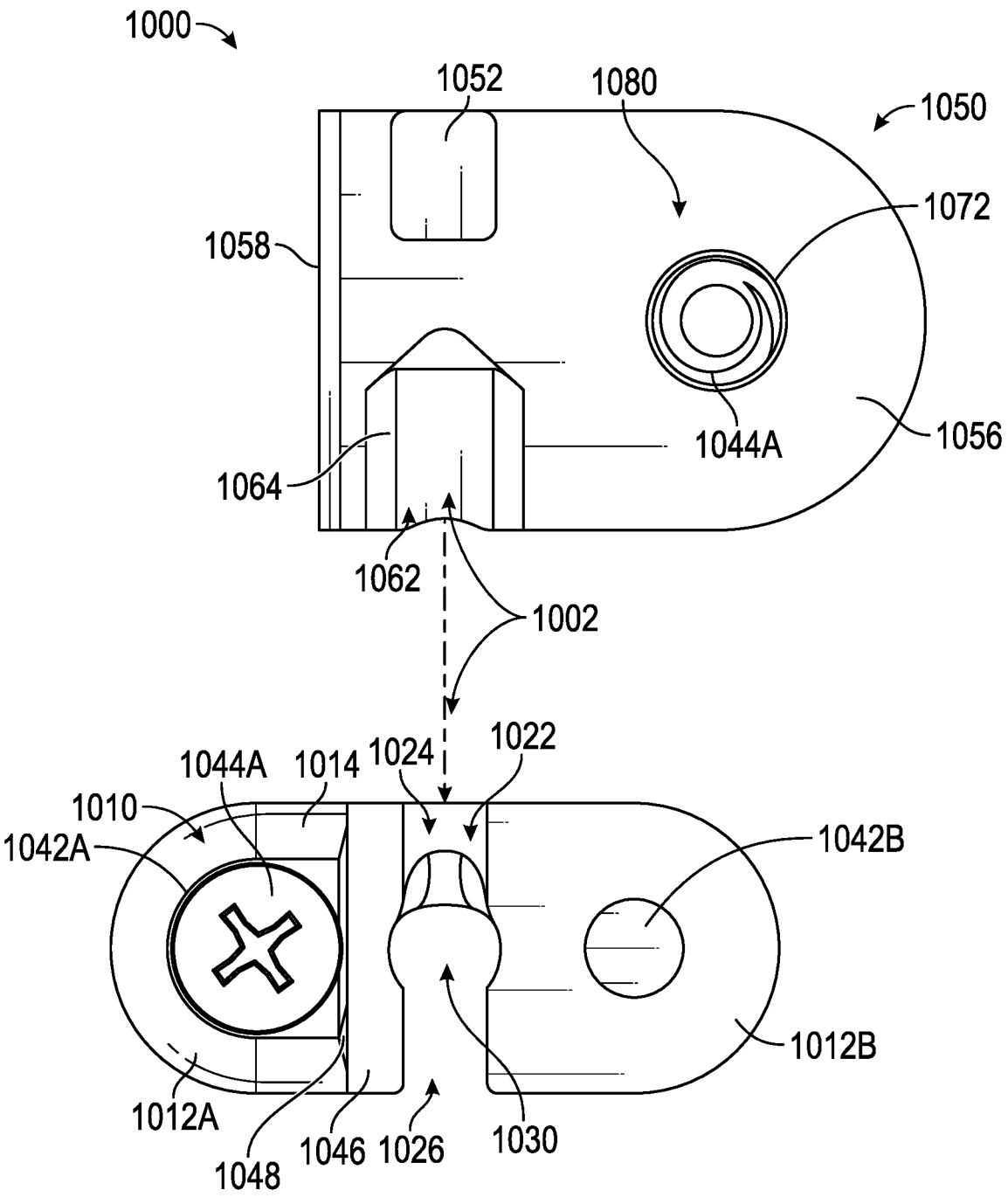
FIG. 15F is an illustration showing alignment of a fixation mechanism with a base of the cranial lead fixation device of FIG. 15A.

The body 1010 of the cranial lead fixation device 1000 is shown in FIGS. 15E and 15F; as shown, the body 1010 can define a first wing 1012A, and a second wing 1012B, and further defines an outer face 1014 and an inner face 1016. When the cranial lead fixation device 100 is positioned along the cranium, the outer face 1014 faces away from the cranium and the inner face 1016 is captured against the cranium; as such, in some embodiments, the inner face 1016 is a concave surface that corresponds with a curvature of the cranium. Further, the body 1010 defines a burr hole aperture 1030 that aligns with the burr hole and communicates with the fixation channel 1002 such that, when captured at the cranial lead fixation device 1000, the medical device extends through the burr hole, the burr hole aperture 1030 of the body 1010, and finally through the fixation channel 1002 as shown. In some embodiments, the body 1010 circumferentially defines a burr hole lip 1032 around the burr hole aperture 1030 that extends below the inner face 1016 for improved engagement with the burr hole.

In some embodiments, the body 1010 includes an insertion channel 1026 in communication with an open portion 1034 of the burr hole aperture 1030 that enables a practitioner to position the medical device within the burr hole aperture 1030 following fixation of the body 1010 along the cranium; that is, the insertion channel 1026 and open portion 1034 eliminate the need to "thread" the medical device through the burr hole aperture 1030 prior to fixation of the body 1010 along the cranium.

As further shown, the body 1010 includes a plurality of cranial screw apertures (shown in the figures as cranial screw apertures 1042A and 1042B) configured to receive a plurality of cranial screws (shown in the figures as cranial screws 1044A and 1044B) for fixation of the body 1010 to the cranium, including a first cranial screw aperture 1042A configured to receive a first cranial screw 1044A and a second cranial screw aperture 1042B configured to receive a second cranial screw 1044B. The body 1010 can couple along the cranium by insertion of the first cranial screw 1044A into the first cranial screw aperture 1042A and the cranium; note that the second cranial screw 1044B can be installed after closure of the cranial lead fixation device 1000 to connect the fixation mechanism 1050 to the body 1010 as will be discussed in greater detail below. In some embodiments, the first cranial screw aperture 1042A is positioned along the first wing 1012A of the body 1010 and the second cranial screw aperture 1042B is positioned along the second wing 1012B of the body 1010. As shown, the first cranial screw aperture 1042A can be raised, providing a seat for the first cranial screw 1044A, while the second cranial screw aperture 1042B can be flat along the outer face 1014 of the body 1010 to receive the fixation mechanism 1050 when transitioning the cranial lead fixation device 1000 between the first open configuration of FIG. 15A and the second closed configuration of FIGS. 15B-15D.

As discussed and as shown, the fixation mechanism 1050 is configured for removable coupling along the body 1010 and is operable for placement between the first open configuration of FIG. 15A and the second closed configuration of FIGS. 15B-15D; in particular, when the fixation mechanism 1050 is decoupled from the body 1010 as shown in FIG. 15A, the cranial lead fixation device 1000 is in the first open configuration and when the fixation mechanism 1050 is coupled to the body 1010 as shown in FIGS. 15B-15D, the cranial lead fixation device 1000 is in the second closed configuration. In the embodiment shown, the fixation mechanism 1050 is of a generally planar or plate-like configuration. The outer face 1014 of the body 1010 includes a shelf 1046 having a receiving abutment surface 1048 configured to receive the fixation mechanism 1050 as shown. The fixation mechanism 1050 includes an outer face 1054 and an inner face 1056 such that when the fixation mechanism 1050 is coupled along the body 1010 and the body 1010 is coupled along the cranium, the outer face 1054 of the fixation mechanism 1050 faces away from the body 1010 and the cranium and the inner face 1056 faces the shelf 1046 of the body 1010 as shown. The fixation mechanism 1050 includes a terminal abutment surface 1058 that contacts the receiving abutment surface 1048 of the shelf 1046 of the body 1010 when in the second closed configuration of FIGS. 15B-15D. In a further aspect, the fixation mechanism 1050 is coupled along the body 1010 at the connector mechanism 1080, which in the embodiment shown can include the second cranial screw 1044B configured for insertion into a second cranial screw seat 1072 of the fixation mechanism 1050 and the second cranial screw aperture 1042B of the body 1010; as shown, the second cranial screw seat 1072 of the fixation mechanism 1050 aligns with the second cranial screw aperture 1042B of the body 1010 when the fixation between the first open configuration of FIG. 15A and the second closed configuration of FIGS. 15B-15D.

The inner face 156 of the fixation mechanism 1050 provides a protrusion 1052 that engages within and closes off the insertion channel 1026 of the body 1010 when the cranial lead fixation device 1000 is in the second closed configuration to prevent migration of the medical device out of the burr hole aperture 1030 of the body 1010. In addition, the outer face 1054 of the fixation mechanism 1050 includes the second cranial screw seat 1072 that aligns with the second cranial screw aperture 1042B of the body 1010 when the cranial lead fixation device 1000 is in the second closed configuration of FIGS. 15B-15D.

As shown and as discussed above, fixation mechanism 1050 forms the upper half 1062 of the fixation channel 1002 and the body 1010 forms the lower half 1022 of the fixation channel 1002. In particular, the body 1010 includes a fixation channel floor 1024 along the outer face 1014 that forms the lower half 1022 of the fixation channel 1002; similarly, the fixation mechanism 1050 includes a fixation channel ceiling 1064 along the inner face 1056 that forms the upper half 1062 of the fixation channel 1002. When the cranial lead fixation device 1000 is in the second closed configuration of FIGS. 15B-15D, the lower half 1022 of the fixation channel 1002 and the upper half 1062 of the fixation channel 1002 are aligned with one another to complete the fixation channel 1002. When in the second closed configuration, the fixation mechanism 1050 can occlude the burr hole aperture 1030 of the body 1010.

As discussed above, the cranial lead fixation device 1000 can be affixed directly to the cranium. In some embodiments, the cranial lead fixation device 1000 can be configured in the first open configuration of FIG. 15A, and the body 1010 can be coupled along the cranium by insertion of the first cranial screw 1044A into the first cranial screw aperture 1042A and the cranium. At this time, the medical device may already protrude from the burr hole of the cranium; as such, the cranial lead fixation device 1000 can be positioned over the burr hole and the medical device can be passed through the insertion channel 1026 and into the burr hole aperture 1030 of the body 1010. Following coupling of the body 1010 to the cranium and following capture of the medical device within the burr hole aperture 1030 and the lower half 1022 of the fixation channel 1002, a practitioner can position the fixation mechanism 1050 from the first open configuration of FIG. 15A and into the second closed configuration of FIGS. 15B-15D to complete the fixation channel 1002 such that the medical device is enclosed within the fixation channel 1002. Following closure of the cranial lead fixation device 1000, a practitioner can insert the second cranial screw 1044B through the second cranial screw seat 1072 of the fixation mechanism 1050, the second cranial screw aperture 1042B of the body 1010, and into the cranium. When fully assembled, the first cranial screw 1044A nests within the first cranial screw aperture 1042A of the body 1010 and the second cranial screw 1044B nests within the second cranial screw seat 1072 of the fixation mechanism 1050.

Figure 16:
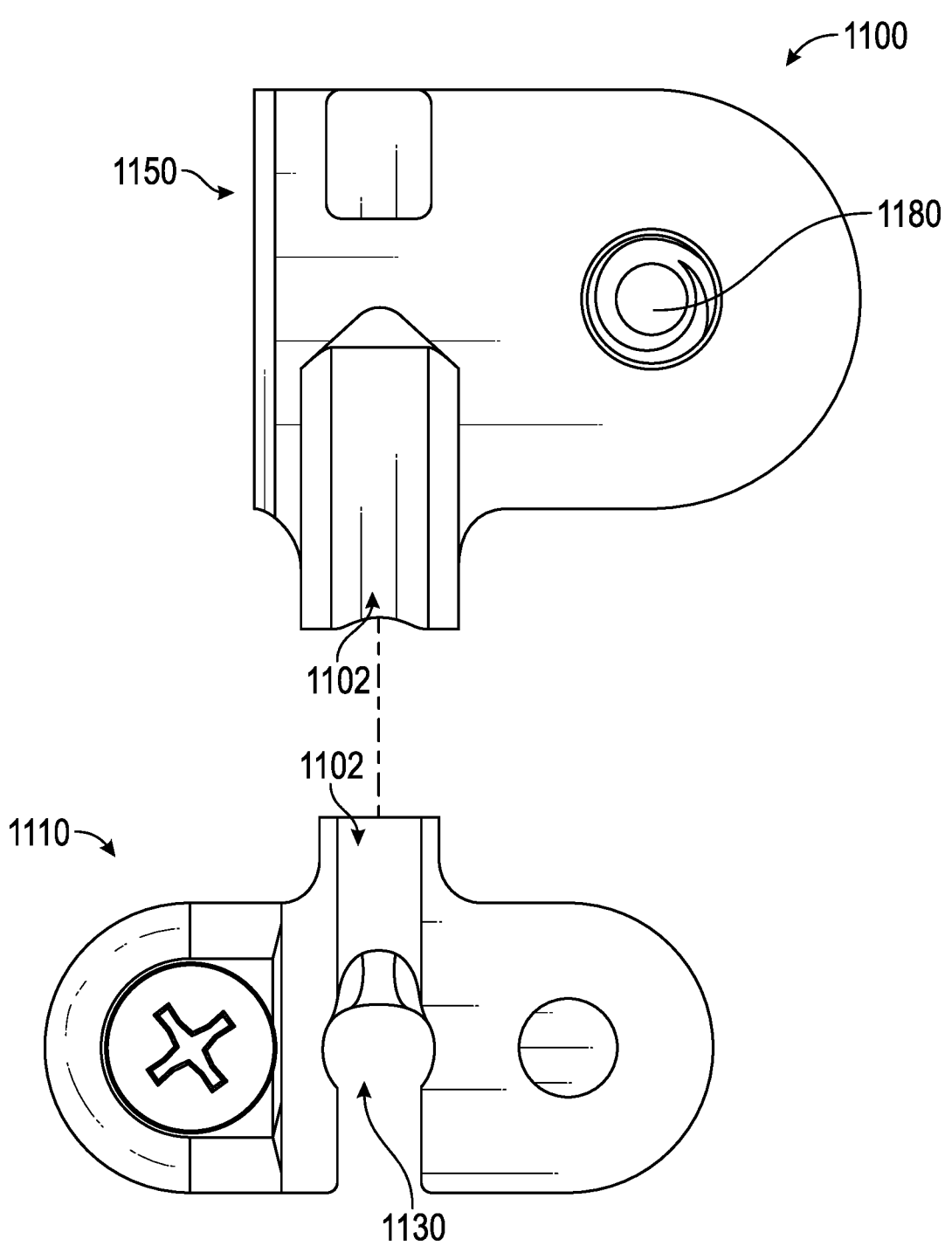
FIG. 16 is an illustration showing an eleventh embodiment of a cranial lead fixation device in a first open configuration, particularly showing alignment of a fixation mechanism with a base of the cranial lead fixation device and featuring an elongated fixation channel.

With reference to FIG. 16, an eleventh embodiment of the cranial lead fixation device, designated as cranial lead fixation device 1100, is similar to the cranial lead fixation device 1100 of FIGS. 15A-15F and includes a fixation channel 1102 collectively defined by a body 1110 and a fixation mechanism 1150 linked at a connector mechanism 1180, where the body 1110 includes a burr hole aperture 1130 in communication with the fixation channel 1102 for capture of a medical device (shown as medical device 10 in FIGS. 1A-1F with reference to cranial lead fixation device 100, but is similarly applicable for the cranial lead fixation device 1100 of FIG. 16). The cranial lead fixation device 1100 is similarly configurable in a first open configuration shown in FIG. 16 and a second closed configuration (shown in FIGS.

15B-15D with respect to the cranial lead fixation device 1000, but is similarly applicable for the cranial lead fixation device 1100 of FIG. 16). When in the second closed configuration, the fixation mechanism 1150 can occlude the burr hole aperture 1130 of the body 1110.

In contrast with the cranial lead fixation device 1000 of FIGS. 15A-15F, the fixation channel 1102 can be elongated and can extend further beyond the perimeter of the body 1110 and the fixation mechanism 1150. This modification can similarly be applied to any of the preceding embodiments of the cranial lead fixation device 100-900.

Figure 17A:
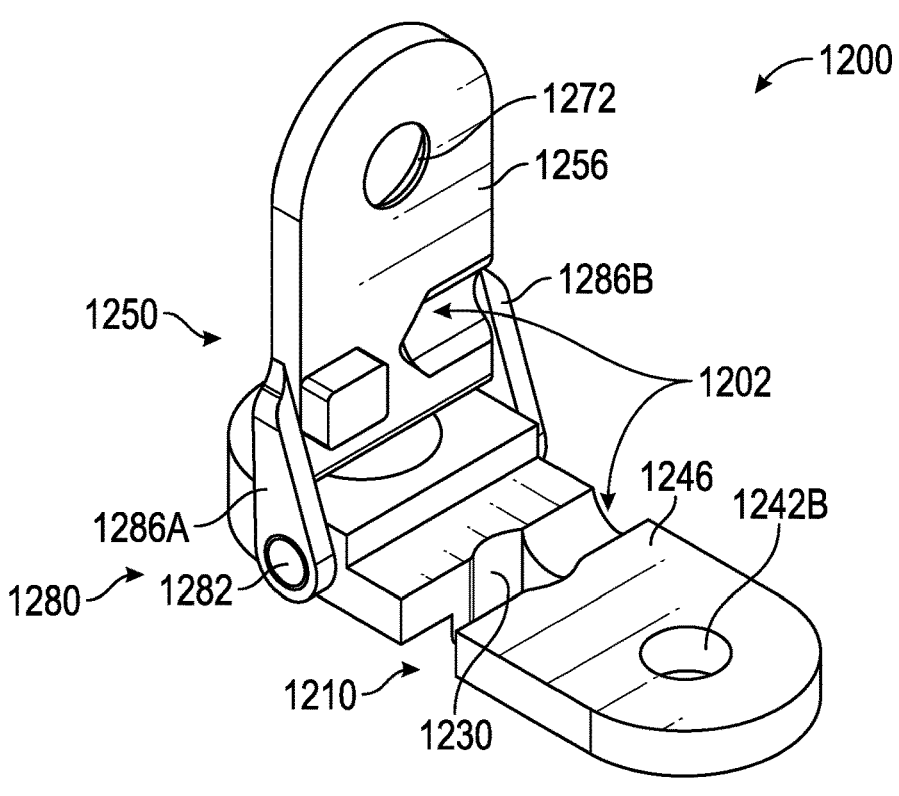
FIG. 17A is a rear perspective view showing a twelfth embodiment of a cranial lead fixation device in a first open configuration.
Figure 17B:
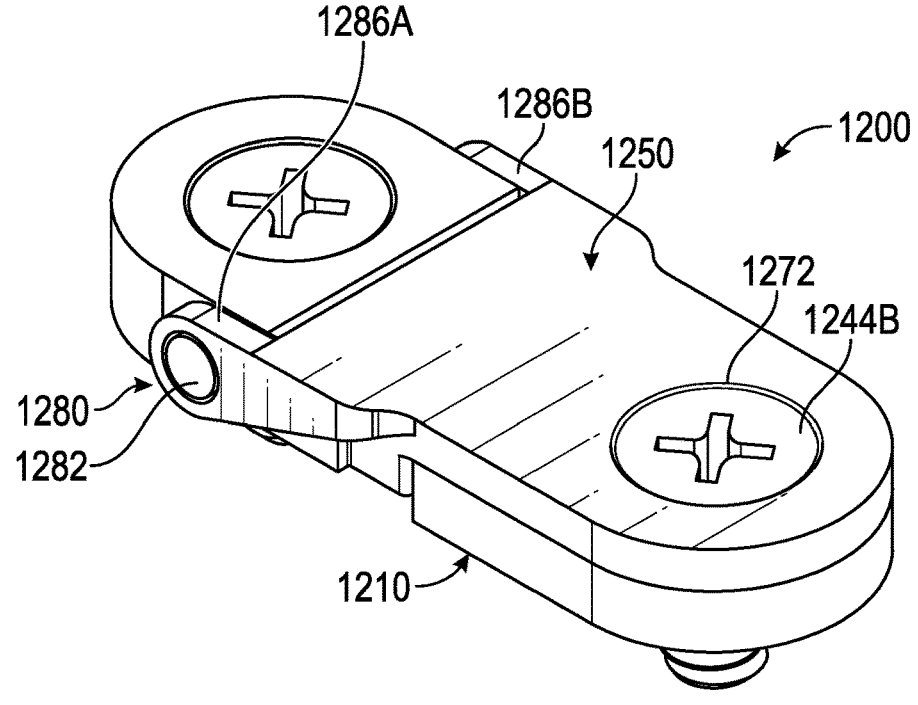
FIG. 17B is a rear perspective view showing the cranial lead fixation device of FIG. 17A in a second closed configuration.
Figure 17C:
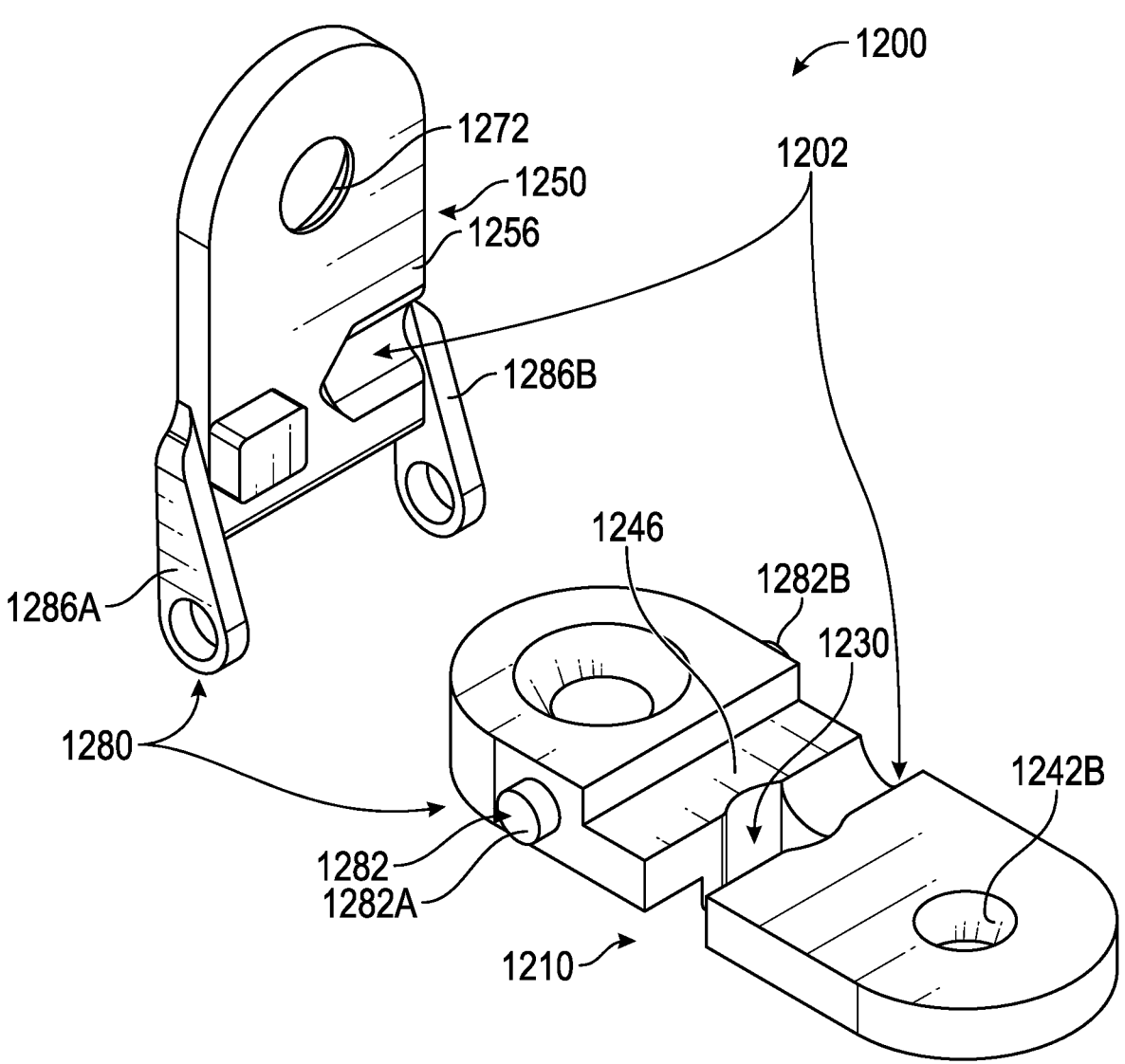
FIG. 17C is an exploded view showing a base and a fixation mechanism of the cranial lead fixation device of FIG. 17A.
Figure 17D:
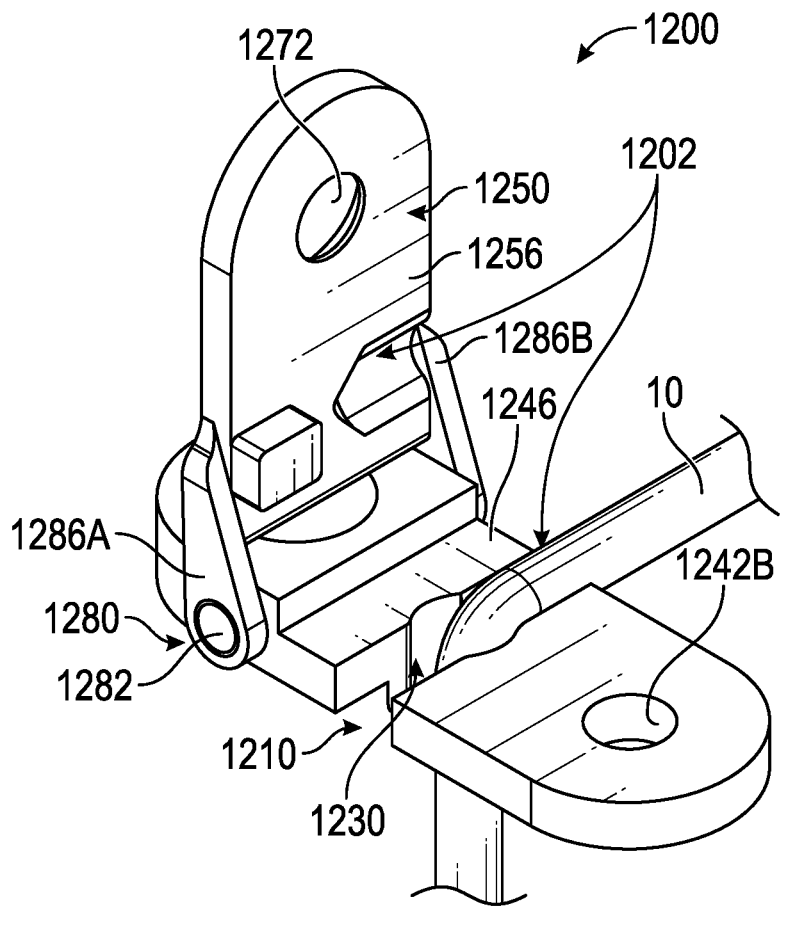
FIG. 17D is a rear perspective view showing the cranial lead fixation device of FIG. 17A in a first open configuration and capturing a medical device.

With reference to FIGS. 17A-17D, a twelfth embodiment of the cranial lead fixation device, designated as cranial lead fixation device 1200, is similar to the cranial lead fixation device 1000 of FIGS. 15A-15F and includes a fixation channel 1202 collectively defined by a body 1210 and a fixation mechanism 1250 linked at a connector mechanism 1280, where the body 1210 includes a burr hole aperture 1230 in communication with the fixation channel 1202 for capture of a medical device 10 (FIG. 17D). The cranial lead fixation device 1200 is similarly configurable in a first open configuration shown in FIG. 17A and a second closed configuration shown in FIG. 17B. FIG. 17C provides an exploded view of the cranial lead fixation device 1200, and FIG. 17D provides a view of the cranial lead fixation device 1200 in an open configuration with the medical device 10 captured within the fixation channel 1202. When in the second closed configuration, the fixation mechanism 1250 can occlude the burr hole aperture 1230 of the body 1210.

In contrast with the cranial lead fixation device 1000 of FIGS. 15A-15F, a connector mechanism 1280 of the cranial lead fixation device 1200 can include a hinge arrangement. In particular, the fixation mechanism 1250 can include a first prong 1286A and a second prong 1286B that each couple with the body 1210 at a hinge pin 1282 of the body 1210, where the hinge pin 1282 includes a first hinge pin 1282A that engages with the first prong 1286A and includes a second hinge pin 1282B that engages with the second prong 1286B.

When in the first open configuration of FIG. 17A, the fixation mechanism 1250 is positioned outward and away from the body 1210 as shown. To transition the cranial lead fixation device 1200 to the second closed configuration of FIG. 17D, the fixation mechanism 1250 can be rotated about the hinge pin 1282 and towards the body 1210 such that an inner face 1256 of the fixation mechanism 1250 couples along a shelf 1246 of the body 1210 as shown. When in the closed configuration of FIG. 17D, a second cranial screw seat 1272 of the fixation mechanism 1250 aligns with a second cranial screw aperture 1242B of the body 1210 for receipt of a second cranial screw 1244B for fixation to the cranium similar to that of the cranial lead fixation device 1000 of FIGS. 15A-15F.

With reference to FIGS. 18A-18E, a thirteenth embodiment of the cranial lead fixation device, designated as cranial lead fixation device 1300, is similar to the cranial lead fixation device 1000 of FIGS. 15A-15F and includes a fixation channel 1302 collectively defined by a body 1310 and a fixation mechanism 1350 linked at a connector mechanism 1380, where the body 1310 includes a burr hole aperture 1330 in communication with the fixation channel 1302 for capture of a medical device (shown as medical device 10 in FIGS. 1A-1F with reference to cranial lead fixation device 100, but is similarly applicable for the cranial lead fixation device 1300 of FIGS. 18A-18E). The cranial lead fixation device 1300 is similarly configurable in a first open configuration shown in FIGS. 18A and 18B and a second closed configuration shown in FIG. 18C-18E. When in the second closed configuration, the fixation mechanism 1350 can occlude the burr hole aperture 1330 of the body 1310.

In contrast with the cranial lead fixation device 1000 of FIGS. 15A-15F and the cranial lead fixation device 1200 of FIGS. 17A-17C, a connector mechanism 1380 of the cranial lead fixation device 1300 can include a sliding arrangement. In particular, the fixation mechanism 1350 can include a first slider 1382A and a second slider 1382B that extend below an inner face 1356 of the fixation mechanism 1350 and inward as shown. The body 1310 includes a first elongated receptacle 1384A and a second elongated receptacle 1384B defined on opposite sides of the body 1310 and along a peripheral edge of the body 1310 as shown for receipt of the first slider 1382A and the second slider 1382B of the fixation mechanism 1350. In particular, when the fixation mechanism 1350 is coupled along the body 1310, the first elongated receptacle 1384A receives the first slider 1382A and the second elongated receptacle 1384B receives the second slider 1382B such that the first slider 1382A and the second slider 1382B of the fixation mechanism 1350 are operable for lateral translation along the body 1310.

Figure 18A:
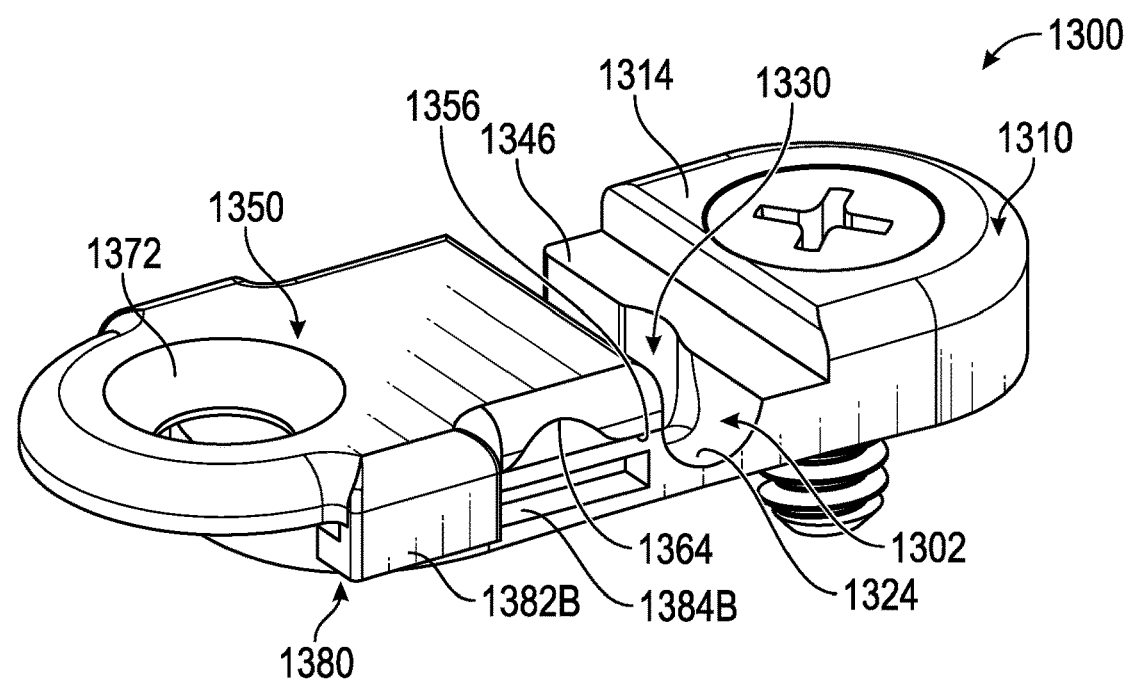
FIG. 18A is a front perspective view showing a thirteenth embodiment of a cranial lead fixation device in a first open configuration.
Figure 18B:
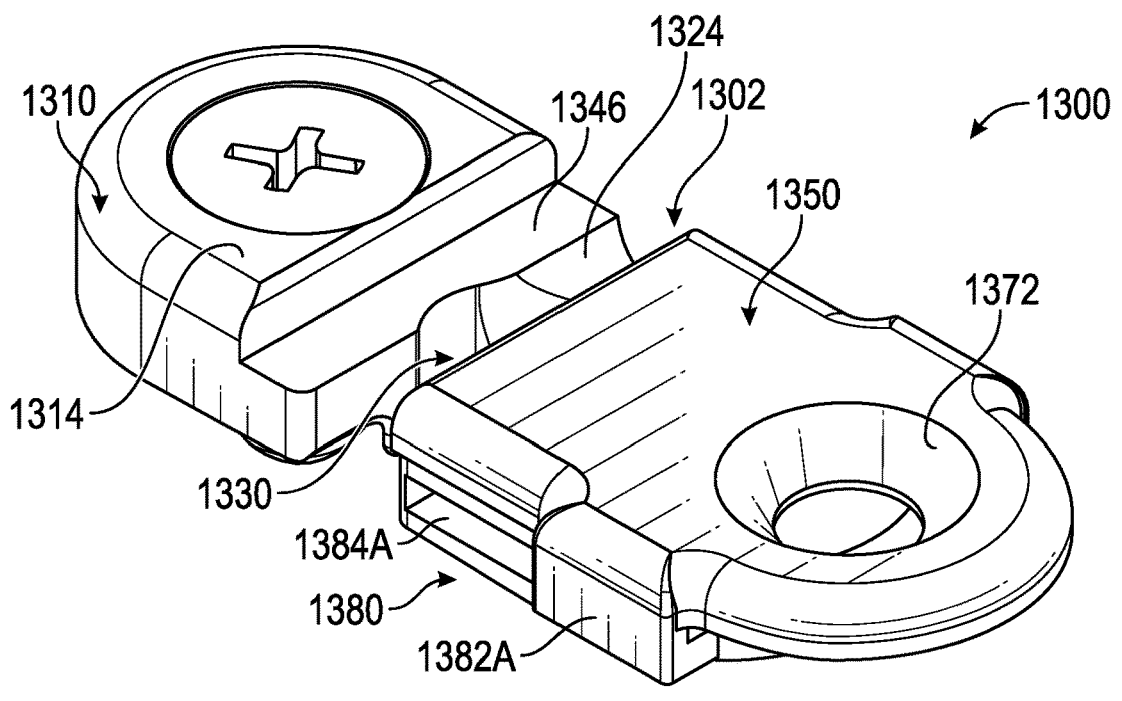
FIG. 18B is a rear perspective view showing the cranial lead fixation device of FIG. 18A in the first open configuration.
Figure 18C:
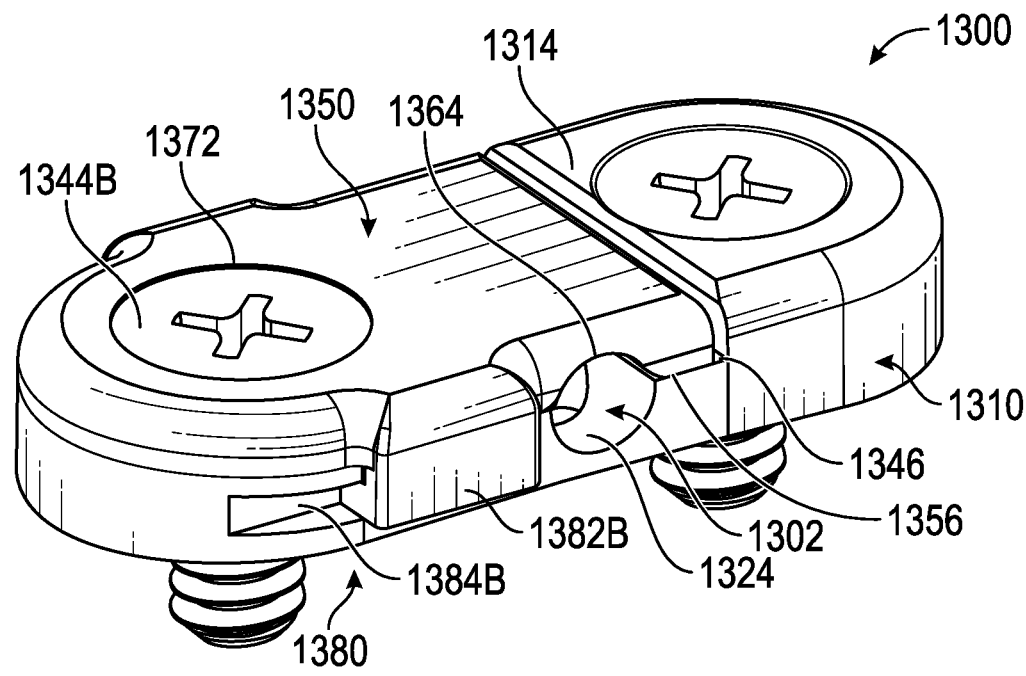
FIG. 18C is a front perspective view showing the cranial lead fixation device of FIG. 18A in a second closed configuration.
Figure 18D:
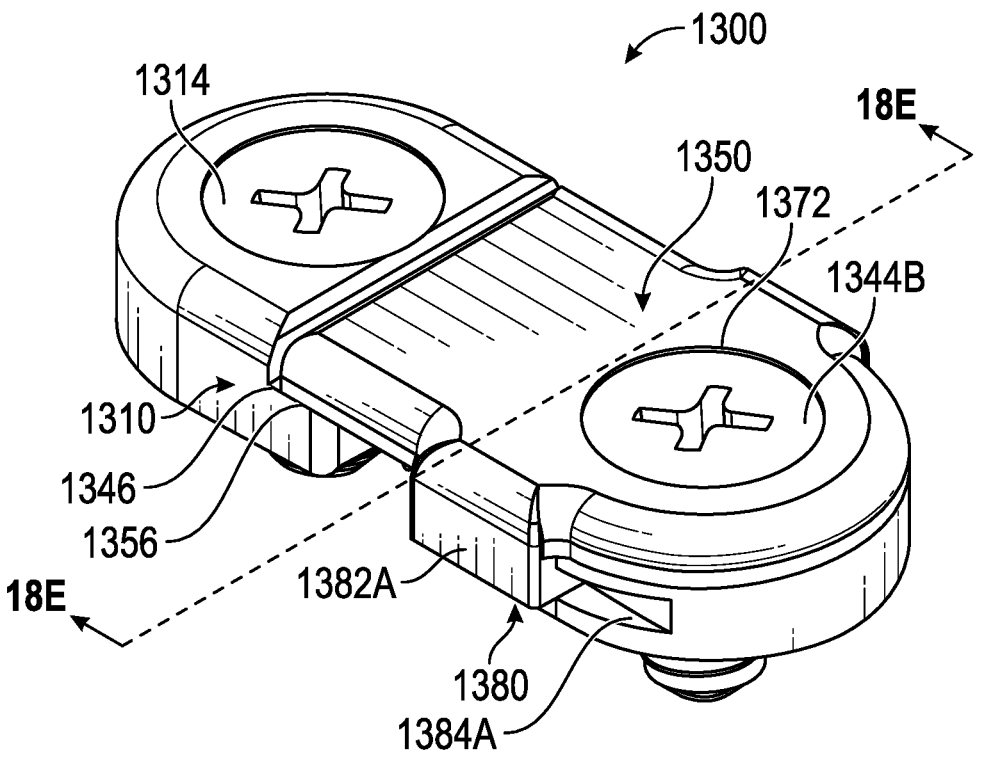
FIG. 18D is a rear perspective view showing the cranial lead fixation device of FIG. 18A in the second closed configuration.
Figure 18E:
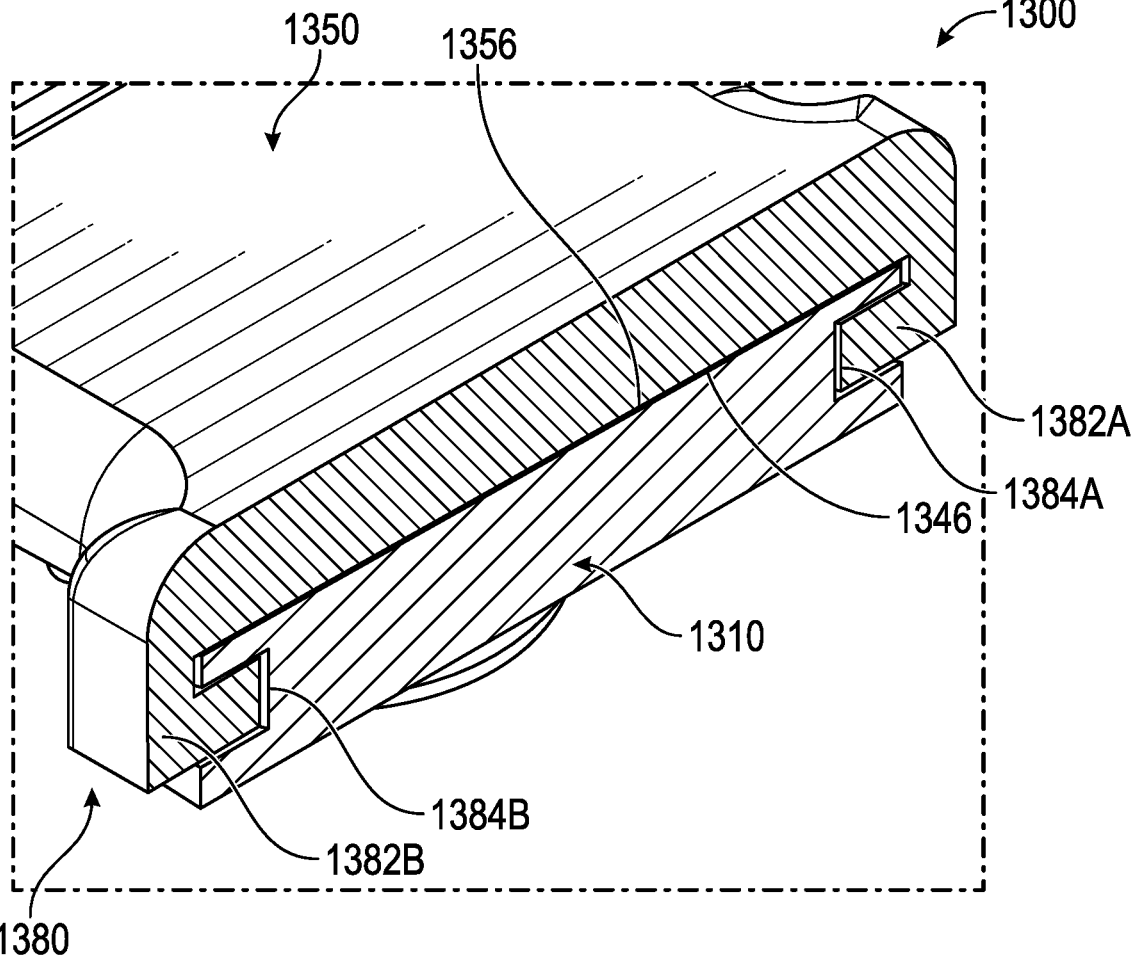
FIG. 18E is a cross-sectional view showing the cranial lead fixation device of FIG. 18D taken across line 18E-18E of FIG. 18D.

When the cranial lead fixation device 1300 is in the first open configuration of FIGS. 18A and 18B, the fixation mechanism 1350 is positioned in a first lateral position along the body 1310 as shown to expose a fixation channel floor 1324 along an outer face 1314 of the body 1310. To transition the cranial lead fixation device 1300 to the second closed configuration of FIGS. 18C-18E, the fixation mechanism 1350 can be slidably translated along the body 1310 such that an inner face 1356 of the fixation mechanism 1350 couples along a shelf 1346 of the body 1310 as shown and a fixation channel ceiling 1364 defined along the inner face 1356 of the fixation mechanism 1350 aligns with the fixation channel floor 1324 of the body 1310 to complete the fixation channel 1302. When in the closed configuration of FIGS. 18C-18E, a second cranial screw seat 1372 of the fixation mechanism 1350 aligns with a second cranial screw aperture (not shown, but analogous to second cranial screw aperture 1042B of FIG. 15A) of the body 1310 for receipt of a second cranial screw 1344B for fixation to the cranium similar to that of the cranial lead fixation device 1000 of FIGS. 15A-15F.

Figure 19A:
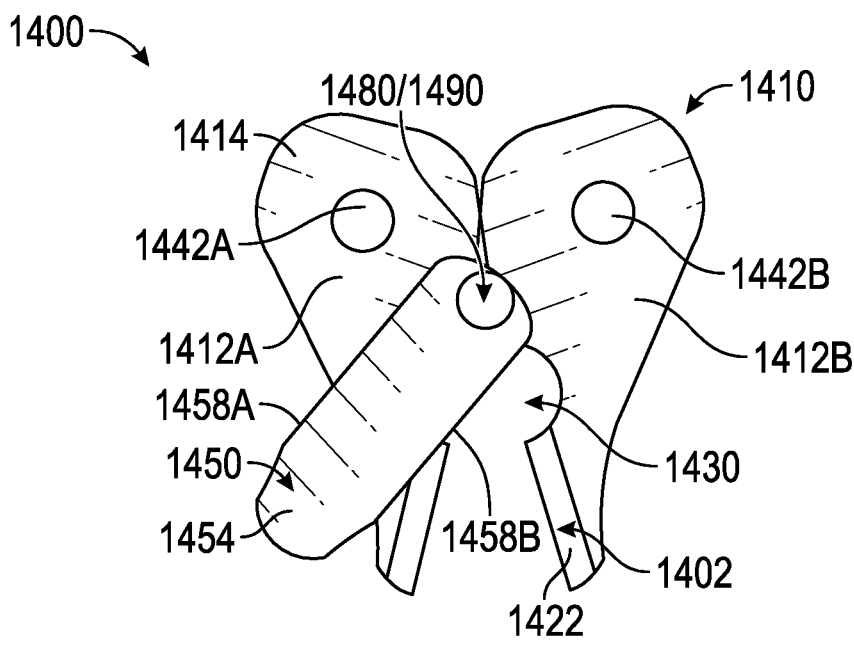
FIG. 19A is a top plan view showing a fourteenth embodiment of a cranial lead fixation device in a first open configuration.
Figure 19B:
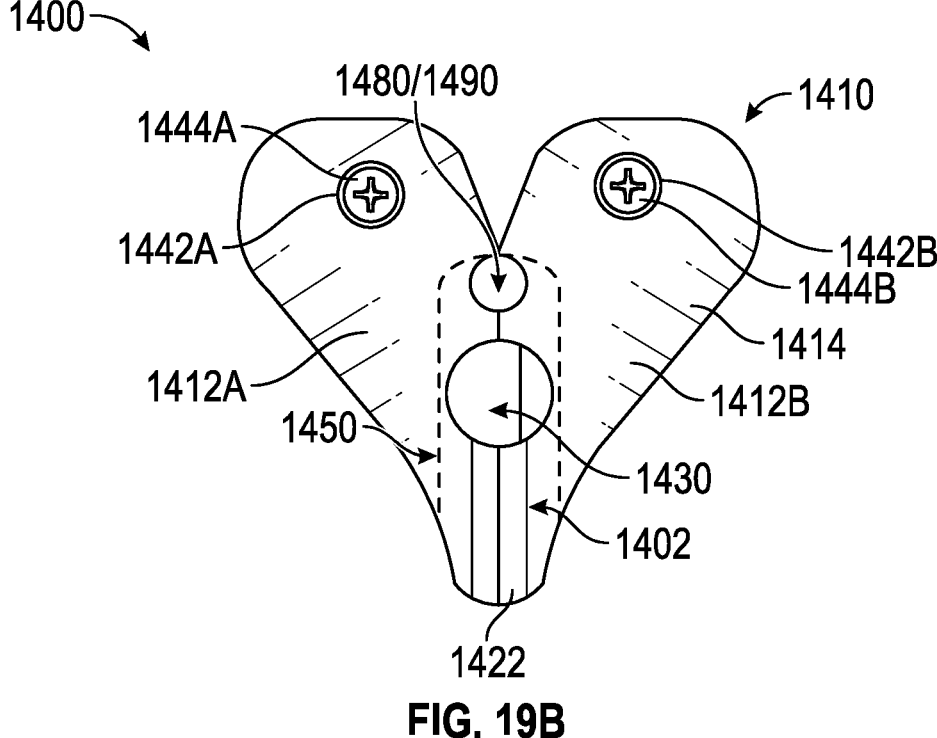
FIG. 19B is a top plan view showing the cranial lead fixation device of FIG. 19A in a second closed configuration.

FIGS. 19A and 19B illustrate a fourteenth embodiment of a cranial lead fixation device, designated as cranial lead fixation device 1400. As shown, the cranial lead fixation device 1400 is operable to assume a first open configuration (FIG. 19A) and a second closed configuration (FIG. 19B). Further, the cranial lead fixation device 1400 includes a fixation channel 1402 for receipt of a medical device (shown as medical device 10 in FIGS. 1A-1F with reference to cranial lead fixation device 100, but is similarly applicable for the cranial lead fixation device 1400 of FIGS. 19A and 19B). When the cranial lead fixation device 1400 is in the first open configuration, the fixation channel 1402 is "open" and operable to accept the medical device. When the cranial lead fixation device 1400 is in the second "closed" configuration, the fixation channel 1402 captures the medical device such that the medical device is prevented from being removed or otherwise pulled away from the cranium.

The cranial lead fixation device 1400 includes a body 1410 that affixes directly to the cranium, and a fixation mechanism 1450 coupled along the body 1410 that transitions the cranial lead fixation device 1400 between the first open configuration of FIG. 19A and the second closed configuration of FIG. 19B and captures the medical device within the fixation channel 1402. Similar to the cranial lead fixation device 400 of FIGS. 7A-7C, the fixation mechanism 1450 can be of an arm-like configuration as shown. In some embodiments, the fixation channel 1402 is collectively defined by the body 1410 and the fixation mechanism 1450; for instance, the body 1410 can define a lower half 1422 of the fixation channel 1402 and the fixation mechanism 1450 can define an upper half (not shown, but analogous to upper half 462 of FIGS. 7A-7C) of the fixation channel 1402. The fixation mechanism 1450 can be coupled along the body 1410 by a connector mechanism 1480, which in some embodiments is a hinge-and-pin configuration that enables rotation of the fixation mechanism 1450 relative to the body 1410, however other configurations are contemplated and described in further embodiments herein.

As shown, the body 1410 can define a first wing 1412A and a second wing 1412B, and further defines an outer face 1414 and an inner face (not shown). As shown, in contrast with preceding embodiments, the first wing 1412A of the body 1410 and the second wing 1412B of the body 1410 are separable from one another and are operable for transitioning between a first open configuration of the body 1410 and a second closed configuration of the body 1410 such that the body 1410 can enclose around the medical device. The first wing 1412A and the second wing 1412B of the body 1410 can be connected at a body hinge 1490 that enables pivoting of the first wing 1412A and the second wing 1412B about the body hinge 1490 between the first open configuration of the body 1410 and the second closed configuration of the body 1410. In some embodiments, the body hinge 1490 can be associated with of the connector mechanism 1480 (e.g., the body hinge 1490 can define the same or similar axis but can be positioned around or inside the connector mechanism 1480, or can alternatively be the same component shared by the first wing 1412A, the second wing 1412B, and the fixation mechanism 1450). In other embodiments, the body hinge 1490 can be completely separate from the connector mechanism 1480; for example, the body hinge 1490 can be positioned between the first wing 1412A and the second wing 1412B as shown in FIGS. 19A and 19B while the connector mechanism 1480 and fixation mechanism 1450 can be oriented similar to the fixation mechanism 550 and connector mechanism 580 of FIG. 8 (e.g., where the fixation mechanism 550 includes a curve and the connector mechanism 580 is positioned off-center).

The body 1410 defines a burr hole aperture 1430 that aligns with the burr hole for capture of the medical device and communicates with the fixation channel 1402; when the body 1410 is in the second closed configuration of the body 1410, the burr hole aperture 1430 encloses around the medical device. Once the medical device is captured at the burr hole aperture 1430, the cranial lead fixation device 1400 can then re-position the fixation mechanism 1450 over the lower half 1422 of the fixation channel 1402 of the body 1410 to transition to the second closed configuration of FIG. 19B and complete the fixation channel 1402. When the cranial lead fixation device 1400 in the second closed configuration of FIG. 19B (e.g., both the body 1410 and the fixation mechanism 1450 are "closed"), the medical device is captured within the fixation channel 1402. As shown, the first wing 1412A of the body 1410 can form a first half of the burr hole aperture 1430 and the second wing 1412B of the body 1410 can form a second half of the burr hole aperture 1430.

When the cranial lead fixation device 1400 is positioned along the cranium, the outer face 1414 faces away from the cranium and the inner face is captured against the cranium;

as such, in some embodiments, the inner face is a concave surface that corresponds with a curvature of the cranium. Further, the body 1410 defines a burr hole aperture 1430 that aligns with the burr hole and communicates with the fixation channel 1402 such that, when captured at the cranial lead fixation device 1400, the medical device extends through the burr hole, the burr hole aperture 1430 of the body 1410, and finally through the fixation channel 1402 as shown. In some embodiments, the body 1410 circumferentially defines a burr hole lip (not shown) around the burr hole aperture 1430 that extends below the inner face (not shown) for improved engagement with the burr hole.

As further shown, the body 1410 includes a plurality of cranial screw apertures (shown in the figures as cranial screw apertures 1442A and 1442B) configured to receive a plurality of cranial screws (shown in the figures as cranial screws 1444A and 1444B) for fixation of the body 1410 to the cranium, including a first cranial screw aperture 1442A configured to receive a first cranial screw 1444A and a second cranial screw aperture 1442B configured to receive a second cranial screw 1444B. The body 1410 can couple along the cranium by insertion of the first cranial screw 1444A into the first cranial screw aperture 1442A and the cranium and by insertion of the second cranial screw 1444B into the second cranial screw aperture 1442B and the cranium. In some embodiments, the first cranial screw aperture 1442A is positioned along the first wing 1412A of the body 1410 and the second cranial screw aperture 1442B is positioned along the second wing 1412B of the body 1410. As shown, the first cranial screw aperture 1442A and the second cranial screw aperture 1442B can be raised, respectively providing a seat for the first cranial screw 1444A and the second cranial screw 1444B.

As discussed and as shown, the fixation mechanism 1450 is coupled with the body 1410 and is operable for rotation, translation, or otherwise re-positioning between the first open configuration of FIG. 19A and the second closed configuration of FIG. 19B. The outer face 1414 of the body 1410 includes a shelf (not shown but analogous to shelf 446 of the cranial lead fixation device 400 of FIGS. 7A-7C) having a first receiving abutment surface and a second receiving abutment surface configured to receive the fixation mechanism 1450, although note that in this embodiment, the shelf can be collectively defined by the first wing 1412A and the second wing 1412B in contrast with the shelf 446 of the cranial lead fixation device 400 of FIGS. 7A-7C.

The fixation mechanism 1450 includes an outer face 1454 and an inner face (not shown) such that when the fixation mechanism 1450 is coupled along the body 1410 and the body 1410 is coupled along the cranium, the outer face 1454 of the fixation mechanism 1450 faces away from the body 1410 and the cranium, and the inner face faces the outer face 1414 of the body 1410 as shown. The fixation mechanism 1450 includes a first terminal abutment surface 1458A that contacts the first receiving abutment surface of the shelf of the body 1410 and a second terminal abutment surface 1458B that contacts the second receiving abutment surface of the shelf of the body 1410 when in the second closed configuration of FIG. 19B. In a further aspect, the fixation mechanism 1450 is coupled along the body 1410 at the connector mechanism 1480, which in the embodiment shown can include a pivot hinge configured for insertion into a first hinge aperture (not shown) of the fixation mechanism 1450 and a second hinge aperture (not shown) of the body 1410. Further, note that the connector mechanism 1480 does not extend below the inner face of the body 1410 to avoid intruding on the cranium. The connector mechanism 1480 provides a pivot point enabling rotation of the fixation mechanism 1450 between the first open configuration of FIG. 19A and the second closed configuration of FIG. 19B.

As shown and as discussed above, the fixation mechanism 1450 forms the upper half (not shown, but analogous to the upper half 462 of the fixation channel 402 of the cranial lead fixation device 400 of FIGS. 7A-7C) of the fixation channel 1402. The body 1410 forms the lower half 1422 of the fixation channel 1402. In particular, the body 1410 includes a fixation channel floor (not shown but analogous to fixation channel floor 424 of the cranial lead fixation device 400 of FIGS. 7A-7C) along the outer face 1414 that forms the lower half 1422 of the fixation channel 1402; similarly, the fixation mechanism 1450 includes a fixation channel ceiling (not shown, but analogous to the fixation channel ceiling 464 of the cranial lead fixation device 400) along the inner face that forms the upper half of the fixation channel 1402. When the cranial lead fixation device 1400 is in the second closed configuration of FIG. 19B, the lower half 1422 of the fixation channel 1402 and the upper half of the fixation channel 1402 are aligned with one another to complete the fixation channel 1402. When in the second closed configuration, the fixation mechanism 1450 can occlude the burr hole aperture 1430 of the body 1410.

As discussed above, the cranial lead fixation device 1400 can be affixed directly to the cranium. To couple the body 1410 along the cranium, the first wing 1412A or the second wing 1412B can first be affixed to the cranium by insertion of the first cranial screw 1444A into the first cranial screw aperture 1442A or by insertion of the second cranial screw 1444B into the second cranial screw aperture 1442B. Then, the medical device can be positioned to align with the burr hole aperture 1430 and the body 1410 can be transitioned into the second closed configuration of the body 1410, bringing the first wing 1412A and the second wing 1412B of the body 1410 together and capturing the medical device within the burr hole aperture 1430. Note that when the body 1410 is in the second closed configuration of the body 1410, the cranial lead fixation device 1400 can still be considered in the first open configuration if the fixation mechanism 1450 is in the first open configuration. Following coupling of the body 1410 to the cranium and following capture of the medical device within the burr hole aperture 1430 and the lower half 1422 of the fixation channel 1402, a practitioner can position the fixation mechanism 1450 from the first open configuration of FIG. 19A into the second closed configuration of FIG. 19B to complete the fixation channel 1402 such that the medical device is enclosed within the fixation channel 1402.

Further, note that while the figures show an arm-like configuration of the fixation mechanism 1450 rotatable between the first open configuration of FIG. 19A and the second closed configuration of FIG. 19B (analogous to the fixation mechanism 450 of the cranial lead fixation device 400 of FIGS. 7A-7C), the fixation mechanism 1450 could also be of a plate-like configuration (analogous to the fixation mechanism 150 of the cranial lead fixation device 100 of FIGS. 1A-1F, the fixation mechanism 750 of the cranial lead fixation device 700 of FIGS. 10A-12B, and the fixation mechanism 1050 of the cranial lead fixation device 1000 of FIGS. 15A-15F).

Figure 20:
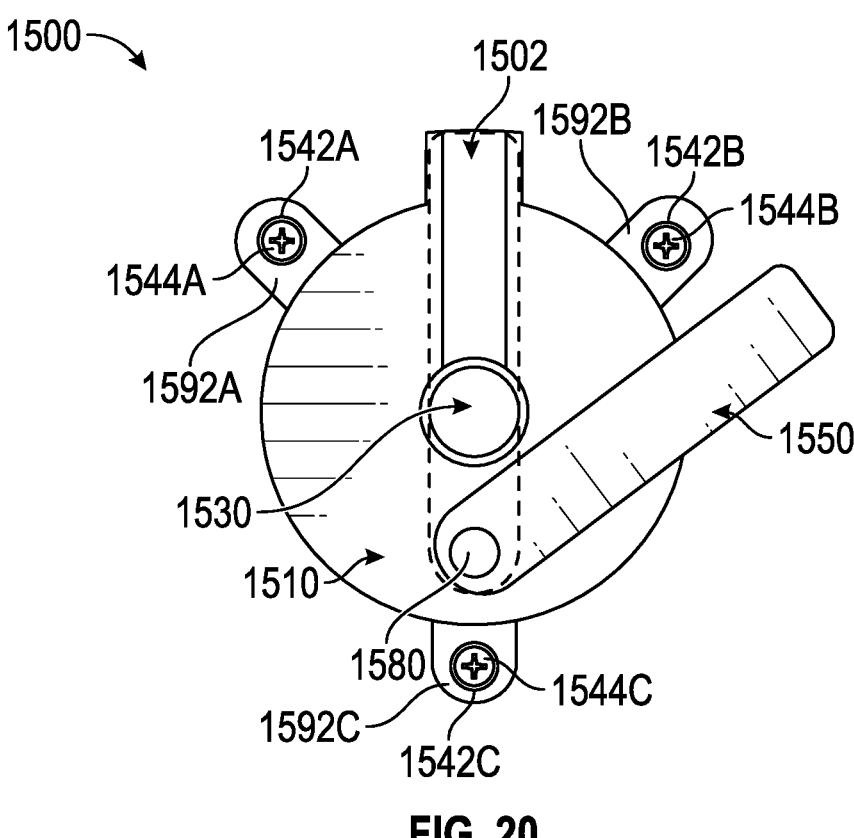
FIG. 20 is a top plan view showing a fifteenth embodiment of a cranial lead fixation device operable for transitioning between a first open configuration and a second closed configuration.

FIG. 20 shows a fifteenth embodiment of the cranial lead fixation device, designated as cranial lead fixation device 1500, that is similar to the cranial lead fixation device 400 and includes a fixation channel 1502 collectively defined by a body 1510 and a fixation mechanism 1550 linked at a connector mechanism 1580, where the body 1510 includes a burr hole aperture 1530 in communication with the fixation channel 1502 for capture of a medical device (shown as medical device 10 in FIGS. 1A-1F with reference to cranial lead fixation device 100, but is similarly applicable for the cranial lead fixation device 1500 of FIG. 20). The cranial lead fixation device 1500 is similarly configurable in a first open configuration and a second closed configuration. In the embodiment shown, the fixation mechanism 1550 is of an arm-like configuration analogous to the fixation mechanism 450 of the cranial lead fixation device 400 of FIGS. 7A-7C; however, note that in other embodiments, the fixation mechanism 1550 can be of a plate-like configuration analogous to the fixation mechanism 150 of the cranial lead fixation device 100 of FIGS. 1A-1F, the fixation mechanism 750 of the cranial lead fixation device 700 of FIGS. 10A-12B, and the fixation mechanism 1050 of the cranial lead fixation device 1000 of FIGS. 15A-15F. When in the second closed configuration, the fixation mechanism 1550 can occlude the burr hole aperture 1530 of the body 1510.

In contrast to the cranial lead fixation device 400, the body 1510 can be of a generally rounded configuration (e.g., eliminating the first, second and/or third wings in favor of a simplified, radial shape) and can include a plurality of cranial screw apertures (shown in the figures as cranial screw apertures 1542A, 1542B and 1542C) positioned along an external perimeter of the body 1510 (e.g., along the "side" of the body 1510) as shown. The plurality of cranial screw apertures can include a first cranial screw aperture 1542A, a second cranial screw aperture 1542B, and a third cranial screw aperture 1542C for respective receipt of a first cranial screw 1544A, a second cranial screw 1544B and a third cranial screw 1544C; the first cranial screw aperture 1542A, the second cranial screw aperture 1542B and the third cranial screw aperture 1542C can be equally or asymmetrically distributed along the body 1510. In particular, the body 1510 can include a plurality of tabs including a first tab 1592A, a second tab 1592B, and a third tab 1592C that each respectively include the first cranial screw aperture 1542A, the second cranial screw aperture 1542B, and the third cranial screw aperture 1542C.

Figure 21:
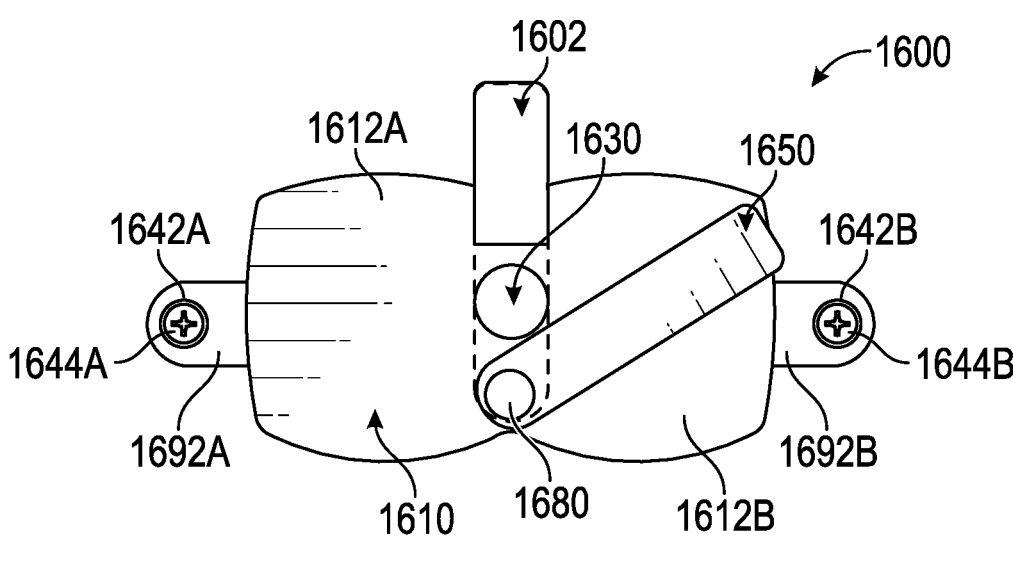
FIG. 21 is a top plan view showing a sixteenth embodiment of a cranial lead fixation device operable for transitioning between a first open configuration and a second closed configuration.

FIG. 21 shows a sixteenth embodiment of the cranial lead fixation device, designated as cranial lead fixation device 1600, that is similar to the cranial lead fixation device 1500 and includes a fixation channel 1602 collectively defined by a body 1610 and a fixation mechanism 1650 linked at a connector mechanism 1680, where the body 1610 includes a burr hole aperture 1630 in communication with the fixation channel 1602 for capture of a medical device (shown as medical device 10 in FIGS. 1A-1F with reference to cranial lead fixation device 100, but is similarly applicable for the cranial lead fixation device 1500 of FIG. 21). The cranial lead fixation device 1600 is similarly configurable in a first open configuration and a second closed configuration. In the embodiment shown, the fixation mechanism 1650 is of an arm-like configuration analogous to the fixation mechanism 450 of the cranial lead fixation device 400 of FIGS. 7A-7C; however, note that in other embodiments, the fixation mechanism 1650 can be of a plate-like configuration analogous to the fixation mechanism 150 of the cranial lead fixation device 100 of FIGS. 1A-1F, the fixation mechanism 750 of the cranial lead fixation device 700 of FIGS. 10A-12B, and the fixation mechanism 1050 of the cranial lead fixation device 1000 of FIGS. 15A-15F. When in the second closed configuration, the fixation mechanism 1650 can occlude the burr hole aperture 1630 of the body 1610.

In contrast to the cranial lead fixation device 1500, the body 1610 can include a first wing 1612A and a second wing

1612B and can include a plurality of cranial screw apertures (shown in the figures as cranial screw apertures 1642A and 1642B) positioned along an external perimeter of the body 1610 (e.g., along the "side" of the body 1610) as shown. The plurality of cranial screw apertures can include a first cranial screw aperture 1642A positioned along an external perimeter of the first wing 1612A and a second cranial screw aperture 1642B positioned along an external perimeter of the second wing 1612B for respective receipt of a first cranial screw 1644A and a second cranial screw 1644B; the first cranial screw aperture 1642A and the second cranial screw aperture 1642B can be equally or asymmetrically distributed along the body 1610. In particular, the body 1610 can include a plurality of tabs including a first tab 1692A and a second tab 1692B that each respectively include the first cranial screw aperture 1642A and the second cranial screw aperture 1642B.

Figure 22A:
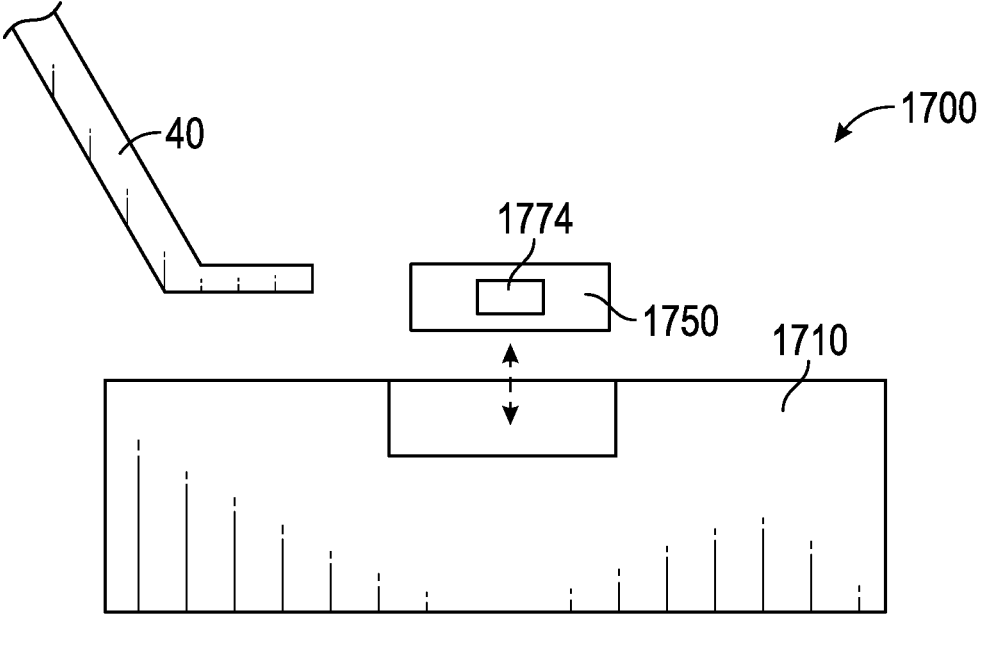
FIG. 22A is a side view showing a seventeenth embodiment of a cranial lead fixation device having a fixation mechanism that is rotatable about a pivot axis and featuring a slot for engagement with an instrument, where the slot can be included in any preceding embodiment of FIGS. 1A-21.
Figure 22B:
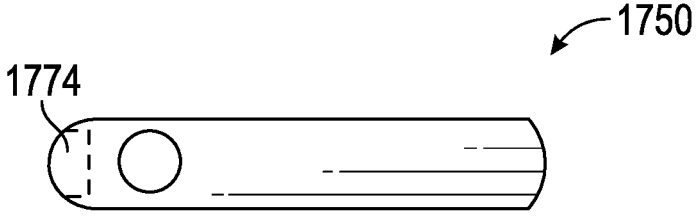
FIG. 22B is a top plan view showing the fixation mechanism and the slot of the cranial lead fixation device of FIG. 22A.

FIGS. 22A and 22B show a seventeenth embodiment of the cranial lead fixation device, designated as cranial lead fixation device 1700, that includes a body 1710 and a fixation mechanism 1750 having a slot 1774 that aids transitioning of the cranial lead fixation device 1700 between a first closed configuration and a second open configuration. The cranial lead fixation device 1700 can be analogous to the cranial lead fixation device 400 of FIGS. 7A-7C and other embodiments described herein that include an arm-like fixation mechanism; in other embodiments, the cranial lead fixation device 1700 can be analogous to the cranial lead fixation device 100 of FIGS. 1A-1F and other embodiments described herein that include a plate-like fixation mechanism. Likewise, note that the slot 1774 of the cranial lead fixation device 1700 can be present along other embodiments of the fixation mechanism for any of the preceding embodiments (e.g., along fixation mechanism 150 of FIGS. 1A-1F, fixation mechanism 450 of FIGS. 7A-7C, fixation mechanism 750 of FIGS. 10A-12B, fixation mechanism 1050 of FIGS. 15A-15F, fixation mechanism 1450 of FIGS. 19A and 19B and other similar embodiments described herein). As such, the fixation mechanism 1750 can be rotatable and/or removeable from the body 1710 similar to that of previously discussed embodiments of the fixation mechanism. The slot 1774 enables a practitioner to actuate the fixation mechanism 1750 between the first closed configuration and the second open configuration using an instrument 40 by insertion of the instrument 40 into the slot 1774 and subsequent actuation of the fixation mechanism 1750 to an appropriate position.

Figure 23A:
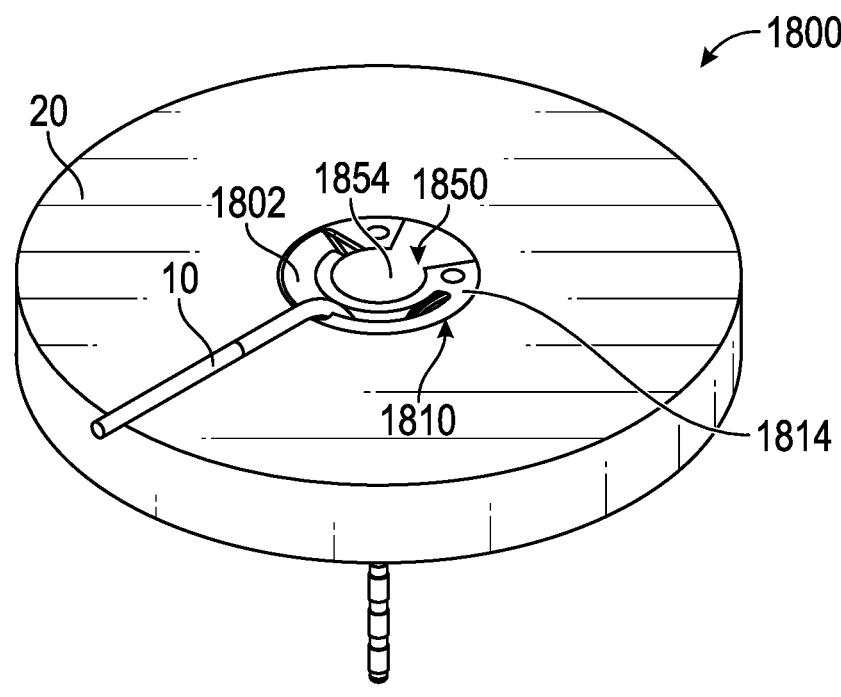
FIG. 23A is a top front perspective view showing an eighteenth embodiment of a cranial lead fixation device having a radial arrangement and configured for insertion within a burr hole aperture of a cranium for capture of a medical device.
Figure 26A:
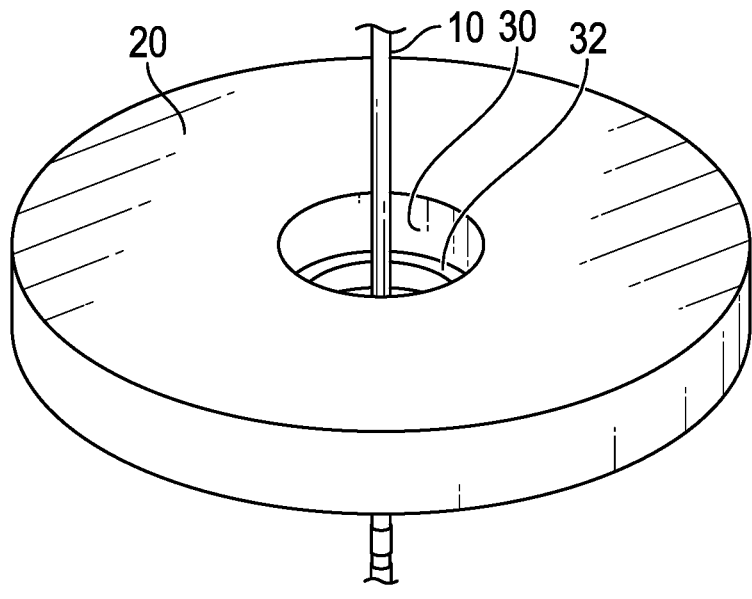
FIG. 26A is an illustration showing a burr hole and medical device for insertion of the cranial lead fixation device of FIG. 23B.
Figure 26B:
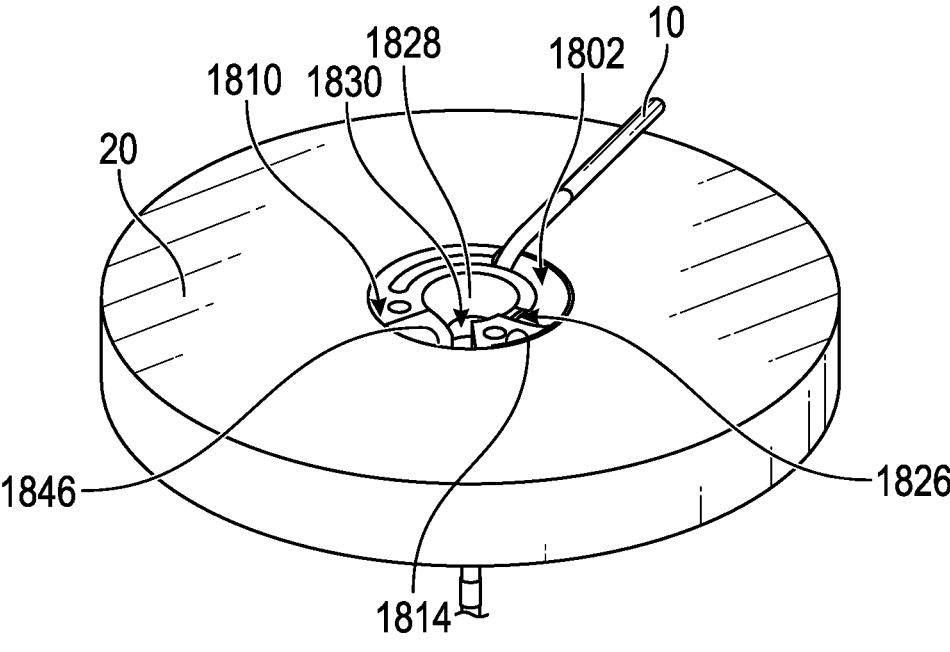
FIG. 26B is an illustration showing insertion of the base of FIG. 24A into the burr hole of FIG. 26A and capture of the medical device at the base.
Figure 26C:
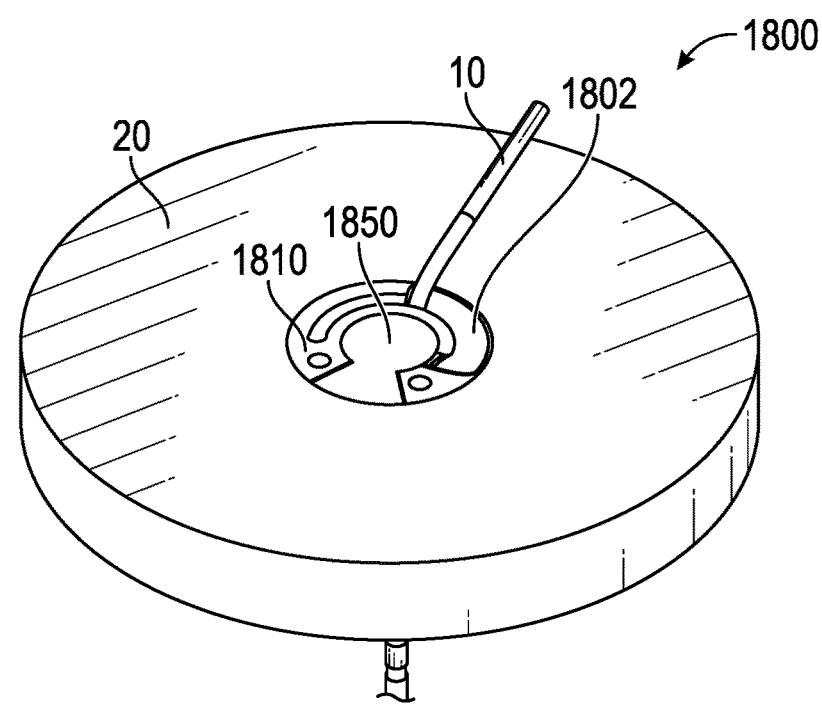
FIG. 26C is an illustration showing coupling of the fixation mechanism of FIG. 25A with the base of FIG. 26B to complete the cranial lead fixation device of FIG. 25A.
Figure 26D:
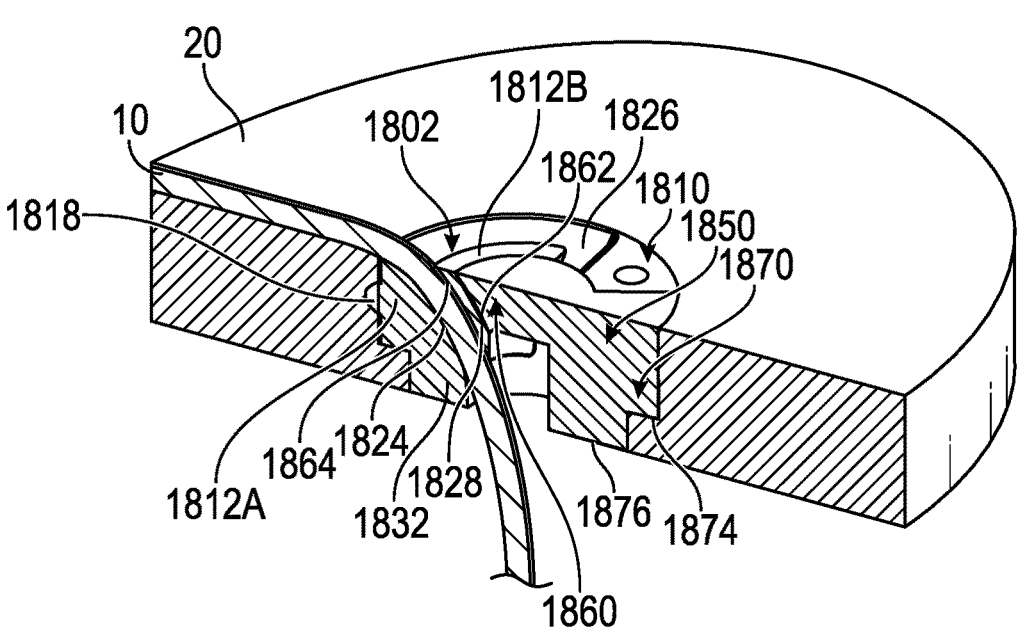
FIG. 26D is a cross-sectional view showing the cranial lead fixation device of FIG. 26B.
Figure 27A:
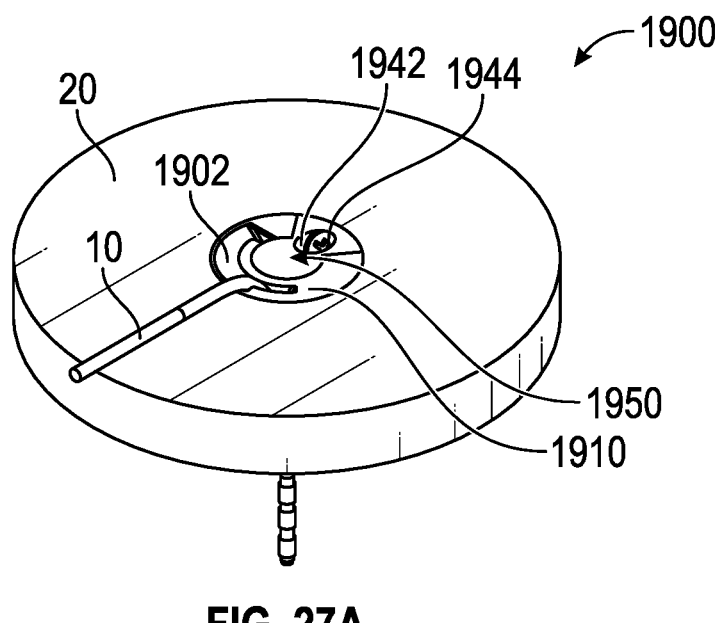
FIG. 27A is a top front perspective view showing a nineteenth embodiment of a cranial lead fixation device having a radial arrangement and configured for insertion within a burr hole aperture of a cranium for capture of a medical device, where the cranial lead fixation device includes a cranial screw.
Figure 27B:
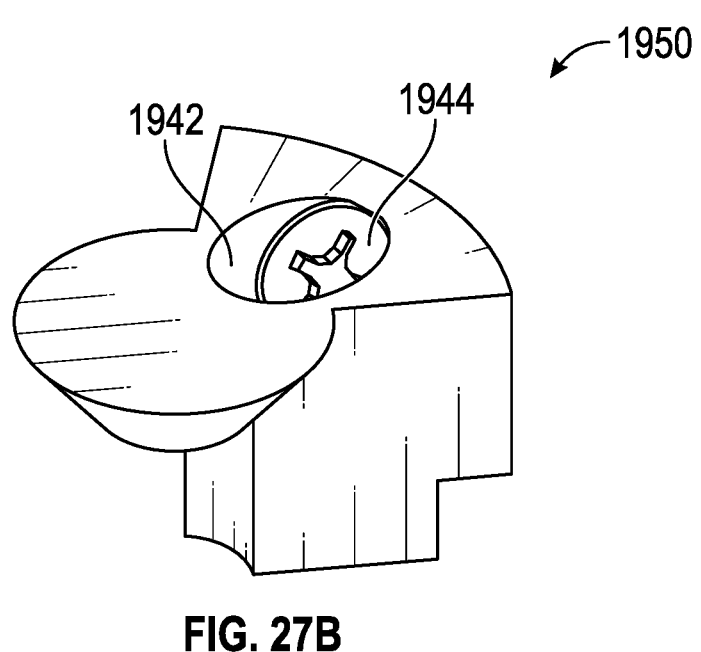
FIG. 27B is a front perspective view showing a fixation mechanism of the cranial lead fixation device of FIG. 27A having the cranial screw.
Figure 27C:
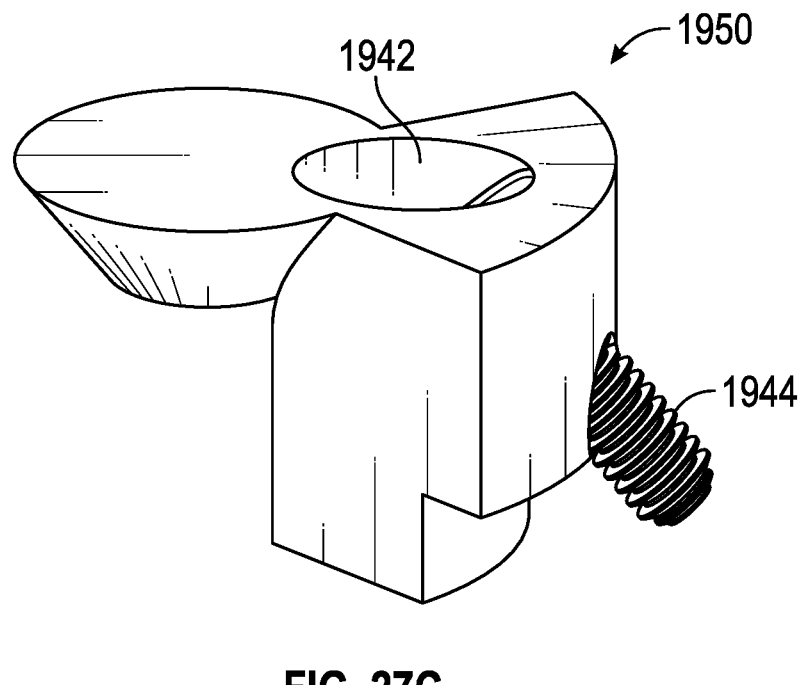
FIG. 27C is a rear perspective view showing the fixation mechanism of FIG. 27A.
Figure 27D:
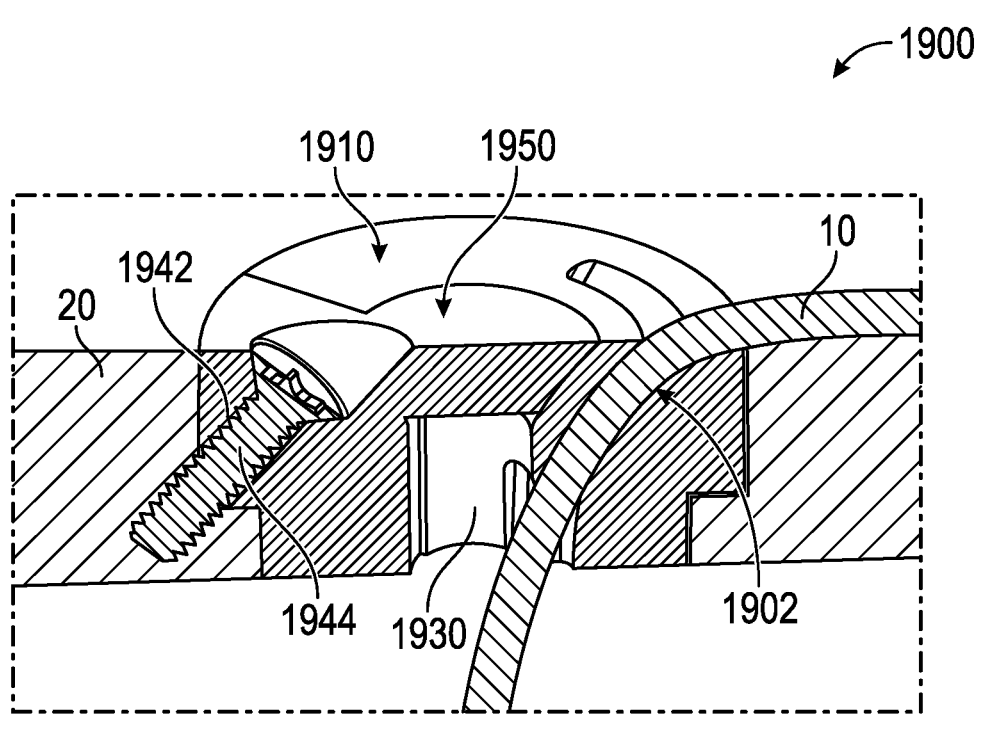
FIG. 27D is a cross-sectional view showing the cranial lead fixation device of FIG. 27A.

FIGS. 23A-26D illustrate an eighteenth embodiment of the cranial lead fixation device, designated as cranial lead fixation device 1800, for capturing and securing a medical device 10 within a burr hole 30 formed within a cranium 20. FIGS. 23A, 26C and 26D in particular show the cranial lead fixation device 1800 positioned along the cranium 20 and recessed into the burr hole 30 such that the cranial lead fixation device 1800 lies flush with the cranium 20. As shown, the cranial lead fixation device 1800 is operable to assume a first open configuration (FIG. 23D) and a second closed configuration (FIG. 23A). Further, the cranial lead fixation device 1800 includes a fixation channel 1802 for receipt of the medical device 10 such that when the cranial lead fixation device 1800 is in the first open configuration, the fixation channel 1802 is "open" and operable to accept the medical device 10 and capture the medical device 10 such that the medical device 10 is prevented from being removed or otherwise pulled away from the cranium 20. When the cranial lead fixation device 1800 is in the second "closed" configuration, an "exit" of the fixation channel 1802 is blocked, preventing removal of the medical device 10 from the fixation channel 1802.

Figure 23B:
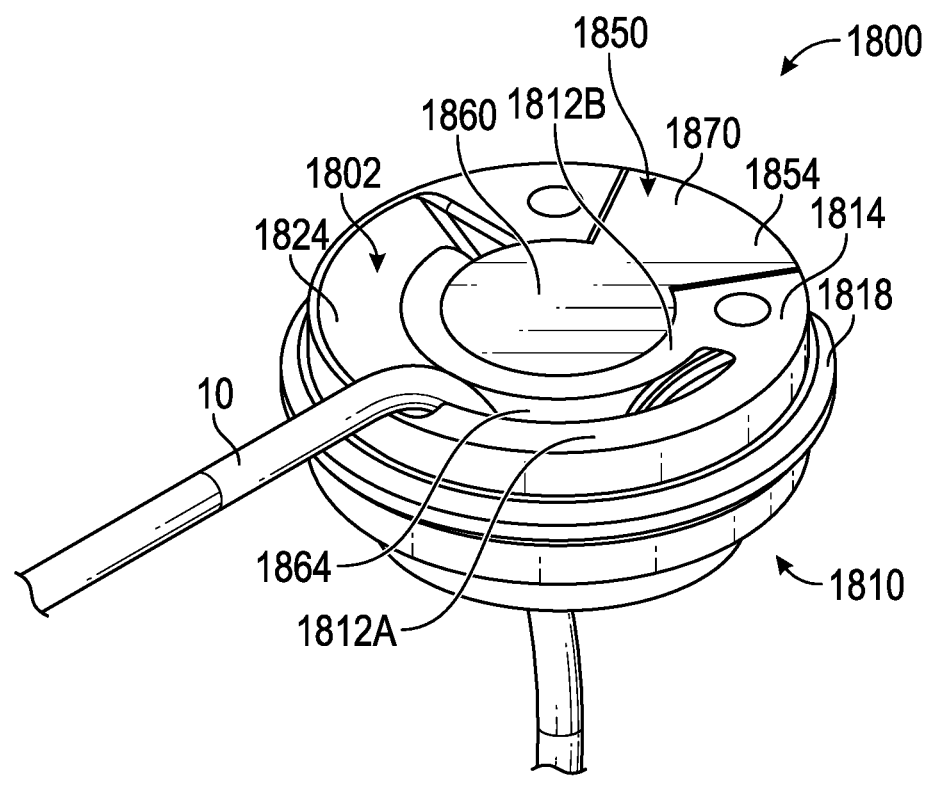
FIG. 23B is a top front perspective view showing the cranial lead fixation device of FIG. 23A without the cranium and with the medical device.
Figure 23C:
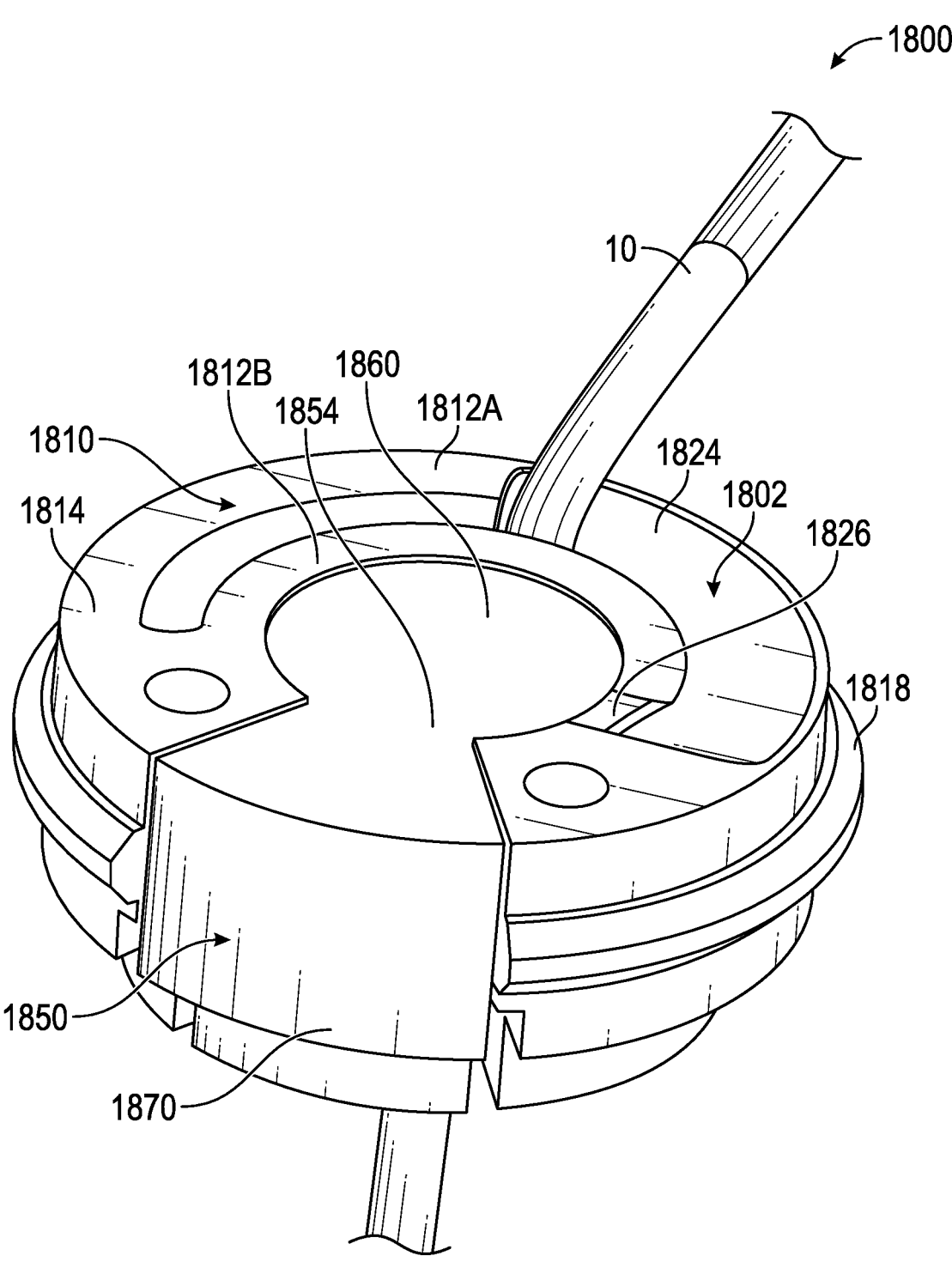
FIG. 23C is a top rear perspective view showing the cranial lead fixation device of FIG. 23B.
Figure 23D:
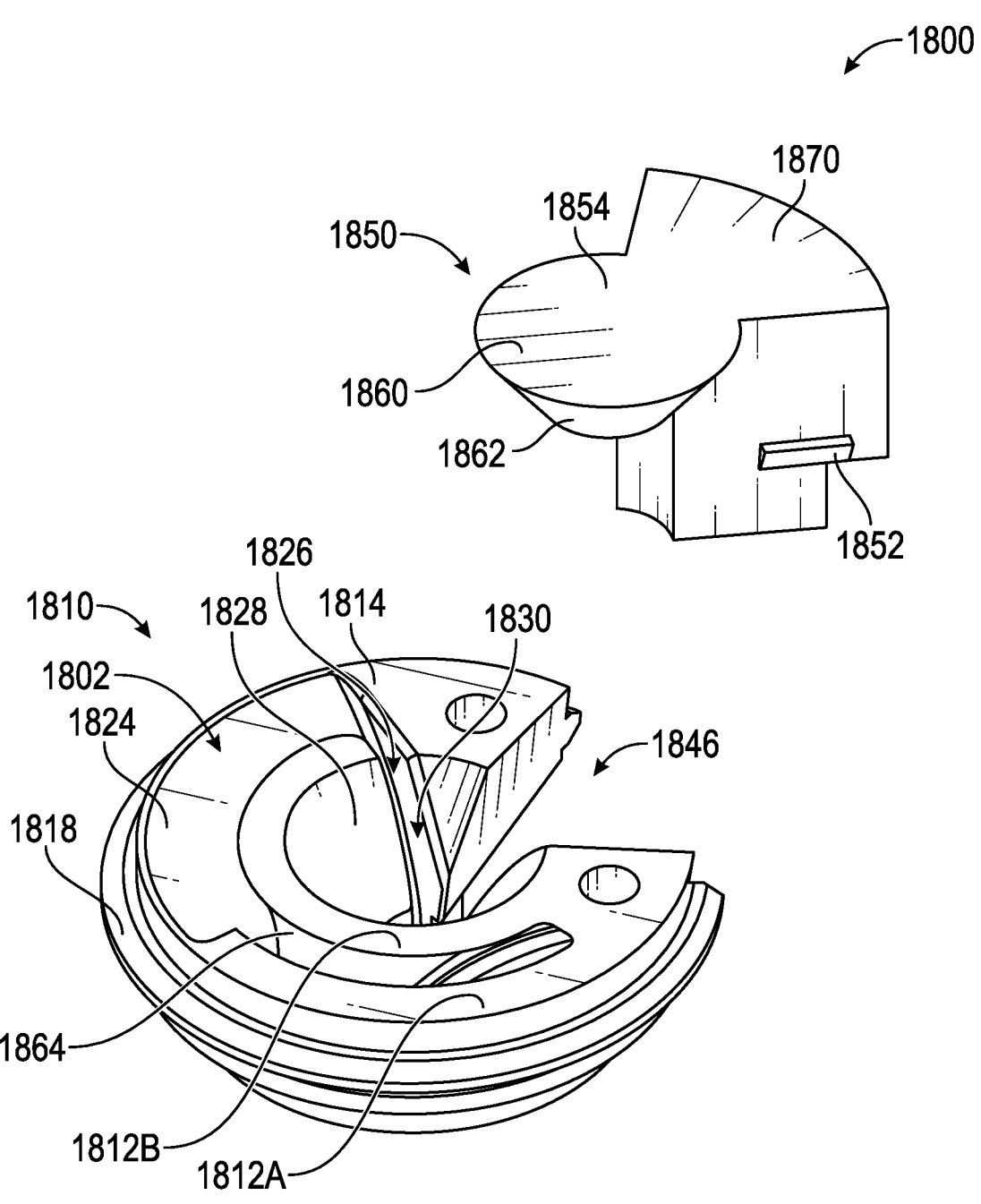
FIG. 23D is an exploded view showing the cranial lead fixation device of FIG. 23B.
Figure 24A:
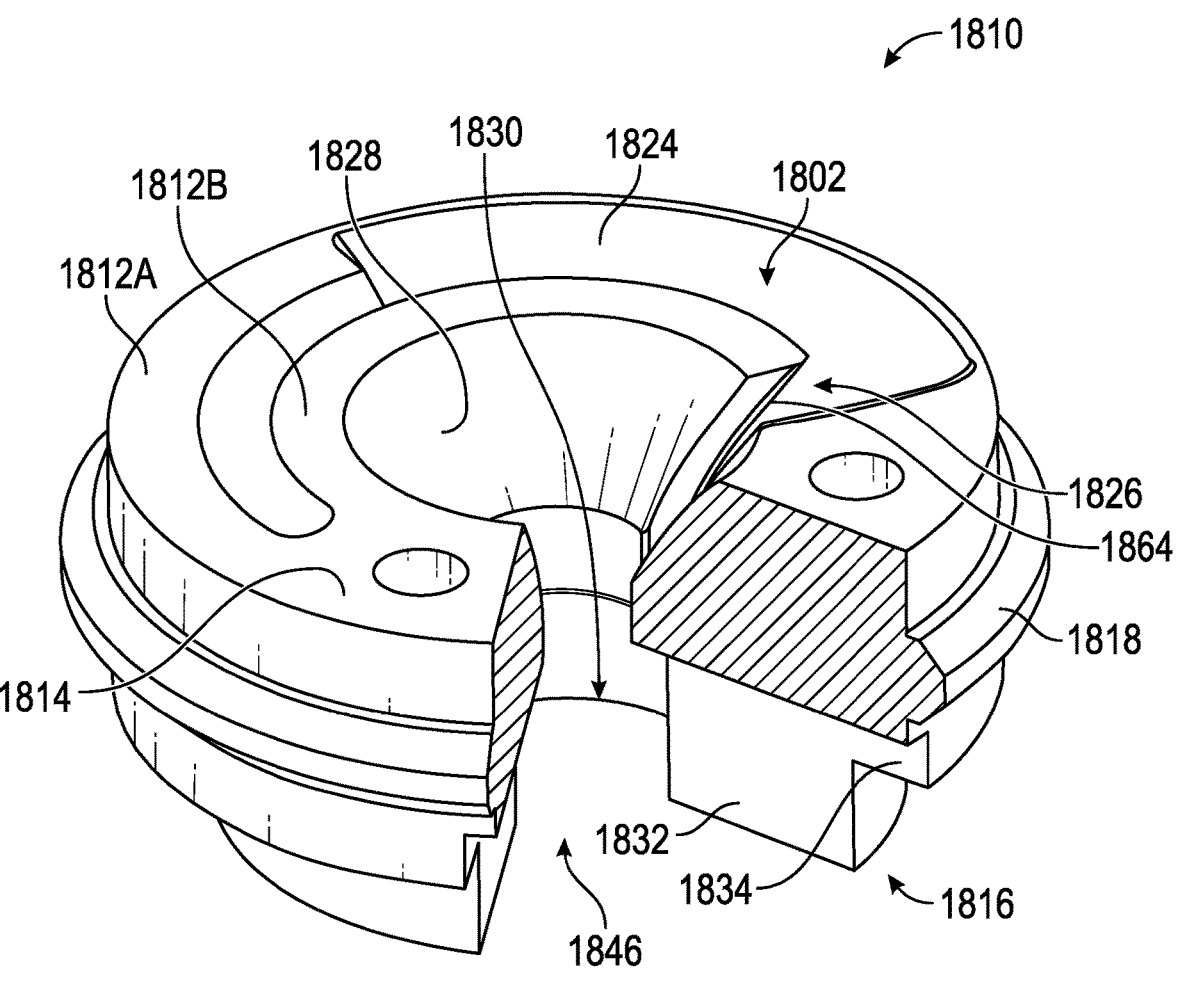
FIG. 24A is a rear perspective view showing a base of the cranial lead fixation device of FIG. 23B.
Figure 24B:
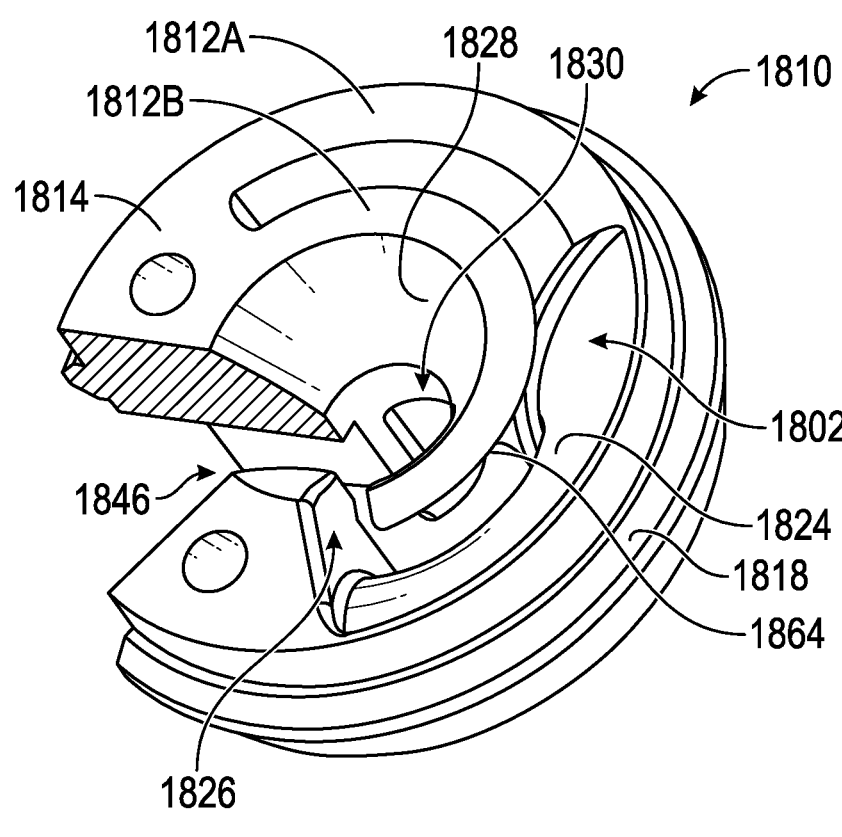
FIG. 24B is a front perspective view showing the base of FIG. 24A.
Figure 24C:
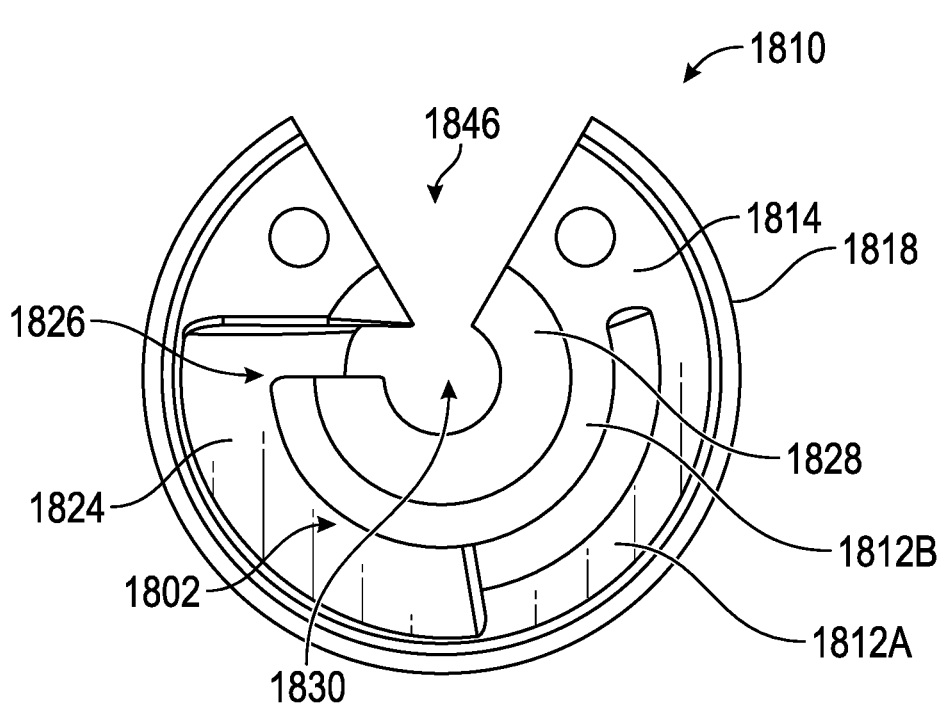
FIG. 24C is a top plan view showing the base of FIG. 24A.
Figure 24D:
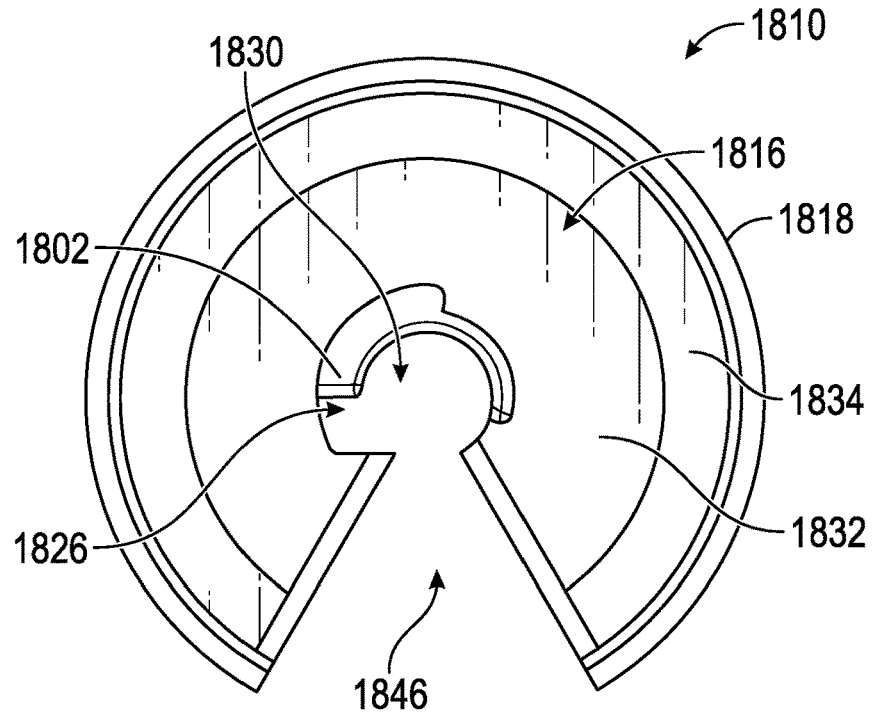
FIG. 24D is a bottom plan view showing the base of FIG. 24A.
Figure 24E:
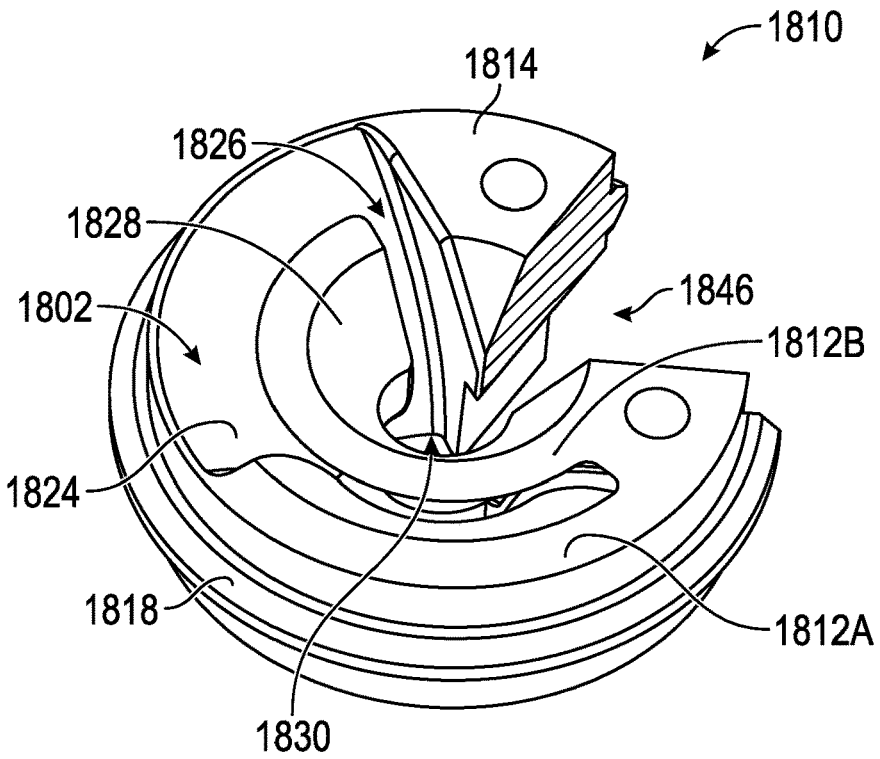
FIG. 24E is an additional front perspective view showing the base of FIG. 24A.

As shown, the cranial lead fixation device 1800 includes a body 1810 that affixes directly within the burr hole 30 of the cranium 20, and a fixation mechanism 1850 coupled along the body 1810 that transitions the cranial lead fixation device 1800 between the first open configuration of FIG. 23D and the second closed configuration of FIGS. 23A-23C. When in the first open configuration of FIG. 23D, the fixation mechanism 1850 is decoupled from the body 1810; and in the second closed configuration of FIGS. 23A-23C, the fixation mechanism 1850 is coupled with the body 1810.

The body 1810 of the cranial lead fixation device 1800 is shown in FIGS. 23D-24E; in contrast with the preceding embodiments discussed herein, the fixation channel 1802 is fully defined by the body 1810, which defines a radial configuration including an outer concentric portion 1812A and an inner concentric portion 1812B with the fixation channel 1802 therebetween as shown. As such, the outer concentric portion 1812A defines a fixation channel floor 1824 of the fixation channel 1802 and the inner concentric portion 1812B defines a fixation channel ceiling 1864 of the fixation channel 1802. The body 1810 defines an outer ridge 1818 that couples within the burr hole 30 of the cranium 20, an outer face 1814 that is flush with the cranium 20 when the body 1810 is positioned within the burr hole 30, and an inner face 1816 that inserts directly into the burr hole 30. When the cranial lead fixation device 1800 is positioned along the cranium 20, the outer face 1814 faces away from the cranium 20 and the inner face 1816 is captured within the burr hole 30.

Further, the body 1810 defines a burr hole aperture 1830 that aligns with the burr hole 30 and communicates with the fixation channel 1802 such that, when captured at the cranial lead fixation device 1800, the medical device 10 extends through the burr hole 30, the burr hole aperture 1830 of the body 1810, and finally through the fixation channel 1802 as shown. In some embodiments, the body 1810 circumferentially defines a burr hole lip 1832 around the burr hole aperture 1830 that extends below the inner face 1816 for improved engagement with the burr hole 30. The body 1810 can also include a receiving funnel 1828 in association with the burr hole aperture 1830 and an open sector 1846 that communicates with the burr hole aperture 1830 and the fixation channel 1802 for insertion of the fixation mechanism 1850. The open sector 1846 can include an insertion channel 1826 that enables insertion of the medical device 10 from the burr hole aperture 1830 and into the fixation channel 1802. In addition, the inner face 1816 of the body 1810 can include an upper section 1834 and the burr hole lip 1832; the upper section 1834 sits within the burr hole 30 (e.g., along a burr hole shelf 32 of the burr hole 30 shown in FIG. 26A) and the burr hole lip 1832 inserts fully into the burr hole 30.

The body 1810 is configured to receive the fixation mechanism 1850 in a removeable engagement. As shown, the fixation mechanism 1850 is configured for engagement with the receiving funnel 1828 and the open sector 1846 of the body 1810, and defines a generally plug-like configuration. When coupled with the body 1810, the fixation mechanism 1850 closes off the insertion channel 1826 to prevent migration of the medical device 10 out of the fixation channel 1802. In particular, as shown in FIGS. 25A-25C, the fixation mechanism 1850 includes a rounded portion 1860 and a triangular portion 1870 that collectively define an outer face 1854 and an inner face 1856, where the outer face 1854 is flush with the body 1810. The inner face 1856 can include a first inner face 1856A associated with the rounded portion 1860 and a second inner face 1856B associated with the triangular portion 1870. The triangular portion 1870 of the fixation mechanism 1850 is configured for engagement within the open sector 1846 of the body 1810 and the rounded portion 1860 is configured for engagement within the receiving funnel 1828 of the body 1810. The rounded portion 1860 defines an angular outer edge 1862 as shown that matches the "grade" or angle of the receiving funnel 1828 of the body 1810. The triangular portion 1870 defines a first terminal abutment surface 1858A and a second terminal abutment surface 1858B that couple with the open sector 1846 of the body 1810, and can include one or more protrusions 1852 along the first terminal abutment surface 1858A and the second terminal abutment surface 1858B of the triangular portion 1870 as shown to secure the fixation mechanism 1850 within the open sector 1846 of the body 1810. In addition, the second inner face 1856B associated with the triangular portion 1870 can include an upper section 1874 and a lower section 1876; the upper section 1874 sits within the burr hole 30 (e.g., along a burr hole shelf 32 of the burr hole 30) and the lower section 1876 inserts fully into the burr hole 30 when the fixation mechanism 1850 is positioned within the body 1810. When in the second closed configuration, the fixation mechanism 1850 can occlude the burr hole aperture 1830 of the body 1810.

FIGS. 26A-26D show a sequence for installation of the cranial lead fixation device 1800. FIG. 26A shows the cranium 20 which includes the burr hole 30 defining the burr hole shelf 32, and the medical device 10 extending from the burr hole 30. FIG. 26B shows the body 1810 of the cranial lead fixation device 1800 inserted within the burr hole 30 with the medical device 10 captured within the fixation channel 1802 of the cranial lead fixation device 1800. FIG. 26C shows the fixation mechanism 1850 coupled with the body 1810 to enclose the fixation channel 1802 and prevent migration of the medical device 10 out of the fixation channel 1802. FIG. 26D shows a cross-sectional view of the cranial lead fixation device 1800 fully assembled and positioned within the burr hole 30.

With reference to FIGS. 27A-27D, a nineteenth embodiment of the cranial lead fixation device, designated as cranial lead fixation device 1900, is similar to the cranial lead fixation device 1800 of FIGS. 23A-26D and includes a fixation channel 1902 for receipt of the medical device 10 such that when the cranial lead fixation device 1900 is in a first open configuration (analogous to the first open configuration shown in FIG. 23D with respect to the cranial lead fixation device 1800), the fixation channel 1902 is "open" and operable to accept the medical device 10 and capture the medical device 10 such that the medical device 10 is prevented from being removed or otherwise pulled away from the cranium 20. When the cranial lead fixation device 1900 is in a second "closed" configuration shown in FIGS. 27A and 27D, an "exit" of the fixation channel 1902 is blocked, preventing removal of the medical device 10 from the fixation channel 1902. As shown, the cranial lead fixation device 1900 includes a body 1910 that affixes directly within the burr hole 30 of the cranium 20, and a fixation mechanism 1950 coupled along the body 1910 that transitions the cranial lead fixation device 1900 between the first open configuration and the second closed configuration of FIGS. 27A and 27D. When in the first open configuration, the fixation mechanism 1950 is decoupled from the body 1910; and in the second closed configuration of FIGS. 27A and 27D, the fixation mechanism 1950 is coupled with the body 1910. When in the second closed configuration, the fixation mechanism 1950 can occlude the burr hole aperture 1930 of the body 1910.

In contrast with the cranial lead fixation device 1800 of FIGS. 23A-26D, the fixation mechanism 1950 can include a cranial screw aperture 1942 for receipt of a cranial screw 1944 that fixes the fixation mechanism 1950 to the cranium 20 and prevents removal of the body 1910 and the fixation mechanism 1950 from the burr hole 30. As shown, the cranial screw aperture 1942 can be angled to maximize engagement with the cranium 30. To install the cranial lead fixation device 1900, the body 1910 of the cranial lead fixation device 1900 is first inserted within the burr hole 30 and the medical device 10 is captured within the fixation channel 1902 of the cranial lead fixation device 1900. Then, the fixation mechanism 1950 is coupled with the body 1910 to enclose the fixation channel 1902 and prevent migration of the medical device 10 out of the fixation channel 1902. Following engagement of the fixation mechanism 1950 with the body 1910, the cranial screw 1944 is inserted into the cranial screw aperture 1942 and the cranium 20 as shown in the cross-sectional view of FIG. 27D.

Methods

FIGS. 28A-28E illustrate a method 2000 for capturing a medical device (such as medical device 10) using the cranial lead fixation devices 100-1900 of FIGS. 1A-27D.

With reference to FIG. 28A, an overall view of the method 2000 is provided. Step 2010 of method 2000 includes coupling a body of a device (e.g., a cranial lead fixation device 100-1900) with a cranium of a patient such that a burr hole aperture of the body is positioned over or within a burr hole of the cranium, the device being configured in a first open configuration and being operable to transition from the first open configuration to a second closed configuration. Step 2020 of method 2000 includes capturing, within the burr hole aperture of the device, a medical device extending from the burr hole. Step 2030 of method 2000 includes positioning the medical device within a fixation channel of the device. Finally, step 2040 of method 2000 includes transitioning the device from the first open configuration to the second closed configuration such that the medical device is captured within the fixation channel of the device.

Referring to FIG. 28B, step 2010 can include various sub-steps depending on the embodiment of the cranial lead fixation device 100-1900. Steps 2012A and 2012B correspond with cranial lead fixation devices 100-1700; step 2012A includes positioning an inner face of the body against the cranium and step 2014A includes inserting a cranial screw into the body and the cranium to fix the body to the cranium. In contrast, step 2012B corresponds with cranial lead fixation devices 1800 and 1900, and includes inserting the body into a burr hole of the cranium such that an outer face of the body is flush with the cranium.

Referring to FIG. 28C, step 2020 can include various sub-steps depending on the embodiment of the cranial lead fixation device 100-1900. Step 2022A corresponds with cranial lead fixation devices 100-300 and 700-1300 and includes inserting the medical device through an insertion channel of the body and into the burr hole aperture. Step 2022B corresponds with cranial lead fixation device 1400 and includes rotating at least one of a first wing or a second wing of the body of the device about a body hinge from a first open configuration of the body to a second closed configuration of the body such that the medical device is captured within a burr hole aperture collectively defined by the first wing and the second wing of the body.

Referring to FIG. 28D, step 2040 can include various sub-steps depending on the embodiment of the cranial lead fixation device 100-1900. Step 2042A corresponds with cranial lead fixation devices 100-600, 800, 1200 and 1400-1700 and includes rotating a fixation mechanism of the device about a connector mechanism from the first open configuration to the second closed configuration. Step 2044A follows step 2042A and corresponds with cranial lead fixation devices 100-300 and 1200, and includes inserting a cranial screw through the fixation mechanism, the body of the device, and into the cranium to fix the fixation mechanism and the body of the device to the cranium. Step 2042B corresponds with cranial lead fixation devices 700, 1000, 1100, 1500, 1800 and 1900 and includes coupling a fixation mechanism of the device with the body of the device to transition the device from the first open configuration to the second closed configuration. Additional steps 2044B and 2046B can follow step 2042B; step 2044B corresponds with cranial lead fixation devices 700, 1000, 1100 and 1500 and can include inserting a cranial screw through the fixation mechanism, the body of the device, and into the cranium to fix the fixation mechanism and the body of the device to the cranium. Conversely, step 2046B can follow step 2042B and corresponds with cranial lead fixation devices 1800 and 1900, and can include inserting a cranial screw through the fixation mechanism and into the cranium to fix the fixation mechanism and the body of the device to the cranium, where the fixation mechanism secures the body of the device to the cranium.

FIG. 28E includes additional steps 2042C and 2044C that follow step 2040 and pertain to cranial lead fixation device 1300. Step 2042C includes translating a fixation mechanism of the device from a first lateral position associated with the first open configuration to a second lateral position associated with the second closed configuration, and step 2044C includes inserting a cranial screw through the fixation mechanism, the body of the device, and into the cranium to fix the fixation mechanism and the body of the device to the cranium.

Corresponding reference characters indicate corresponding elements among the view of the drawings. The headings used in the figures do not limit the scope of the claims.

What is claimed is:

1. A device, comprising:
   a body including:
   a burr hole aperture defining a central axis;
   a first portion of a fixation channel, the first portion of the fixation channel being in communication with the burr hole aperture; and
   an insertion channel in communication with the burr hole aperture for insertion of a medical device through the insertion channel and into the burr hole aperture; and
   a fixation mechanism pivotably coupled to the body by a connector mechanism defining a pivot axis that is substantially parallel to the central axis of the burr hole aperture, the fixation mechanism being rotatable about the pivot axis between a first open configuration and a second closed configuration, and the fixation mechanism having an inner face and a protrusion projecting from the inner face;
   wherein rotation of the fixation mechanism about the pivot axis from the first open configuration into the second closed configuration positions the protrusion within the insertion channel to occlude the insertion channel, completes the fixation channel, and occludes the burr hole aperture.

2. The device of claim 1, wherein the body defines an inner face and an outer face, the inner face being configured for engagement with a cranium of a patient.

3. The device of claim 2, wherein the inner face of the body further comprises a burr hole lip defined circumferentially around the burr hole aperture.

4. The device of claim 2, the inner face of the fixation mechanism being configured for engagement along the outer face of the body, the inner face of the fixation mechanism defining a second portion of the fixation channel that aligns with the first portion of the fixation channel to complete the fixation channel when in the second closed configuration.

5. The device of claim 2, wherein the inner face of the body is a concave surface that corresponds to a curvature of the cranium of the patient.

6. The device of claim 1, wherein the body defines at least one cranial screw aperture configured for engagement with at least one cranial screw, wherein the at least one cranial screw is configured and arranged to secure the device to a cranium of a patient.

7. The device of claim 6, wherein the at least one cranial screw aperture includes a first cranial screw aperture and a second cranial screw aperture and the at least one cranial screw includes a first cranial screw and a second cranial screw, and wherein the fixation mechanism includes a second cranial screw seat that aligns with the second cranial screw aperture when the device is in the second closed configuration, wherein the first cranial screw aperture is configured to receive the first cranial screw to secure the body to a cranium of a patient and wherein the second cranial screw aperture and the second cranial screw seat are collectively configured to receive the second cranial screw configured and arranged to secure the body and the fixation mechanism to a cranium of a patient.

8. The device of claim 1, wherein the connector mechanism includes a cranial screw configured for insertion into a cranial screw seat of the fixation mechanism and a cranial screw aperture of the body, wherein the cranial screw is configured and arranged to secure the device to a cranium of a patient.

9. The device of claim 1, wherein the fixation channel and the burr hole aperture are collectively configured to capture the medical device therein.

10. The device of claim 9, wherein the fixation mechanism is configured and arranged to apply a force to the medical device captured at the fixation channel.

11. The device of claim 1, wherein the fixation mechanism defines a plate shape for rotatable and/or removeable engagement along an outer face of the body.

12. A method, comprising:

a body defining an inner face, an outer face, and a burr hole aperture defining a central axis, the inner face being configured for engagement with a cranium of a patient;

forming a first portion of a fixation channel along the outer face of the body and in communication with the burr hole aperture;

forming an insertion channel in communication with the burr hole aperture for insertion of a medical device through the insertion channel and into the burr hole aperture;

providing a fixation mechanism having an inner face;

forming a first hinge aperture in the body and a second hinge aperture in the fixation mechanism, the first hinge aperture and the second hinge aperture being coaxially positionable to receive a pivot hinge of a connector mechanism that defines a pivot axis substantially parallel to the central axis of the burr hole aperture, such that, when the fixation mechanism is coupled to the body by the connector mechanism, the fixation mechanism is rotatable about the pivot axis between a first open configuration and a second closed configuration; and forming a protrusion projecting from the inner face of the fixation mechanism such that rotation of the fixation mechanism into the second closed configuration positions the protrusion within the insertion channel to occlude the insertion channel, completes the fixation channel, and occludes the burr hole aperture.

13. The method of claim 12, further comprising:

positioning an inner face of the body against a cranium of a patient such that the burr hole aperture of the body is positioned over a burr hole of the cranium; and inserting a cranial screw into the body and the cranium to fix the body to the cranium.

14. The method of claim 12, further comprising:

inserting the medical device through the insertion channel of the body and into the burr hole aperture.

15. The method of claim 12, further comprising:

rotating the fixation mechanism about the connector mechanism from the first open configuration to the second closed configuration.

16. The method of claim 15, further comprising:

inserting a cranial screw through the fixation mechanism, the body, and into the cranium to fix the fixation mechanism and the body to the cranium.

17. The method of claim 12, further comprising:

coupling the connector mechanism to at least one of the body and the fixation mechanism.

\* \* \* \* \*